(12) United States Patent
Beitz et al.

(10) Patent No.: US 7,910,308 B1
(45) Date of Patent: Mar. 22, 2011

(54) GENETIC MARKERS IN FATTY ACID SYNTHASE FOR IDENTIFICATION OF MEAT PRODUCT FATTY ACID CONTENT IN CATTLE

(75) Inventors: Donald C. Beitz, Ames, IA (US); Shu Zhang, King of Prussia, PA (US); Travis J. Knight, Slater, IA (US); James M. Reecy, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 12/177,436

(22) Filed: Jul. 22, 2008

Related U.S. Application Data

(60) Provisional application No. 60/951,873, filed on Jul. 25, 2007.

(51) Int. Cl.
*C12Q 1/68* (2006.01)
*C12P 19/34* (2006.01)
*C07H 21/02* (2006.01)

(52) U.S. Cl. .......... 435/6; 435/91.2; 536/23.1; 536/24.3

(58) Field of Classification Search .................. None
See application file for complete search history.

(56) References Cited

OTHER PUBLICATIONS

Hacker U.T. et al. Gut (May 1997) vol. 40 No. 5, pp. 623-627.*
Roy R. et al. Animal Genetics (2006) vol. 37 pp. 215-218 and two pages of supplemental material.*
Lawless F. et al. Livestock Production Science 62 (1999) 43-49.*
Morris C.A. et al. Mammalian Genome (2006) vol. 18 pp. 64-74.*
Abstract information for Zhang S. et al. FASEB Journal, (Apr. 2007) vol. 21, No. 6, pp. A1120. printed abstract only provided, one page.*
Herpers B. L. et al. Molecular Immunology 43 (2006) 851-855.*
Noack, Kristin et al., "The Role of Fatty Acid Synthase in Creating Healthier Beef", Economic Research Service USDA, Aug. 2006, pp. 1-4.
Noack, Kristin et al., "The Role of Fatty Acid Synthase in Creating Healthier Beef", Powerpoint presentation, Aug. 2006, 1 page.

* cited by examiner

*Primary Examiner* — Stephen Kapushoc
(74) *Attorney, Agent, or Firm* — McKee, Voorhees & Sease, P.L.C.

(57) ABSTRACT

Genetic markers associated with fatty acid content in meat products from animals, particularly Angus cattle, are described. The genetic markers are located in the thioesterase-encoding region of the fatty acid synthase gene. The markers allow animals to be characterized for breeding or for identification purposes to indicate animals likely to have a distribution of fatty acids that are healthier, thus generating improved meat products.

8 Claims, 10 Drawing Sheets

```
Cattle    FGSPAQSHTQLNLSTLLVNPEGPTLTRLNSVQSSERPLFLVHPIEGSTTVFHSLATKLSI    2268
Goat      LS.....Q....................W................F........A....
Human     EDGL..QQ.....RS..........M....................SR...
Rats      -NFTSLKQA.....I................................I.....A...V Cattle    PTYGLQCTGAAPLDSIQSLATYYIECIRQVQPEGNYRIAGYSYGACVAFEMCSQLQAQQN    2328
Goat      ........R..........A............P.....X................S
Human     ........R.......H..A...D.........P..V....................S
Rats      ........Q.......PN..A...D..K......P..V....F.................G Cattle    AGPTNNSLFLFDGSHTFVMAYTQSYRAKLNPGCEAEAEAEAMCFFMQQFTEAEHSRVLEA    2388
Goat      .............................M...............R..M........
Human     PA..H.........P.Y.L..........T.........T..I...V....DM..N.....
Rats      PA.AH.N........Y.L..........T.............I...IK..VD....K....

Cattle    LLPLGDLEARVAATVELIVQSHAGLDRHALSFAARSFYHKLRAAEEYTPRATYHGNVTLL    2448
Goat      ................................R...............Q............
Human     ....KG..E....A.D..IK..Q....QE.........Y......Q..K.K.....M..
Rats      ....KS..D....A.D..TR..QS...RD.....V...Y.....DQ.K.K.K.....I..

Cattle    RAKMGSAYQEGLGADYNLSQVCDGKVSVHIIEGDHRTLLEGSGLESILSIIHSSLAEPRV    2508
Goat      .....G..G....................................................
Human     ...T.G..G.D...............V...................I............
Rats      ...T.GT.G.D..........................R.....IN............

Cattle    SVREG   2513 (SEQ ID NO:1)
Goat      .....   (SEQ ID NO:2)
Human     .....   (SEQ ID NO:3)
Rats      .....   (SEQ ID NO:4)
```

FIG. 3

Genbank Accession number AF285607 Protein (SEQ ID NO:5)

```
MEEVVITGMSGKLPESENLEEFWANLIGGVDMVTDDDRRWKAGL
YGLPRRSGKLKDLSRFDASFFGVHPKQAHNMDPQLRLLLEVTYEAIVDAGINPASIRG
TNTGVWVGVSGSEASEALSRDPETLVGYSMVGCQRAMLANRLSFFFDFKGPSITLDTA
CSSSLLALQRAYQAIQRGECAMAIVGGVNIRLKPNTSVQFMKLGMLSPEGTCKFFDAS
GNGYCRAKAVMAILLTKKSLARRVYATILNAGTNTDGCKEKGVTFPSGEAQEQLISSL
YKPAGLDPETLEYVEAHGTGTKVGDPQELNGIVQALCGTRQSPLRIGSTKSNMGHPEP
ASGLAALAKVLLSLEHGLWAPNLHFHNPNPKIPALQDGRLQVVDRPLPVLGGNVGINS
FGFGGSNVHVILQPNSQPLPPPAPHAALPRLLRASGRTLEGVQGLLELGLQHSQNLAF
VSMLNDIATPSPAAMPFRGYAVLGSQGGSQKVQQVLAGKRPLWFICSGMGTQWRGMGL
SLMRLSRFRDSILRSDEAVKPLGLQVSQLLLSTDEAIFDDMVISFVSLTAIQIALIDL
LTSMGLQPDGIIGHSLGEVACGYADGCISQEEAILSAYWRGQCIKEANIPPGAMAAVG
LTWEECKQRCPPGIVPACHNCIDTVTISGPQASMLEFVQQLKQEGVFAKEVRTGGMAF
HSYFMDAIAPMLLQQLKKVIREPQPRSPRWLSTSIPETQWQESLARTFSAEYNVNNLV
SPVLFQEALWRVPEDAVVLEIAPHALLQAVLKRGLKSSCTIIPLMKKDHRDNLEFFLS
NVGQLYLTGIDVNPNGLFPPVEFPAPRGTPLISPHIKWDHSQTWDVPTAEDFPSGSSS
SSATIYKIDINPESPDHYLVDHCIDGRIIFPGTGYLCLVWKTLARALDQNMEHTPVVF
EDVTLHQAVILPKTGIVLLKVRLLEASCTFEVSENGNLIASGKVYQWEDPNPKLFDNR
YGPDPATPVDPTTAIHLSRGDVYKELQLQGFNYGPYFQGILEASSEGNTGQLLWKDNW
VTFMDTMLQMSILAPSKRSLRLPTRITAIYIHPATHQQKLYTLQDKTQVADVVINRCL
DTTVAGGIYISRIHTSVAPRHQQEQLVPILEKFCFTPHVETGCLAGNLALQEELQLCV
GLAQALQTRVAQQGIKMVVPGLDGAQAPQEAPQQGLPRLLATACQLQLNGNLQMEMGQ
ILAQERALLCDDPLLSGLLNSPALKACVTLALENMTSLKMKVVLAGDGQLYSRIPTLL
NTQPLLELDYTATDRHPQALEAAQAKLQQLDITQGQWDPSDPAPSNLGGANLVVCNYA
LASLGDPATAVGNMVAALKEGGFLLLHTLLRGHPLGETVTFLTCPEPQQGQRHLLSQD
EWERLFAGASLHLVALKKSFYGSVLFLCRRLAPLDSPIFLPVEDTSFQWVDSLKNILA
DSSSRAVWLMAVGCTTSGVVGLVNCLRKEPDGHRIRCVLVSNLNSTSPIPETDPKSLE
LQKVLQSDLVMNVYRDGAWGAFRHFPLEQDKPEEQTEHAFINVLTRGDLSSIRWVCSP
LRHSQPTAPGFQLCTIYYASLNFKRNHAGHGQAVPRRHPRNWASRNCLLGMEFSGRDA
SGKRVMGLVPAEGLATSTLVPQSFLWDVPSNWTLEEAASVPVVYSTAYYALMVRGRMQ
PGETVLIHSGSGGVGQAAIAIALSLGCRVFPLVGSAEKRAYLQSRFPQLNETSFANSR
DTSFEQHVLWHTAGKGADLVLNSLAEEKLQASVRCLAQHGRFLEIGKFDLSKNHPLGM
AIFLKNVTFHGILLDSLFEENNTMWQEVSTLLKAGIRKGVVQPLKRTVFPRTQAEDAF
RYMAQGKHIGKVVIQVREEEQEAVLHGTKPTQMVALCKTFCPAHKSYIITGGLGGFGL
ELAHWLVERGAQKLVLTSRSGIRTGYQARQVHEWRRQGVQVLVSTSDVSTLDGTRSLI
TEAAQLGPVGGIFNLAVVLRDAMLDNQTPEFFQDVNKPKYNGTLNLDRVTREACPELD
YFEVFSSVSCGRGNAGQTNYGFANSTMERICEKRRHDGLPGLAVQWGAIADVGLLMEL
KGTKDKAIGGTLPQRITSCMEVLDLFLNQPHPVLSSFVLAEKATSRGPSGSHQDLVKA
VTHILGIRDLATVNLDSSLSDLGLDSLMGVEVRQMLEREHNLLLSMREIRQLTIHKLQ
EISAQAGTADELTDSTPKFGSPAQSHTQLNLSTLLVNPEGPTLTRLNSVQSSERPLFL
VHPIEGSTTVFHSLATKLSIPTYGLQCTGAAPLDSIQSLATYYIECIRQVQPEGNYRI
AGYSYGACVAFEMCSQLQAQQNAGPTNNSLFLFDGSHTFVMAYTQSYRAKLNPGCEAE
AEAEAMCFFMQQFTEAEHSRVLEALLPLGDLEARVAATVELIVQSHAGLDRHALSFAA
RSFYHKLRAAEEYTPRATYHGNVTLLRAKMGSAYQEGLGADYNLSQVCDGKVSVHIIE
GDHRTLLEGSGLESILSIIHSSLAEPRVSVREG"
```

FIG. 4A

Genbank Accession number AF285607 (SEQ ID NO:6)

```
   1 ccgcggccgt cgcggaaggc ccctgcaggc ctcggagcgt ccccggggtt cccgcactcg
  61 ccccgggaat ttggccggca aggcaggaag gacccggggc gttgcgctgc ggtgaccgac
 121 agtaaccccg cacggggcac cctcggccgg gtcaatgacc gcgcgcggcc cgcgcagagc
 181 ccggggccac ccggcccatc accctatcac ctagcaacgc ccactcgagg ggcgccattg
 241 ggccagcgcg cacgcctcgg gccccgatt ggctccggct gcagagagcc acgcccccgg
 301 cccggctccg ctcagcccgg atgctggccg tcaattcgaa cgcctggggg tccgtctagc
 361 ccccagtgtg gccccagtat gaccccaga gtgacccaag tacgccccgt tccgtttcct
 421 ccgcgcgccg tgcacacgtg gccccgcga tcccgaaggt ggggcggccc cgggaggcgt
 481 ggagcacgga acggaagttg ggggcgggg gtgacaccgt gccccgcccc agagcccccc
 541 gagtccgggg ccccaaccc ggcgccccct gggcgcgccc ccgcgcaggg tcccggctcc
 601 cggcggcgc gcgccgcatc accccactgg cggcggccgg ccttgtcccg gggcgcagcc
 661 ccgacgctca ttggcctggg cggcgcagcc aagctgtcag cccatgtggc gtgtccgcac
 721 ggggacgacc gcggttaaat agcgccggcg cgggcctaga gggagccaga gagacggcag
 781 tagcggcctc tcctccaccg cacactccat cctcgctctc cctcagccgt tcgcacagcc
 841 gcccgcgccc agaccaggta caagcggcca ggccgggccg gggtcggaag ttgcgagtcg
 901 ggaacccggt cctggggcca gactggatcg gggctgggg cgggagcaag gcggccgggc
 961 tcgagcgggc gccgacggcc cgcatcctct ggccttgggt gcgcatggtt cggcgcgctg
1021 atggtgaggg ctcatctcac acagcctgcc ctggtctcgg cgtccgagcc tacggtctgg
1081 atgttcgagc cccacgagac gcccgaggct aggcggcaaa gggccctcgc gccatgccta
1141 agcccagcga ggctgtggtg cggatagcga ggggcggacg cccggaacg ccgcgaacag
1201 ccattttggt cttggactgg gccgggcggc tcggaccct cgagggcctg ttggagcccc
1261 cagccgccac accctcgagg gcctcctttt ccggcttggc cgccgaaccc ctccacccac
1321 ggcatcccca tgcctccggg tgcaggatag ccgtctcggc cgaccggagg gcctgagaag
1381 aggggaggga ggtggatgga ggaggcgcag ggccgtataa ggtcggctcc tccaccacgt
1441 gggctccatt tggagccccc agagttctgg ggggagagcc actcctgccg ggtgcaacct
1501 cacggcggcg cgcgcagttt cgccagcgcc gcagggtct ccacccttt gcctcgtccc
1561 gccggactcc gcgtgaatag caagtagggg gagaacagag cgggcgcttt ctggagaagc
1621 agccgccccg ggagctggtg cttctgggcc ggcaaaggc tctttattca gcgctggggg
1681 aggggctcc ctctgccgga acgccgggcg gatcaggcca cccaaggaag acgctctctc
1741 cactcatact ttcccatgct cagagaaacc ctaaaggccc agtagttgga gagttcacca
1801 gtcatcggcg ccataaggcc ctggagcctt ggtgaaagtt tgcaggacca accttggcct
1861 tgcccacttc ctcaaacagg agccccatcc agggcccaca ggctcagggt agactaggtt
1921 ccccggtgg ggctgggaaa cctggggctg gatggacagg caggctgcac aagtaagcaa
1981 gcgcaagtcc tgaggcctcg acctgtgcaa gatgtgtggg tctgggtagt gcttgcctgg
2041 cagctgagag agtggttctc caggttggag cctgctggag gggccgtaca ggctggggct
2101 ggcccactgt gggacaggga ccaattttc cccagagccc cgccaggcct tggcactgtt
2161 gaggagacca agctgtggtt ctgcctgga gggcagctcg agatactgag cgcagagcca
2221 gctagtccag tgtgggcact tcttaccacc accacatttg ccctgtatcc ttcgcctact
2281 aaattccctg ggctacctct taacaggctg acggccaggc agtcccttcc tcagaagggt
2341 ttgggccctg cctcccacca tggggcccc tcctgagtct cctgcagcag ggctgtggtg
2401 gggtcacccc aggccaaggc caatgcccag agagcccaat gcgaggtgtt ggcaggctgg
2461 accagagtgg ggactcccct ttcccaacca ccagacatac ccttcacaaa acgttccagc
2521 gggtgcacag ccccagagct ggccatgtgg atctttgttg cagggctttc tgagctgctg
2581 ttctcagacc cttgagtggg ccagatggag gagggagttc atgaagccag ggttgggaag
2641 cagctgggtc tccagcgagg ctgtggactg gcagtgctgg ggcccaggct gactggtgtc
2701 cgggccccca tgccacctc cttgcagaga gagcagccat ggaggaggtg gtgatcactg
2761 gcatgtctgg gaagctgcct gagtcggaga acctggagga gttctgggcc aatctcattg
2821 gcggtgtgga catggtgaca gatgatgaca ggcggtggaa ggccggtaag cgagcctggg
2881 gcttccccgc ctacttgaga ggttctttc tcacccttc tgtggacaca attctcttgg
2941 gttaccaggg agggcctgca ctccggtccc actggcagag ccaacagtca cctaaggtga
3001 ggccgtgtta tagcttcttt ctggagacgg taccagaagg ctctgggcta ggggaacgtg
3061 ggacctctgg ccagtgggct agggactgaa ctccagcctg tgggagtctg gagttctctg
3121 ggcatagcct ttgccccttt cacagaccag ggccattgct tagggtggag ccaggcaag
3181 accaggtggg tgaacacctc cagccagcca ctgcctgccc acgtgctgtc ccaggcggtc
3241 agataagaca tcaggctccc ccgggaagct ggtttgactc cctcacgccc agtagattct
3301 cccgcagagc ggctccacct gatctacagg atatgagtca gtgtgcagca gcctggctgg
3361 ccttacctgc aggccgggat ggggccaggc agaaggtctt agccaggtca ggacagtggc
3421 aggtgggagg aggcagcgct gccgctacaa gtgctctgct ctgttctggg cccatcaccc
3481 atgaggttcc ccctgggcca aagggtcccg ttcaaaagtg gccacccat cccagggagc
3541 ttgaagctcc gtgttgcaag ccggactcc ccccagtca atcacttagg gttatgatgt
3601 cctatgactt gatttctcca cctgtgtgtg ttccctagga ctatatggcc tgcctcggcg
3661 gtcaggcaag ctgaaggacc tgtcccggtt tgacgcttcc ttcttcgggg tccacccaa
```

*FIG. 4B-1*

```
3721 gcaggcacac aatatggacc cccagctccg cttgctgctg gaggtcacct acgaggccat
3781 tgtggatgca ggtgggccat ctgggggct gcagagggcc agtccccaag tttcctgctg
3841 cccttcttga aaacctcccct tttgcttct aaaagcatcg tgtgttcata acaaaacatc
3901 cagaacagaa ggtgctgagg agggagcgga gccctgcgct ggggccgacg aggtgcggag
3961 gtgtgggcct caggcagttc aggtttcaca attgcacacc agaggaatcc cagacatgtc
4021 cgtgtcaccc cagtttcctc actccccatt gcatggctga tcttggaggc gagggcagga
4081 caccaggtgc caggcagagc aggaggcagg atctggcccc aggactttca ccctccactc
4141 ccctctgctg ggttgtgcct agccttgtaa aagtgcttca agggcacaga cttgtcccgg
4201 ggacactggg gaacatggaa attgtgctga gtgggagagg gaaggctgtc catggggtg
4261 aggcccctca gcaggtgggc cacagggaa cccaggacct gcctactgcc acctgtggtt
4321 tgcaggcgcg gtaccctggc cttacaggtc tcttgtcttg ccgcagatgc ttagtagccc
4381 ctggggttga cccttgagtg tgccaggtc ctggacaggc cctgcctggg gggagcggcg
4441 gggaggccga ggccttccca ctgcccaggc cccagccgga gaccttggat gctgctctcc
4501 agggcttgc cagtgtccct ccctccttcc caagcctgca cactcggctt ttgtctctct
4561 ctgtcttctt aatcttgggc cggccaaggg caggctgctt tcaggggctc atcagaccct
4621 tgccagcagt accagtgccc aggggagta gcctggggac agtgcttgtc ctctgtcccc
4681 accgtccagc tgtctctggc ctctgcctga cccagagact ggagcccat ctggcacccc
4741 gcctgtcccc cgggccccag ttttcctgtg acctggttat ctgttgtcaa cccctaccgt
4801 gggccagcca ccccactctg gctccactgt ctcttccctg actcccccagc cactctagag
4861 tcaggcgagg tggagcctcc tctcccctgc aacgtaggat cgaaccctcg gttcgatccc
4921 gtggagatgg gaacggcaac ccactccagt attcttgtct ggagaatccc atggacagaa
4981 gagcctggga ggctacagtc catagggttg cagagttgga catgactgaa gcgacttagc
5041 atgcacccag tcaccccagc cagagaggcc aaggggagac gcctcacctc ccagagctca
5101 acagcaggct gggcacagca cagctgcagg tttgacttct gcctcctaca ggcatcaacc
5161 cagcttccat tcggggggacg aacaccggtg tctgggtggg tgtgagtggc tctgaggctt
5221 cagaggctct gagccgagac cctgagaccc tcgtgggcta cagcatggtg ggctgccagc
5281 gtgccatgtt ggccaaccgc ctctccttct tctttgactt caaaggtggg tgcccacaca
5341 gcccttttgt ttctgactcg ggcctgggt gggggaggc ggcagggcg ggatgacagc
5401 tgagacccct ccagactctg accacacctc ccctaggaag gccagcagga acaaggtcct
5461 ggtggtgtgg gttccacgtg gagagcactc agtagagctg tcagagcccc aaggtatagg
5521 gtggggaggc ggtcccacgg ctgcattgtg tccttgcctg cagggcccag catcaccctg
5581 gacacggcat gctcctccag cctgctggcc ctgcagaggg cctaccaggc catccagaga
5641 ggggagtgcg ccatggccat tgtcggcggc gtgaacatcc ggctgaagcc caacacctcg
5701 gtgcagttca tgaagctggg catgcttagc cccgagggca cctgcaagtt tttcgatgca
5761 tcaggtgaga gcagtgggca tgggccccg ggaagtgcct ccacccctcga ttctatccgg
5821 cacaagcccc tgagcccttc cctgagctca tgagcctgaa gtgccctccg ccccagggga
5881 atggctactg ccgtgcaaag gctgtaatgg ccatccttct gaccaagaag tccctggccc
5941 gacgggtgta cgccaccatc ctcaacgctg gcaccaacac ggatgctgc aaagagaaag
6001 gtggaagctg gcctgggca ggcgagggtg gggctacggg tagtcgggcg gggctggggg
6061 tgctgaggcc tggacccgcc cccaggcgtc accttccct ccggagaggc acaggagcag
6121 ctcatcagct ccctgtataa gccggccggg ctggacccgg agaccctgga gtacgttgaa
6181 gccatggca ccggtaccaa ggtgagaccc ctgcctggcc tgctcatat cccacgtccc
6241 acgccagaga agcaccaggg cggggtcctg acctccctga gttccccata ggtgggcgac
6301 cccaggagc taaacggcat cgtgcaagcc ctgtgtggca cccgccagag ccccctgcgg
6361 attgggtcca ccaagtcgaa catgggacat ccggagcccg cctcagggct cgcggcgctg
6421 gccaaggtag gcaggcgagt ctagggccat cttgtccctg cccgtcagc gtcttatagc
6481 ctgctggggg aagggtccct tccggctgtt ctgtgggata tgggtcatac tgaggcccgg
6541 agagcaggcc gccagcatgt ggccagcccc tgcctggttt cacagggcca gacattttac
6601 ccaagcactt gttccccaag gggccagcca gaggagcag aagcaacagg gcagcccgtg
6661 tttccaggct cgctctccct gtggcctcct gaccagctgg tagcttggag gacccaggtc
6721 actactggtt gagcttctga gtatgatggg agcttcctgg tggtctcagc tccctggcc
6781 accatagcca cctgctgca gctcttagct tgggagatgg ggtgggaat ggctgaggag
6841 cctttgtcta gatccacagc caatgaggtt gggaggtggc agggcccag gtgaggccta
6901 gggctgagag gagacagagc atgtggcttg gtcaccaaga ccgctgcatt ggggcaggga
6961 cgagctttgg gggagaatga aattgcttgc agcgggcaag ggcttctggg gtgacacaga
7021 gggtccttag gagggatgt acctgaagcc catcccgacc agcagggca gggagcccag
7081 ggccggccgt cttgttgacc gcgaggcacc cacaggtgct gctgtccctg agcacgggc
7141 tctgggcccc caacctgcac ttccacaacc caaaccccaa gatcccagca ctgcaggatg
7201 ggcggctgca ggtggtggac cggccctgc ccgtcctcgg gggcaacgtg gcatcaact
7261 cctttggctt cggtggctcc aacgtgcacg tcatcctcca gcccaactcc cagccactgc
7321 caccgcctgc cccacatgcc gccctgaccc gtctgctgcg ggcagtggg cgcaccctgc
7381 agggtgtgca gggtctgctg gagctaggcc tccagcacag ccagaacctg gccttcgtga
7441 gcatgctcaa tgacatcgcg accccctccc cagcagccat gcccttccgt ggctacgccg
7501 tgctgggcag ccaggggggc agccagaagg tgcagcaggt gctggccgg aagcgcccac
7561 tctggttcat ctgctccggt gagccccgac ccacccgccc cacctcaggt catccccgag
```

*FIG. 4B-2*

```
 7621 gcccgcatgg gctgggactg cacggcgctg ccctgacatc tccctccggg acaggtatgg
 7681 gcacacagtg gcgcgggatg gggctgagtc tgatgcgtct gagccgcttc cgcgactcca
 7741 tcctgcgctc ggatgaggcc gtgaacctc tgggactgca ggtgtcacag ctgttgttga
 7801 gcacagacga ggccatcttt gatgacatgg tcatctcctt cgtgagcctc actgccatcc
 7861 aggtgtgccc ctggggtctg gggtgagccg gctggcaggg tggtgagcct ggggtccccg
 7921 agactggcat gacccatcct gttcccaccc caccccccaga tcgcgctcat agacctgctg
 7981 acctccatgg gccttcagcc cgacggcata atcgggcact ccctgggtga ggtggcctgt
 8041 ggctatgccg acggctgcat ctctcaggag gaggccatcc tctctgccta ctggagaggc
 8101 cagtgcatca aggaggccaa catcccgccc ggggccatgg cggctgtagg taggcactgc
 8161 cctctgctcc cctgtcgcgc tccaccctg ggcctgaggg tctccatagg aggtggtcat
 8221 ctgtactggc acctttctgt gttggcgctg ggcagaggcc agggcctggg ggcagctcac
 8281 cagccactgt cctcaccgca gggtgagaac aaccctgaca gcctgccccg ctatgccccg
 8341 gatggccttg gagcccggca tacttgccca tgggtgtcag tagaggccag cgtgattttc
 8401 acatgaaccc atggggggga tgctgcagac ggagtgggcc tgctctcact tgggacaggc
 8461 atcggaagga cgcaggagac cacaaaagga cgtgaaaggg gctgttggga gagtgaggcc
 8521 aaagccctct ctggtaggcc aggcgtggga cccgaaactg gctccacctg taggacggta
 8581 ttaatgacac cttcgtctga gaccagacaa cggcagggat gaaactgcct cgtaaaggtg
 8641 ccgctcggca gcttgtcatt agggccaccc gggcagcatt ccccttcctg ggagggctg
 8701 tgtggggtg cctgctcccc atgccacct ttgaggctct cttctgctcc caggcttgac
 8761 ctgggaggag tgtaagcagc gctgcccccc tggcatcgtg cctgcctgcc acaactgcat
 8821 cgacaccgtg accatctcgg gacctcaggt gggcctggg aggcaaggcc tgtccccaa
 8881 gtccccttc accccgcag agcgtgctct gcgcggggag cccggcactg gcccggaccc
 8941 ggactgccgt cagcgccccc gtccctcccc gtctgcgctc ccccaggcc tccatgttgg
 9001 agttcgtgca gcagctgaag caggagggcg tgttcgccaa ggaggtgcgg acgggcggca
 9061 tggcgttcca ctcctacttc atggacgcta tcgcccccat gctgcttcag cagctcaaga
 9121 aggtggtgg ctgtccccgc gctgtgtggc ggggcttctc cctgaggaca ggcggggaag
 9181 gcaggcccca gcttcctnag ctgacccgcc ggccttcgct aggtgatccg ggagcccag
 9241 ccgcgttccc cacgctggct cagcacttcc atccccgaga cccagtggca ggagagcctg
 9301 gcccgcacct tctcggccga gtacaacgtg aacaacctgg tgagcccgt gctgttccag
 9361 gaggcgctgt ggcgcgtgcc cgaggacgcc gtggtgctgg agatcgcacc ccatgcactg
 9421 ctgcaggtac gcgtagtcct gcagggccgg cgggctggcc gggcgcgggg ggctgagcgg
 9481 ggggccagtg ggaactgacc agggggaggc ccagcccgcc tctgcctctg caggccgtcc
 9541 tgaagagagg cctcaagtcc agctgcacca tcatcccct gatgaagaag gaccacaggg
 9601 acaacctaga gttcttcctc agcaacgtgg gccagctcta cctgaccggg tgcggccgct
 9661 ctccctgctc aaccctggga ggctcctccc cagccaggcc accgggcgcc cttgagatgg
 9721 tccccaggaa gcagacctct gggtgctggg ccactttcca caccctggc atgccccca
 9781 ccccaccctg tctcaggcgt ctccaaggtc tttaggggag atggggttgac cgtgggtcaa
 9841 gcagtgggtg ttgcagggca ttcacaaagc tccctttgc accctccagc attgacgtca
 9901 accccaacgg gctgttccca cctgtggagt tcccagctcc ccggggcacc cccctcattt
 9961 cccccacat caagtgggac cacagccaga cctgggatgt gccactgct gaggacttcc
10021 ccagtggctc cagtagctct tctgccacca tctataagat cggtgagtcc ttgcaatgca
10081 ggcgggcagg ggggcgggt ggcttcctcc acagcggtgg cactaaggcc caggccccac
10141 agacatcaac cccgagtccc ctgaccacta tctggtggat cactgcatcg acggtcgcat
10201 catcttcccg ggcactgcct acctgtgcct ggtctggaag acactgccc gagccctgga
10261 ccagaacatg gagcacacgc ctgtagtatt cgaggacgtg acgctgcacc aggctgtcat
10321 cctgccgaag acaggtgagg aaggtggctc aagctatggg gtgggagggc cagctgccga
10381 cccctgcagc tgacctctgc ccctgctgcc cacagggatt gtgctcctga agtgcggct
10441 tctggaagct tcctgtacct ttgaggtgtc tgagaatggc aacctgatcg cgagcggtga
10501 gcaggggccc tggaccgggc tgcagggtcc ctgctgggg tctctggta gaccttagct
10561 accggcttag ccctgccctc actcaggcc ttctgccatc cctgcccaca gggaaggtat
10621 accagtggga agatccccaac cccaagctct tgacaaccg gtatgcccg gaccctgcga
10681 ccccgtgga ccccacaact gccatccacc tgtcccgtgg tgatgtatac aaggagccgc
10741 agctgcaggg cttcaactac ggccctact tccaaggtat ccttgaggcc agctccgaag
10801 gtacgtacaa gggaggtccc actttgtgtt ttggggccaa cccctgctgc ctggtgtgag
10861 ggggccacga gggtccccc caggttgggg cacacagagg agagggccca cggcaggaag
10921 agacctagcc tggccaaaac gacagcccct ttctccccag gcaacacagg ccagctgctc
10981 tggaaggaca actgggtgac cttcatggac accatgctgc agatgtctat cctggccccg
11041 agcaagcaga gcctgcgcct gccacacaag atcaccgcca tctacatcca cccggctacc
11101 caccagcaga gctgtacac gctgcaggac aagacacaag gtccctg ccctggcccca
11161 acacacgtgc ctccccgttc ctaggccctg cccaccctca cccagcgtgt cccacagtg
11221 gccgacgtgg taataaacag gtgtctggac accacggtgg ctggcggcat ctacatctca
11281 aggatccaca cctcggtggc ccccggcat cagcaggagc agctggtgcc catcctggag
11341 aagttctgct tcacaccgca cgtggagact gggtgcctgg ctggaacct ggccctgcag
11401 gaggagctgc aactgtgtgt gggtgagtct tttgcaccca ccaccctcat cccggggccc
11461 agcttccagt tcccgggccc cgttatccca tcatagcctc tcctacgtgt ggggtctacc
```

*FIG. 4B-3*

```
11521  tctgccttcc  ttgtgagtgc  ccctggcttc  ccctacctgg  agctgatttc  ttcagagggg
11581  gcctttggca  gaaaaggtga  cagattttcg  cccttcttgt  cttgtaccac  cagccagttg
11641  cacaggcatt  agaccacctt  ttacccaggg  ctcatgccca  antgagcggt  cgggatggtg
11701  ggggagctgg  gaagggcagc  caggccggca  aagcatggaa  cccatcctct  ggggaaccca
11761  tactctgggg  ctcacacctg  catggggcga  gggctgccct  ttgcccacct  agtgtaccaa
11821  tggtcagtgc  cagtttccag  ccctggagga  ctggacagtc  cactccatcc  ctctatcttc
11881  cgtcagtggg  cagaaccagg  tagtgggttc  tgcttcaagc  agtcactagt  tcctggtcgg
11941  gggagcttca  ggaaccccag  cccagctgag  gctcttccct  gacatgtgac  tctcccctcc
12001  ccagggctgg  cacaggcact  gcagaccagg  gtggcccagc  aggggataaa  gatggtggtt
12061  cctggctgg   atggtgccca  ggctcccag   gaggcccac   agcaaggcct  gcctcggctg
12121  ctggccaccg  cctgccagct  gcaactcaac  gggaacttac  agatggagat  gggccagatc
12181  ctagcccagg  agagagccct  gctgtgtgat  gacccttgc   tcagtgggct  cctcaactcc
12241  ccagcactca  aggcgtgcct  gacacttgcc  ctggagaaca  tgaccagcct  caagatgaag
12301  gtggtgaggt  gggcgtcccg  cgcggccgca  ggcccagtgc  tcaaggactc  agatatcggc
12361  agtcccgaac  ctaaggaggg  gctggggcct  ctcagacgtg  aggtcgccca  actcaagatg
12421  gagctgagac  tgcccagaca  ccgaagggga  aggggcact   gaaggactg   gttccagggg
12481  tgtggtgggc  agggcagcac  tggccaatga  cctctgcaga  atcggtgggt  gggcctttct
12541  gggaaacacc  cagctgaggt  ggggggaacgc ctgcccaggg  gcagctgatc  caagaagcct
12601  attccatccc  aggtgctagc  tggtgacggc  caactgtatt  cccgcatccc  cacgctgctc
12661  aacacccagc  ccctgctgga  gctggactac  acagccactg  accgccaccc  ccaggccctg
12721  gaggctgccc  aggccaaatt  gcagcagctc  gatataaccc  agggccagtg  ggaccccctcg
12781  gacccggccc  ccagcaacct  gggtggggcc  aacctcgtgg  tgtgcaacta  tgccttagcc
12841  agcctcggtg  acccggccac  ggctgtcggt  aatatggtgg  ctgccctcaa  ggagggaggc
12901  ttcctgttgc  tgcacacgct  gctcagagga  cacccccttgg gagagactgt  caccttcctc
12961  acttgccctg  agccacaaca  aggccaacgg  cacctcctga  gccaggtaca  ggcggagccg
13021  ggattggtg   gatggggctg  gggggcggg   accgggaggc  tgcagagccc  tgacccccctc
13081  aactcacagg  atgagtggga  gcgcctgttt  gctggtgcgt  ccctgcacct  ggtggccctg
13141  aagaagtcct  tctacggctc  ggtgctcttc  ctgtgccgcc  ggctggcccc  gcttgacagc
13201  ccaatcttcc  tgcctgtgga  ggacaccagc  ttccagtggg  ttgactccc   gaaggtcagt
13261  ccttcccagc  ccctaccagg  ccaaggctga  cccggcttcc  agtgtcggga  cctggggggaa
13321  ttcccccca   tcaggcaacc  cttcccattg  gtcaaccctt  ccttacatcc  ttctacagaa
13381  catcctggcc  gattcctcct  cccgggccgt  atggctcatg  gctgttggct  gcaccacctc
13441  aggggtcgtg  ggcttggtga  actgtctccg  gaaagagcct  gacgggcacc  ggattcggtg
13501  agatgcccac  tgcgctacgt  gccccttgcc  cccgggaccc  aaccacagcc  tcccctcacc
13561  tgtctggctg  cccacaggtg  cgtcctggtg  tctaacctca  acagcacgtc  ccccatccct
13621  gagacagacc  cgaagtcctt  ggagctgcag  aaggtgctcc  agagtgacct  ggtgatgaat
13681  gtctaccgtg  atggggcctg  gggagcgttc  cgccacttcc  cactggaaca  aggtgatgcc
13741  cccgggactg  ccctgctcct  ccgggttcct  cgcctcccag  ctggggtggac tgaggagagg
13801  gcaagaggac  tctggctgga  agccctgctc  caggccaggg  ccacatgcga  tcctaggggc
13861  tccactttct  gtcacccct   agacaagccc  gaggagcaga  cagagcatgc  cttcataaat
13921  gtcctcaccc  gaggggacct  gtcttccatc  cgctgggtct  gctcccctct  gcgccacagc
13981  cagcccacgg  cccctggctt  ccagctctgc  accatctatt  atgcctccct  caacttcaaa
14041  agaaatcatg  ctggccacgg  gcaagctgtc  ccccgacgcc  atcccaggta  caggcagccc
14101  acggtagggg  gaccagaaca  aagaccccccc ccaccccggg  gccgggcct   gggacgagaa
14161  gggtcctcac  ccaacagtgc  tcaggaacct  ggggaggctcc tcccagtgag gtcaggggct
14221  cactcacccg  ccatctgccc  ccaggaattg  ggcctctcgg  aactgcctgc  taggcatgga
14281  gttctctggc  cgagatgcca  gcgggaagcg  tgtgatgggg  ctggtacccg  ccgaaggcct
14341  ggccacctcc  actctggtgc  ctcagagctt  cctgtgggac  gtgccttcca  actggtgagt
14401  caccagggct  gggacctggg  gcccgacatg  gacgtggctg  ggcatcaggc  cagagctgac
14461  ccctgcactg  tgcccttagg  accctggagg  aggccgcctc  ggtgcccgtt  gtctacagca
14521  cagcctacta  cgcgctgtca  gtccggggc   gcatcgcagcc aggcgagacg  gtgctcattc
14581  actcgggctc  cggcggcgta  ggccaggctg  ccatcgccat  cgccctcagc  ctgggctgcc
14641  gtgttttccc  acttgtgggt  aagcctccaa  cccttccag   agcccaggat  tgtctgcctg
14701  gcagcactgc  taaagcccaa  actcaccagg  tgtgcctctc  tctgccaggg  tcagccgaaa
14761  agcgggcata  cctccagtcc  aggttccccc  agctcaacga  aaccagcttt  gccaactccc
14821  gggacacatc  ctttgagcag  catgtgctgt  ggcacacagc  cgggaacggg  gagtggtccc
14881  catcactcac  cacccaccat  ccgcctgtat  cctcagcccc  ctcctcctcc  catcccccac
14941  tcaccagcca  agctggagga  gacgctggcc  catgctggga  caggtctag   accttcagac
15001  tcatgtcagg  ttggcccgcc  tgtgacctctc actatgggga  cccggcttgc  ccccatccc
15061  aagtgctga   cctggtcctc  aactccctgg  cggaagagaa  gcttcaggcc  agtgtgcggt
15121  gcctggccca  gcacggtcga  ttcctggaaa  ttggcaaatt  tgacctttcc  aaaaaccacc
15181  cctgggtga   gatggggcgg  caggcctggt  gggtggctgg  gtgggcaggg  ggctgttggg
15241  cagagtgggg  gtctgcaggg  tggtaggctg  tgggctatgt  ggtgagcggc  ccccgcctg
15301  cccacctgtc  caggcatggc  catcttcctg  aagaacgtga  cttttccacgg gatcctactg
15361  gactctctct  ttgaagaaaa  caacaccatg  tggcaggaag  tgtcgacact  gctgaaggcg
```

*FIG. 4B-4*

```
15421 ggcatccgga agggtgtggt gcagccctc  aagcgaacag tgttccccag gacccaggcg
15481 gaggacgctt tccgttacat ggcccagggc aaacacatcg gcaaagtggt cattcaggtg
15541 agtgggggc  cctgggggtc tctggcccca gccctggccc ctgcagcagt gcgtgaacag
15601 gggccctgct tgggctgcag gtacgtgagg aagagcagga ggcggtgctg cacgggacca
15661 aacccaccca gatggtggcc ttgtgcaaga ccttctgccc agcccacaag agctacatca
15721 tcactggggg cctggggtgc tttggcctag agctggccca ctggctcgtg gagcgagggg
15781 cccagaagct ggtgctgacc tcccgctctg ggatccgcac aggtgaattg cccgacggtt
15841 gtgcattggg caagaaccttc ttcaaaacc ctttatggtg ctttaaggc  accttaggct
15901 tgggaccaga ccttaatttg ccaatcctct ctcactgtct gtcccacagg ctaccaagcc
15961 aggcaggtcc acgagtggag acgccagggt gtgcaggtcc tggtgtccac cagcgacgtc
16021 agcacactgg atggcacccg gagcctatc  actgaggccg cccagcttgg gcccgtggga
16081 ggcatcttca acctggccgt ggtgaggacg gctttagagg ggctggagcc agctgcccag
16141 ggaagggccc ctcctaagaa gccctccaaa ggcctggggc cgaggcaggt gctaagatcc
16201 cctcacccca ggtcctgaga gatgccatgc tggataacca gacccctgag ttcttccagg
16261 acgtcaacaa gcccaagtac aatggcaccc tgaacttgga caggtgggct cctcccttct
16321 cctctcccgc cttctccctg cacagccctt gcactggtgt ccagagacct ggccatgggc
16381 ctccgctggg gtctgaccac aggtccaggg aaggggaggc ggtttggcgg gtaagcagga
16441 gtcctgggca tgacagccgg ggggctgggg aatccggctg ggggtgactt aagaacccac
16501 agggtgaccc gggaggcatg cccagagctg gactacttcg aggtcttctc ctccgtgagc
16561 tgcggcgtg  gcaatgccgg ccagaccaac tacgggttcg ccaactccac catggagcgc
16621 atatgtgaga agcgtcggca cgacggcctc ccaggtgggc ccacctgcca ctccccgatt
16681 ggtggcgtcc caccctcata actaccccga ctcaccacag cgccactgcc cacccacagg
16741 cctcgccgtg cagtggggtg cgattgctga cgtgggcctc ctcatggagc tgaagggcac
16801 taaagacaaa gccatcggcg ggacgctgcc ccagcgcatc acctcctgca tggaggttct
16861 agacctcttc ctgaaccagc cccacccgt  cctgagcagc tttgtgttgg cagagaaggc
16921 tacatcccgt ggccccagcg gcagccacca ggacctcgtg aaggctgtga ctcacatcct
16981 gggtgaggca agcacccttg ccccccttgc caccggtaga cactcgtctt ccgagtctgg
17041 tctcccaggc tgcaaagggg ggcgtgctgg gcttgctcat ggagggagag gcataggtgg
17101 tctgtgcaaa tttggggtgg ggctgtgggt cccatggtac catctgttca gttcagtcgc
17161 tcagtcttgt ccgactcttt gcgacccgt  gaatcgcagc atgccaggcc tccctgtccg
17221 tcaccaactc ctggagttta ctcaaactca tgtccagggt acaatacccca cccaggaccc
17281 ctcccgcgtt gccaactgag ctgcctgcgc cacccccag  gcatccgtga cttggccacc
17341 gtcaacctgg acagctcgct ttcagacctt ggcctcgact cactcatggg cgtggaggtg
17401 cgccagatgc tggagcgtga gcacaacctg ctgctgtcca tgcgggaaat ccggcagctc
17461 acaatccaca agctgcagga gatttcgcg  caggctggca cagctgatgg taggtatgga
17521 gggggtgtcc ccaaagcagc actgtcccct caggggctctt ggcctccgaa caggtcaggg
17581 cttgtccatc tggccccttc ctgagaggcc tccttgggcg cccagcgccc cccacccatc
17641 tgccctggcc acccgtggcc gacgggtgtg catgtctgtg tgtttgtggc aggggaccct
17701 atggtatcat ccctggtatc tgccctctt  cacagagctg acggactcca cacccaaatt
17761 cggcagccct gcccaatcgc acacccagct gaacctgagc accctgctgg tgaaccccga
17821 gggcccgacc ttgacacggc tcaactcggt gcagagctcc gagcggcccc tgttcctggt
17881 gcaccccatc gagggctcca ccaccgtgtt ccacagcctg gccaccaagc tcagcatccc
17941 cacctatggc ctacagtgta caggaggtat gtcaggggcc tacggggctt gccccaagg
18001 gagttgggga tggcaaggca cctgcagaca agggctaaac ctcatgctgt gcccgcagcg
18061 gcaccccgtg acagcatcca gagcctggcc acctactaca tcgagtgcat caggcaagtg
18121 cagccagagg ggaactaccg catcgctggc tactcctacg gggcctgcgt ggctttcgag
18181 atgtgctcac agctgcaggc ccagcagaac gctggcccca cgaacaacag cctcttcctg
18241 tttgacggct cgcacacctt cgtgatggcc tacactcagg tgagggcggc agcggacggg
18301 agtccgcagg cccagcccct tgtacctgcc actgcaacag ctcttcctcc ctttgcagag
18361 ctaccgggcc aagctgaacc ccggctgcga ggcagaggcc gaggccgagg ccatgtgctt
18421 cttcatgcag cagttcacgg aggcggagca tagtagagtc gacccggcgt ggggcccggc
18481 ctcccgatgc ccccgccccc gccccggcg  ctgctcgctc actgtcctgt cctacaggtg
18541 ctggaggcc  tcctgccct  cgggatctg gaggcgcgtg tggcgccac cgtcgagctg
18601 atcgtgcaga gccacgcggg cctggaccgg cacgcgctca gctttgctgc gcgttccttc
18661 taccacaagc tgcgcgccgc ggaggagtac acgccgcggg ctacctacac cggcaacgtg
18721 acgctgctgc gcgccaagat gggcagcgcc taccaggagg gcctgggcgc cgactacaat
18781 ctgtcccagg tgtgcgacgg caaggtgtct gtacacatca tcgagggcga ccaccgcacg
18841 ctgctggagg gcagcggcct ggagtccatc cttagtatta ttcacagctc cctggccgag
18901 ccgcgcgtca gcgtgcggga gggctaggcc accggccgc  ccccgcctc  ccacctgccg
18961 accctggcac cgcagccccg tgcaggcgc  ccataggacc agcacccgca cgcacacgca
19021 cacagcccac cccgcggctt ccctgcgcga caggcggaga cccgcgccgc cgactcggag
19081 acctgcctgg tctgtgaaga gtcggctgag ccactagccg ggccgagctt ccagaaccgc
19141 acgggctctg ctgcactggt gtggtgttcg gttttctggt tggattctcc tatttattgc
19201 gtcgccatgg ggggcggagg gtggcgaggg gagacgctgg tcggtccacc tgtgaagctg
19261 gcgcacgcgg gagccgggcc cagggcccca tgatgccgga ggtcgcgcgg agcagccctg
```

FIG. 4B-5

```
19321 ggcgctgggc acccacccta tttgtctgtg ttcgtttttc aagaaataag gttcaaattg
19381 ctgcgtgggt tttgaaattt actgtaattg tctgtgtaaa gaaccgtgtc tgtactctgt
19441 ttcattttc acgaacctgg taaagatgtt gtctcccatg attaaatctc tccttcgctc
19501 tggcgtctgg gcatcctttc atcctgcctg ctgatcagct ctgtgagcct ccactgtcct
19561 ggcgcccag ggagtaccac cctctgcttc ccgcaggagt gtgtgtgtgt ggaggggtga
19621 tacctggctc cagaaaacag gctggacacc tccagggaag gggccctcga tcaaggaaac
19681 ttgaccagga ggggacaggt aggcagtctg atgatgggct ggcataattg aggacccccc
19741 cacctagggt agccttgcca
```

*FIG. 4B-6*

SEQUENCE LISTING

<160> NUMBER OF SEQ ID NOS: 14

<210> SEQ ID NO 1
<211> LENGTH: 305
<212> TYPE: PRT
<213> ORGANISM: Bos Taurus

<400> SEQUENCE: 1

Phe Gly Ser Pro Ala Gln Ser His Thr Gln Leu Asn Leu Ser Thr Leu
1               5                   10                  15

Leu Val Asn Pro Glu Gly Pro Thr Leu Thr Arg Leu Asn Ser Val Gln
            20                  25                  30

Ser Ser Glu Arg Pro Leu Phe Leu Val His Pro Ile Glu Gly Ser Thr
        35                  40                  45

Thr Val Phe His Ser Leu Ala Thr Lys Leu Ser Ile Pro Thr Tyr Gly
    50                  55                  60

Leu Gln Cys Thr Gly Ala Ala Pro Leu Asp Ser Ile Gln Ser Leu Ala
65                  70                  75                  80

Thr Tyr Tyr Ile Glu Cys Ile Arg Gln Val Gln Pro Glu Gly Asn Tyr
                85                  90                  95

Arg Ile Ala Gly Tyr Ser Tyr Gly Ala Cys Val Ala Phe Glu Met Cys
            100                 105                 110

Ser Gln Leu Gln Ala Gln Gln Asn Ala Gly Pro Thr Asn Asn Ser Leu
        115                 120                 125

Phe Leu Phe Asp Gly Ser His Thr Phe Val Met Ala Tyr Thr Gln Ser
    130                 135                 140

Tyr Arg Ala Lys Leu Asn Pro Gly Cys Glu Ala Glu Ala Glu Ala Glu
145                 150                 155                 160

Ala Met Cys Phe Phe Met Gln Gln Phe Thr Glu Ala Glu His Ser Arg
                165                 170                 175

Val Leu Glu Ala Leu Leu Pro Leu Gly Asp Leu Glu Ala Arg Val Ala
            180                 185                 190

Ala Thr Val Glu Leu Ile Val Gln Ser His Ala Gly Leu Asp Arg His
        195                 200                 205

Ala Leu Ser Phe Ala Ala Arg Ser Phe Tyr His Lys Leu Arg Ala Ala
    210                 215                 220

Glu Glu Tyr Thr Pro Arg Ala Thr Tyr His Gly Asn Val Thr Leu Leu
225                 230                 235                 240

Arg Ala Lys Met Gly Ser Ala Tyr Gln Glu Gly Leu Gly Ala Asp Tyr
                245                 250                 255

Asn Leu Ser Gln Val Cys Asp Gly Lys Val Ser Val His Ile Ile Glu
            260                 265                 270

Gly Asp His Arg Thr Leu Leu Glu Gly Ser Gly Leu Glu Ser Ile Leu
        275                 280                 285

Ser Ile Ile His Ser Ser Leu Ala Glu Pro Arg Val Ser Val Arg Glu
    290                 295                 300

Gly
305

<210> SEQ ID NO 2
<211> LENGTH: 308
<212> TYPE: PRT
<213> ORGANISM: Capra aegagrus
<220> FEATURE:
<221> NAME/KEY: misc_feature
<222> LOCATION: (104)..(104)

-continued

<223> OTHER INFORMATION: Xaa can be any naturally occurring amino acid

<400> SEQUENCE: 2

```
Leu Ser Asn Phe Gly Ser Pro Gln Gln Ser His Thr Gln Leu Asn Leu
1               5                   10                  15

Ser Thr Leu Leu Val Asn Pro Glu Gly Pro Thr Leu Thr Trp Leu Asn
            20                  25                  30

Ser Val Gln Ser Ser Glu Arg Pro Leu Phe Leu Val His Pro Phe Glu
        35                  40                  45

Gly Ser Thr Thr Val Phe His Ala Leu Ala Thr Lys Leu Ser Ile Pro
    50                  55                  60

Thr Tyr Gly Leu Gln Cys Thr Arg Ala Ala Pro Leu Asp Ser Ile Gln
65              70                  75                  80

Ser Leu Ala Ala Tyr Tyr Ile Glu Cys Ile Arg Gln Val Gln Pro Glu
            85                  90                  95

Gly Pro Tyr Arg Ile Ala Gly Xaa Ser Tyr Gly Ala Cys Val Ala Phe
        100                 105                 110

Glu Met Cys Ser Gln Leu Gln Ala Gln Gln Ser Ala Gly Pro Thr Asn
    115                 120                 125

Asn Ser Leu Phe Leu Phe Asp Gly Ser His Thr Phe Val Met Ala Tyr
130                 135                 140

Thr Gln Ser Tyr Arg Ala Lys Met Asn Pro Gly Cys Glu Ala Glu Ala
145                 150                 155                 160

Glu Ala Glu Ala Met Cys Phe Phe Met Arg Gln Phe Met Glu Ala Glu
            165                 170                 175

His Ser Arg Val Leu Glu Ala Leu Leu Pro Leu Gly Asp Leu Glu Ala
        180                 185                 190

Arg Val Ala Ala Thr Val Glu Leu Ile Val Gln Arg His Ala Gly Leu
    195                 200                 205

Asp Arg His Ala Leu Ser Phe Ala Ala Arg Ser Phe Tyr His Lys Leu
210                 215                 220

Arg Ala Ala Glu Gln Tyr Thr Pro Arg Ala Thr Tyr His Gly Asn Val
225                 230                 235                 240

Thr Leu Leu Arg Ala Lys Met Gly Gly Ala Tyr Gly Glu Gly Leu Gly
            245                 250                 255

Ala Asp Tyr Asn Leu Ser Gln Val Cys Asp Gly Lys Val Ser Val His
        260                 265                 270

Ile Ile Glu Gly Asp His Arg Thr Leu Leu Glu Gly Ser Gly Leu Glu
    275                 280                 285

Ser Ile Leu Ser Ile Ile His Ser Ser Leu Ala Glu Pro Arg Val Ser
290                 295                 300

Val Arg Glu Gly
305
```

<210> SEQ ID NO 3
<211> LENGTH: 309
<212> TYPE: PRT
<213> ORGANISM: Homo sapiens

<400> SEQUENCE: 3

```
Glu Asp Gly Leu Gly Ser Gln Gln Gln Ser His Thr Gln Arg Ser Leu
1               5                   10                  15

Ser Thr Leu Leu Val Asn Pro Glu Gly Met Thr Leu Thr Arg Leu Asn
            20                  25                  30

Ser Val Gln Ser Ser Glu Arg Pro Leu Phe Leu Val His Pro Ile Glu
        35                  40                  45
```

```
Gly Ser Thr Thr Val Phe His Ser Arg Ala Thr Lys Leu Ser Ile Pro
     50                   55                  60

Thr Tyr Gly Leu Gln Cys Thr Arg Ala Ala Pro Leu Asp Ser Ile His
65                   70                  75                  80

Ser Leu Ala Ala Tyr Tyr Ile Asp Cys Ile Arg Gln Val Gln Pro Glu
                 85                  90                  95

Gly Pro Tyr Arg Val Ala Gly Tyr Ser Tyr Gly Ala Cys Val Ala Phe
            100                 105                 110

Glu Met Cys Ser Gln Leu Gln Ala Gln Gln Ser Pro Ala Pro Thr His
        115                 120                 125

Asn Ser Leu Phe Leu Phe Asp Gly Ser Pro Thr Tyr Val Leu Ala Tyr
    130                 135                 140

Thr Gln Ser Tyr Arg Ala Lys Leu Thr Pro Gly Cys Glu Ala Glu Ala
145                 150                 155                 160

Glu Thr Glu Ala Ile Cys Phe Phe Val Gln Gln Phe Thr Asp Met Glu
                165                 170                 175

His Asn Arg Val Leu Glu Ala Leu Leu Pro Leu Lys Gly Leu Glu Glu
            180                 185                 190

Arg Val Ala Ala Val Asp Leu Ile Ile Lys Ser His Gln Gly Leu
        195                 200                 205

Asp Arg Gln Glu Ala Leu Ser Phe Ala Ala Arg Ser Phe Tyr His Lys
    210                 215                 220

Leu Arg Ala Ala Gln Glu Tyr Thr Lys Arg Lys Thr Tyr His Gly Asn
225                 230                 235                 240

Met Thr Leu Leu Arg Ala Lys Thr Gly Gly Ala Tyr Gly Glu Asp Leu
                245                 250                 255

Gly Ala Asp Tyr Asn Leu Ser Gln Val Cys Asp Gly Lys Val Ser Val
            260                 265                 270

His Val Ile Glu Gly Asp His Arg Thr Leu Leu Glu Gly Ser Gly Leu
        275                 280                 285

Glu Ser Ile Ile Ser Ile Ile His Ser Ser Leu Ala Glu Pro Arg Val
    290                 295                 300

Ser Val Arg Glu Gly
305

<210> SEQ ID NO 4
<211> LENGTH: 305
<212> TYPE: PRT
<213> ORGANISM: Rattus rattus

<400> SEQUENCE: 4

Phe Asn Phe Thr Ser Leu Lys Gln Ala Gln Leu Asn Leu Ser Ile Leu
1               5                   10                  15

Leu Val Asn Pro Glu Gly Pro Thr Leu Thr Arg Leu Asn Ser Val Gln
            20                  25                  30

Ser Ser Glu Arg Pro Leu Phe Leu Val His Pro Ile Glu Gly Ser Ile
        35                  40                  45

Thr Val Phe His Ser Leu Ala Ala Lys Leu Ser Val Pro Thr Tyr Gly
    50                  55                  60

Leu Gln Cys Thr Gln Ala Ala Pro Leu Asp Ser Ile Pro Asn Leu Ala
65                  70                  75                  80

Ala Tyr Tyr Ile Asp Cys Ile Lys Gln Val Gln Pro Glu Gly Pro Tyr
                85                  90                  95

Arg Val Ala Gly Tyr Ser Phe Gly Ala Cys Val Ala Phe Glu Met Cys
            100                 105                 110
```

```
Ser Gln Leu Gln Ala Gln Gln Gly Pro Ala Pro Ala His Asn Asn Leu
        115                 120                 125

Phe Leu Phe Asp Gly Ser His Thr Tyr Val Leu Ala Tyr Thr Gln Ser
    130                 135                 140

Tyr Arg Ala Lys Leu Thr Pro Gly Cys Glu Ala Glu Ala Glu Ala Glu
145                 150                 155                 160

Ala Ile Cys Phe Phe Ile Lys Gln Phe Val Asp Ala Glu His Ser Lys
                165                 170                 175

Val Leu Glu Ala Leu Leu Pro Leu Lys Ser Leu Glu Asp Arg Val Ala
                180                 185                 190

Ala Ala Val Asp Leu Ile Thr Arg Ser His Gln Ser Leu Asp Arg Arg
            195                 200                 205

Asp Leu Ser Phe Ala Ala Val Ser Phe Tyr Tyr Lys Leu Arg Ala Ala
        210                 215                 220

Asp Gln Tyr Lys Pro Lys Ala Lys Tyr His Gly Asn Val Ile Leu Leu
225                 230                 235                 240

Arg Ala Lys Thr Gly Gly Thr Tyr Gly Glu Asp Leu Gly Ala Asp Tyr
                245                 250                 255

Asn Leu Ser Gln Val Cys Asp Gly Lys Val Ser Val His Ile Ile Glu
                260                 265                 270

Gly Asp His Arg Thr Leu Leu Glu Gly Arg Gly Leu Glu Ser Ile Ile
            275                 280                 285

Asn Ile Ile His Ser Ser Leu Ala Glu Pro Arg Val Ser Val Arg Glu
        290                 295                 300

Gly
305

<210> SEQ ID NO 5
<211> LENGTH: 2513
<212> TYPE: PRT
<213> ORGANISM: Bos Taurus

<400> SEQUENCE: 5

Met Glu Val Val Ile Thr Gly Met Ser Gly Lys Leu Pro Glu Ser
1               5                   10                  15

Glu Asn Leu Glu Glu Phe Trp Ala Asn Leu Ile Gly Gly Val Asp Met
                20                  25                  30

Val Thr Asp Asp Asp Arg Arg Trp Lys Ala Gly Leu Tyr Gly Leu Pro
            35                  40                  45

Arg Arg Ser Gly Lys Leu Lys Asp Leu Ser Arg Phe Asp Ala Ser Phe
    50                  55                  60

Phe Gly Val His Pro Lys Gln Ala His Asn Met Asp Pro Gln Leu Arg
65                  70                  75                  80

Leu Leu Leu Glu Val Thr Tyr Glu Ala Ile Val Asp Ala Gly Ile Asn
                85                  90                  95

Pro Ala Ser Ile Arg Gly Thr Asn Thr Gly Val Trp Val Gly Val Ser
                100                 105                 110

Gly Ser Glu Ala Ser Glu Ala Leu Ser Arg Asp Pro Glu Thr Leu Val
        115                 120                 125

Gly Tyr Ser Met Val Gly Cys Gln Arg Ala Met Leu Ala Asn Arg Leu
    130                 135                 140

Ser Phe Phe Phe Asp Phe Lys Gly Pro Ser Ile Thr Leu Asp Thr Ala
145                 150                 155                 160

Cys Ser Ser Ser Leu Leu Ala Leu Gln Arg Ala Tyr Gln Ala Ile Gln
                165                 170                 175
```

-continued

```
Arg Gly Glu Cys Ala Met Ala Ile Val Gly Val Asn Ile Arg Leu
            180                 185                 190
Lys Pro Asn Thr Ser Val Gln Phe Met Lys Leu Gly Met Leu Ser Pro
        195                 200             205
Glu Gly Thr Cys Lys Phe Phe Asp Ala Ser Gly Asn Gly Tyr Cys Arg
210                 215                 220
Ala Lys Ala Val Met Ala Ile Leu Leu Thr Lys Lys Ser Leu Ala Arg
225                 230                 235                 240
Arg Val Tyr Ala Thr Ile Leu Asn Ala Gly Thr Asn Thr Asp Gly Cys
                245                 250                 255
Lys Glu Lys Gly Val Thr Phe Pro Ser Gly Glu Ala Gln Glu Gln Leu
            260                 265                 270
Ile Ser Ser Leu Tyr Lys Pro Ala Gly Leu Asp Pro Glu Thr Leu Glu
        275                 280                 285
Tyr Val Glu Ala His Gly Thr Gly Thr Lys Val Gly Asp Pro Gln Glu
    290                 295                 300
Leu Asn Gly Ile Val Gln Ala Leu Cys Gly Thr Arg Gln Ser Pro Leu
305                 310                 315                 320
Arg Ile Gly Ser Thr Lys Ser Asn Met Gly His Pro Glu Pro Ala Ser
                325                 330                 335
Gly Leu Ala Ala Leu Ala Lys Val Leu Leu Ser Leu Glu His Gly Leu
            340                 345                 350
Trp Ala Pro Asn Leu His Phe His Asn Pro Asn Pro Lys Ile Pro Ala
        355                 360                 365
Leu Gln Asp Gly Arg Leu Gln Val Val Asp Arg Pro Leu Pro Val Leu
    370                 375                 380
Gly Gly Asn Val Gly Ile Asn Ser Phe Gly Phe Gly Gly Ser Asn Val
385                 390                 395                 400
His Val Ile Leu Gln Pro Asn Ser Gln Pro Leu Pro Pro Ala Pro
                405                 410                 415
His Ala Ala Leu Pro Arg Leu Leu Arg Ala Ser Gly Arg Thr Leu Glu
            420                 425                 430
Gly Val Gln Gly Leu Leu Glu Leu Gly Leu Gln His Ser Gln Asn Leu
        435                 440                 445
Ala Phe Val Ser Met Leu Asn Asp Ile Ala Thr Pro Ser Pro Ala Ala
    450                 455                 460
Met Pro Phe Arg Gly Tyr Ala Val Leu Gly Ser Gln Gly Gly Ser Gln
465                 470                 475                 480
Lys Val Gln Gln Val Leu Ala Gly Lys Arg Pro Leu Trp Phe Ile Cys
                485                 490                 495
Ser Gly Met Gly Thr Gln Trp Arg Gly Met Gly Leu Ser Leu Met Arg
            500                 505                 510
Leu Ser Arg Phe Arg Asp Ser Ile Leu Arg Ser Asp Glu Ala Val Lys
        515                 520                 525
Pro Leu Gly Leu Gln Val Ser Gln Leu Leu Leu Ser Thr Asp Glu Ala
    530                 535                 540
Ile Phe Asp Asp Met Val Ile Ser Phe Val Ser Leu Thr Ala Ile Gln
545                 550                 555                 560
Ile Ala Leu Ile Asp Leu Leu Thr Ser Met Gly Leu Gln Pro Asp Gly
                565                 570                 575
Ile Ile Gly His Ser Leu Gly Glu Val Ala Cys Gly Tyr Ala Asp Gly
            580                 585                 590
Cys Ile Ser Gln Glu Glu Ala Ile Leu Ser Ala Tyr Trp Arg Gly Gln
```

```
                    595                 600                 605
Cys Ile Lys Glu Ala Asn Ile Pro Pro Gly Ala Met Ala Ala Val Gly
    610                 615                 620

Leu Thr Trp Glu Glu Cys Lys Gln Arg Cys Pro Pro Gly Ile Val Pro
625                 630                 635                 640

Ala Cys His Asn Cys Ile Asp Thr Val Thr Ile Ser Gly Pro Gln Ala
                645                 650                 655

Ser Met Leu Glu Phe Val Gln Gln Leu Lys Gln Glu Gly Val Phe Ala
            660                 665                 670

Lys Glu Val Arg Thr Gly Gly Met Ala Phe His Ser Tyr Phe Met Asp
        675                 680                 685

Ala Ile Ala Pro Met Leu Leu Gln Gln Leu Lys Lys Val Ile Arg Glu
    690                 695                 700

Pro Gln Pro Arg Ser Pro Arg Trp Leu Ser Thr Ser Ile Pro Glu Thr
705                 710                 715                 720

Gln Trp Gln Glu Ser Leu Ala Arg Thr Phe Ser Ala Glu Tyr Asn Val
                725                 730                 735

Asn Asn Leu Val Ser Pro Val Leu Phe Gln Glu Ala Leu Trp Arg Val
            740                 745                 750

Pro Glu Asp Ala Val Val Leu Glu Ile Ala Pro His Ala Leu Leu Gln
        755                 760                 765

Ala Val Leu Lys Arg Gly Leu Lys Ser Ser Cys Thr Ile Ile Pro Leu
    770                 775                 780

Met Lys Lys Asp His Arg Asp Asn Leu Glu Phe Phe Leu Ser Asn Val
785                 790                 795                 800

Gly Gln Leu Tyr Leu Thr Gly Ile Asp Val Asn Pro Asn Gly Leu Phe
                805                 810                 815

Pro Pro Val Glu Phe Pro Ala Pro Arg Gly Thr Pro Leu Ile Ser Pro
            820                 825                 830

His Ile Lys Trp Asp His Ser Gln Thr Trp Asp Val Pro Thr Ala Glu
        835                 840                 845

Asp Phe Pro Ser Gly Ser Ser Ser Ser Ala Thr Ile Tyr Lys Ile
850                 855                 860

Asp Ile Asn Pro Glu Ser Pro Asp His Tyr Leu Val Asp His Cys Ile
865                 870                 875                 880

Asp Gly Arg Ile Ile Phe Pro Gly Thr Gly Tyr Leu Cys Leu Val Trp
                885                 890                 895

Lys Thr Leu Ala Arg Ala Leu Asp Gln Asn Met Glu His Thr Pro Val
            900                 905                 910

Val Phe Glu Asp Val Thr Leu His Gln Ala Val Ile Leu Pro Lys Thr
        915                 920                 925

Gly Ile Val Leu Leu Lys Val Arg Leu Leu Glu Ala Ser Cys Thr Phe
    930                 935                 940

Glu Val Ser Glu Asn Gly Asn Leu Ile Ala Ser Gly Lys Val Tyr Gln
945                 950                 955                 960

Trp Glu Asp Pro Asn Pro Lys Leu Phe Asp Asn Arg Tyr Gly Pro Asp
                965                 970                 975

Pro Ala Thr Pro Val Asp Pro Thr Thr Ala Ile His Leu Ser Arg Gly
            980                 985                 990

Asp Val Tyr Lys Glu Leu Gln Leu Gln Gly Phe Asn Tyr Gly Pro Tyr
        995                 1000                1005

Phe Gln Gly Ile Leu Glu Ala Ser Ser Glu Gly Asn Thr Gly Gln
    1010                1015                1020
```

```
Leu Leu Trp Lys Asp Asn Trp Val Thr Phe Met Asp Thr Met Leu
    1025                1030                1035

Gln Met Ser Ile Leu Ala Pro Ser Lys Arg Ser Leu Arg Leu Pro
    1040                1045                1050

Thr Arg Ile Thr Ala Ile Tyr Ile His Pro Ala Thr His Gln Gln
    1055                1060                1065

Lys Leu Tyr Thr Leu Gln Asp Lys Thr Gln Val Ala Asp Val Val
    1070                1075                1080

Ile Asn Arg Cys Leu Asp Thr Thr Val Ala Gly Gly Ile Tyr Ile
    1085                1090                1095

Ser Arg Ile His Thr Ser Val Ala Pro Arg His Gln Gln Glu Gln
    1100                1105                1110

Leu Val Pro Ile Leu Glu Lys Phe Cys Phe Thr Pro His Val Glu
    1115                1120                1125

Thr Gly Cys Leu Ala Gly Asn Leu Ala Leu Gln Glu Glu Leu Gln
    1130                1135                1140

Leu Cys Val Gly Leu Ala Gln Ala Leu Gln Thr Arg Val Ala Gln
    1145                1150                1155

Gln Gly Ile Lys Met Val Val Pro Gly Leu Asp Gly Ala Gln Ala
    1160                1165                1170

Pro Gln Glu Ala Pro Gln Gln Gly Leu Pro Arg Leu Leu Ala Thr
    1175                1180                1185

Ala Cys Gln Leu Gln Leu Asn Gly Asn Leu Gln Met Glu Met Gly
    1190                1195                1200

Gln Ile Leu Ala Gln Glu Arg Ala Leu Leu Cys Asp Asp Pro Leu
    1205                1210                1215

Leu Ser Gly Leu Leu Asn Ser Pro Ala Leu Lys Ala Cys Val Thr
    1220                1225                1230

Leu Ala Leu Glu Asn Met Thr Ser Leu Lys Met Lys Val Val Leu
    1235                1240                1245

Ala Gly Asp Gly Gln Leu Tyr Ser Arg Ile Pro Thr Leu Leu Asn
    1250                1255                1260

Thr Gln Pro Leu Leu Glu Leu Asp Tyr Thr Ala Thr Asp Arg His
    1265                1270                1275

Pro Gln Ala Leu Glu Ala Ala Gln Ala Lys Leu Gln Gln Leu Asp
    1280                1285                1290

Ile Thr Gln Gly Gln Trp Asp Pro Ser Asp Pro Ala Pro Ser Asn
    1295                1300                1305

Leu Gly Gly Ala Asn Leu Val Val Cys Asn Tyr Ala Leu Ala Ser
    1310                1315                1320

Leu Gly Asp Pro Ala Thr Ala Val Gly Asn Met Val Ala Ala Leu
    1325                1330                1335

Lys Glu Gly Gly Phe Leu Leu Leu His Thr Leu Leu Arg Gly His
    1340                1345                1350

Pro Leu Gly Glu Thr Val Thr Phe Leu Thr Cys Pro Glu Pro Gln
    1355                1360                1365

Gln Gly Gln Arg His Leu Leu Ser Gln Asp Glu Trp Glu Arg Leu
    1370                1375                1380

Phe Ala Gly Ala Ser Leu His Leu Val Ala Leu Lys Lys Ser Phe
    1385                1390                1395

Tyr Gly Ser Val Leu Phe Leu Cys Arg Arg Leu Ala Pro Leu Asp
    1400                1405                1410

Ser Pro Ile Phe Leu Pro Val Glu Asp Thr Ser Phe Gln Trp Val
    1415                1420                1425
```

```
Asp Ser Leu Lys Asn Ile Leu Ala Asp Ser Ser Arg Ala Val
    1430            1435            1440

Trp Leu Met Ala Val Gly Cys Thr Thr Ser Gly Val Val Gly Leu
    1445            1450            1455

Val Asn Cys Leu Arg Lys Glu Pro Asp Gly His Arg Ile Arg Cys
    1460            1465            1470

Val Leu Val Ser Asn Leu Asn Ser Thr Ser Pro Ile Pro Glu Thr
    1475            1480            1485

Asp Pro Lys Ser Leu Glu Leu Gln Lys Val Leu Gln Ser Asp Leu
    1490            1495            1500

Val Met Asn Val Tyr Arg Asp Gly Ala Trp Gly Ala Phe Arg His
    1505            1510            1515

Phe Pro Leu Glu Gln Asp Lys Pro Glu Glu Gln Thr Glu His Ala
    1520            1525            1530

Phe Ile Asn Val Leu Thr Arg Gly Asp Leu Ser Ser Ile Arg Trp
    1535            1540            1545

Val Cys Ser Pro Leu Arg His Ser Gln Pro Thr Ala Pro Gly Phe
    1550            1555            1560

Gln Leu Cys Thr Ile Tyr Tyr Ala Ser Leu Asn Phe Lys Arg Asn
    1565            1570            1575

His Ala Gly His Gly Gln Ala Val Pro Arg Arg His Pro Arg Asn
    1580            1585            1590

Trp Ala Ser Arg Asn Cys Leu Leu Gly Met Glu Phe Ser Gly Arg
    1595            1600            1605

Asp Ala Ser Gly Lys Arg Val Met Gly Leu Val Pro Ala Glu Gly
    1610            1615            1620

Leu Ala Thr Ser Thr Leu Val Pro Gln Ser Phe Leu Trp Asp Val
    1625            1630            1635

Pro Ser Asn Trp Thr Leu Glu Glu Ala Ala Ser Val Pro Val Val
    1640            1645            1650

Tyr Ser Thr Ala Tyr Tyr Ala Leu Met Val Arg Gly Arg Met Gln
    1655            1660            1665

Pro Gly Glu Thr Val Leu Ile His Ser Gly Ser Gly Gly Val Gly
    1670            1675            1680

Gln Ala Ala Ile Ala Ile Ala Leu Ser Leu Gly Cys Arg Val Phe
    1685            1690            1695

Pro Leu Val Gly Ser Ala Glu Lys Arg Ala Tyr Leu Gln Ser Arg
    1700            1705            1710

Phe Pro Gln Leu Asn Glu Thr Ser Phe Ala Asn Ser Arg Asp Thr
    1715            1720            1725

Ser Phe Glu Gln His Val Leu Trp His Thr Ala Gly Lys Gly Ala
    1730            1735            1740

Asp Leu Val Leu Asn Ser Leu Ala Glu Glu Lys Leu Gln Ala Ser
    1745            1750            1755

Val Arg Cys Leu Ala Gln His Gly Arg Phe Leu Glu Ile Gly Lys
    1760            1765            1770

Phe Asp Leu Ser Lys Asn His Pro Leu Gly Met Ala Ile Phe Leu
    1775            1780            1785

Lys Asn Val Thr Phe His Gly Ile Leu Leu Asp Ser Leu Phe Glu
    1790            1795            1800

Glu Asn Asn Thr Met Trp Gln Glu Val Ser Thr Leu Leu Lys Ala
    1805            1810            1815

Gly Ile Arg Lys Gly Val Val Gln Pro Leu Lys Arg Thr Val Phe
```

-continued

```
            1820                1825                1830

Pro Arg Thr Gln Ala Glu Asp Ala Phe Arg Tyr Met Ala Gln Gly
    1835                1840                1845

Lys His Ile Gly Lys Val Val Ile Gln Val Arg Glu Glu Glu Gln
    1850                1855                1860

Glu Ala Val Leu His Gly Thr Lys Pro Thr Gln Met Val Ala Leu
    1865                1870                1875

Cys Lys Thr Phe Cys Pro Ala His Lys Ser Tyr Ile Ile Thr Gly
    1880                1885                1890

Gly Leu Gly Gly Phe Gly Leu Glu Leu Ala His Trp Leu Val Glu
    1895                1900                1905

Arg Gly Ala Gln Lys Leu Val Leu Thr Ser Arg Ser Gly Ile Arg
    1910                1915                1920

Thr Gly Tyr Gln Ala Arg Gln Val His Glu Trp Arg Arg Gln Gly
    1925                1930                1935

Val Gln Val Leu Val Ser Thr Ser Asp Val Ser Thr Leu Asp Gly
    1940                1945                1950

Thr Arg Ser Leu Ile Thr Glu Ala Ala Gln Leu Gly Pro Val Gly
    1955                1960                1965

Gly Ile Phe Asn Leu Ala Val Val Leu Arg Asp Ala Met Leu Asp
    1970                1975                1980

Asn Gln Thr Pro Glu Phe Phe Gln Asp Val Asn Lys Pro Lys Tyr
    1985                1990                1995

Asn Gly Thr Leu Asn Leu Asp Arg Val Thr Arg Glu Ala Cys Pro
    2000                2005                2010

Glu Leu Asp Tyr Phe Glu Val Phe Ser Ser Val Ser Cys Gly Arg
    2015                2020                2025

Gly Asn Ala Gly Gln Thr Asn Tyr Gly Phe Ala Asn Ser Thr Met
    2030                2035                2040

Glu Arg Ile Cys Glu Lys Arg His Asp Gly Leu Pro Gly Leu
    2045                2050                2055

Ala Val Gln Trp Gly Ala Ile Ala Asp Val Gly Leu Leu Met Glu
    2060                2065                2070

Leu Lys Gly Thr Lys Asp Lys Ala Ile Gly Gly Thr Leu Pro Gln
    2075                2080                2085

Arg Ile Thr Ser Cys Met Glu Val Leu Asp Leu Phe Leu Asn Gln
    2090                2095                2100

Pro His Pro Val Leu Ser Ser Phe Val Leu Ala Glu Lys Ala Thr
    2105                2110                2115

Ser Arg Gly Pro Ser Gly Ser His Gln Asp Leu Val Lys Ala Val
    2120                2125                2130

Thr His Ile Leu Gly Ile Arg Asp Leu Ala Thr Val Asn Leu Asp
    2135                2140                2145

Ser Ser Leu Ser Asp Leu Gly Leu Asp Ser Leu Met Gly Val Glu
    2150                2155                2160

Val Arg Gln Met Leu Glu Arg Glu His Asn Leu Leu Ser Met
    2165                2170                2175

Arg Glu Ile Arg Gln Leu Thr Ile His Lys Leu Gln Glu Ile Ser
    2180                2185                2190

Ala Gln Ala Gly Thr Ala Asp Glu Leu Thr Asp Ser Thr Pro Lys
    2195                2200                2205

Phe Gly Ser Pro Ala Gln Ser His Thr Gln Leu Asn Leu Ser Thr
    2210                2215                2220
```

| | | | | | | | | | | |
|---|---|---|---|---|---|---|---|---|---|---|
| Leu | Leu | Val | Asn | Pro | Glu | Gly | Pro | Thr | Leu | Thr | Arg | Leu | Asn | Ser |
| | | | | 2225 | | | 2230 | | | | 2235 | | | |
| Val | Gln | Ser | Ser | Glu | Arg | Pro | Leu | Phe | Leu | Val | His | Pro | Ile | Glu |
| 2240 | | | | | 2245 | | | | | 2250 | | | | |
| Gly | Ser | Thr | Thr | Val | Phe | His | Ser | Leu | Ala | Thr | Lys | Leu | Ser | Ile |
| | 2255 | | | | | 2260 | | | | | 2265 | | | |
| Pro | Thr | Tyr | Gly | Leu | Gln | Cys | Thr | Gly | Ala | Ala | Pro | Leu | Asp | Ser |
| | 2270 | | | | | 2275 | | | | | 2280 | | | |
| Ile | Gln | Ser | Leu | Ala | Thr | Tyr | Tyr | Ile | Glu | Cys | Ile | Arg | Gln | Val |
| 2285 | | | | | 2290 | | | | | 2295 | | | | |
| Gln | Pro | Glu | Gly | Asn | Tyr | Arg | Ile | Ala | Gly | Tyr | Ser | Tyr | Gly | Ala |
| 2300 | | | | | 2305 | | | | | 2310 | | | | |
| Cys | Val | Ala | Phe | Glu | Met | Cys | Ser | Gln | Leu | Gln | Ala | Gln | Gln | Asn |
| 2315 | | | | | 2320 | | | | | 2325 | | | | |
| Ala | Gly | Pro | Thr | Asn | Asn | Ser | Leu | Phe | Leu | Phe | Asp | Gly | Ser | His |
| | 2330 | | | | | 2335 | | | | | 2340 | | | |
| Thr | Phe | Val | Met | Ala | Tyr | Thr | Gln | Ser | Tyr | Arg | Ala | Lys | Leu | Asn |
| | 2345 | | | | | 2350 | | | | | 2355 | | | |
| Pro | Gly | Cys | Glu | Ala | Glu | Ala | Glu | Ala | Met | Cys | Phe | Phe |
| | 2360 | | | | | 2365 | | | | | 2370 | | |
| Met | Gln | Gln | Phe | Thr | Glu | Ala | Glu | His | Ser | Arg | Val | Leu | Glu | Ala |
| | 2375 | | | | | 2380 | | | | | 2385 | | | |
| Leu | Leu | Pro | Leu | Gly | Asp | Leu | Glu | Ala | Arg | Val | Ala | Ala | Thr | Val |
| | 2390 | | | | | 2395 | | | | | 2400 | | | |
| Glu | Leu | Ile | Val | Gln | Ser | His | Ala | Gly | Leu | Asp | Arg | His | Ala | Leu |
| | 2405 | | | | | 2410 | | | | | 2415 | | | |
| Ser | Phe | Ala | Ala | Arg | Ser | Phe | Tyr | His | Lys | Leu | Arg | Ala | Ala | Glu |
| | 2420 | | | | | 2425 | | | | | 2430 | | | |
| Glu | Tyr | Thr | Pro | Arg | Ala | Thr | Tyr | His | Gly | Asn | Val | Thr | Leu | Leu |
| | 2435 | | | | | 2440 | | | | | 2445 | | | |
| Arg | Ala | Lys | Met | Gly | Ser | Ala | Tyr | Gln | Glu | Gly | Leu | Gly | Ala | Asp |
| | 2450 | | | | | 2455 | | | | | 2460 | | | |
| Tyr | Asn | Leu | Ser | Gln | Val | Cys | Asp | Gly | Lys | Val | Ser | Val | His | Ile |
| | 2465 | | | | | 2470 | | | | | 2475 | | | |
| Ile | Glu | Gly | Asp | His | Arg | Thr | Leu | Leu | Glu | Gly | Ser | Gly | Leu | Glu |
| | 2480 | | | | | 2485 | | | | | 2490 | | | |
| Ser | Ile | Leu | Ser | Ile | Ile | His | Ser | Ser | Leu | Ala | Glu | Pro | Arg | Val |
| | 2495 | | | | | 2500 | | | | | 2505 | | | |
| Ser | Val | Arg | Glu | Gly |
| | 2510 | | | |

```
<210> SEQ ID NO 6
<211> LENGTH: 19760
<212> TYPE: DNA
<213> ORGANISM: Bos Taurus
<220> FEATURE:
<221> NAME/KEY: misc_feature
<222> LOCATION: (9198)..(9198)
<223> OTHER INFORMATION: n is a, c, g, or t
<220> FEATURE:
<221> NAME/KEY: misc_feature
<222> LOCATION: (11682)..(11682)
<223> OTHER INFORMATION: n is a, c, g, or t

<400> SEQUENCE: 6
ccgcggccgt cgcggaaggc ccctgcaggc ctcggagcgt ccccggggtt cccgcactcg      60
ccccgggaat ttggccggca aggcaggaag gacccggggc gttgcgctgc ggtgaccgac     120
```

```
agtaaccccg cacggggcac cctcggccgg gtcaatgacc gcgcgcggcc cgcgcagagc    180
ccggggccac ccggcccatc accctatcac ctagcaacgc ccactcgagg ggcgccattg    240
ggccagcgcg cacgcctcgg gcccccgatt ggctccggct gcagagagcc acgccccgg    300
cccggctccg ctcagcccgg atgctggccg tcaattcgaa cgcctggggg tccgtctagc    360
ccccagtgtg gccccagtat gaccccaga gtgacccaag tacgcccgt tccgtttcct    420
ccgcgcgccg tgcacacgtg gccccgcga tcccgaaggt ggggcggccc cgggaggcgt    480
ggagcacgga acggaagttg ggggcgggg gtgacaccgt gccccgcccc agagcccccc    540
gagtccgggg cccccaaccc ggcgccccct gggcgcgccc ccgcgcaggg tcccggctcc    600
cggcggcggc gcgccgcatc accccactgg cggcggcgcg ccttgtcccg gggcgcagcc    660
ccgacgctca ttggcctggg cggcgcagcc aagctgtcag cccatgtggc gtgtccgcac    720
ggggacgacc gcggttaaat agcgccggcg cgggcctaga gggagccaga gagacggcag    780
tagcggcctc cctccaccg cacactccat cctcgctctc cctcagccgt tcgcacagcc    840
gcccgcgccc agaccaggta caagcggcca ggccgggccg gggtcggaag ttgcgagtcg    900
ggaacccggt cctggggcca gactggatcg ggggctgggg cggagcaag gcggccgggc    960
tcgagcgggc gccgacggcc cgcatcctct ggccttgggt gcgcatggtt cggcgcgctg   1020
atggtgaggg ctcatctcac acagcctgcc ctggtctcgg cgtccgagcc tacggtctgg   1080
atgttcgagc cccacgagac gcccgaggct aggcggcaaa gggccctcgc gccatgccta   1140
agcccagcga ggcaggtggg cggatagcga ggggcggacg cccgggaacg ccgcgaacag   1200
ccattttggt cttggactgg gccgggcggc tgcggaccct cgagggcctg ttggagcccc   1260
cagccgccac accctcgagg gcctcctttt ccggcttggc cgccgaaccc ctccacccac   1320
ggcatcccca tgcctccggg tgcaggatag ccgtctcggc cgaccggagg gcctgagaag   1380
agggagggga ggtggatgga ggaggcgcag ggccgtataa ggtcggctcc tccaccacgt   1440
gggctccatt tggagccccc agagttctgg ggggagagcc actcctgccg ggtgcaacct   1500
cacggcggcg cgcgcagttt cgccagcgcc gcagggtgtct ccacccttt gcctcgtccc   1560
gccggactcc gcgtgaatag caagtagggg gagaacagag cgggcgcttt ctggagaagc   1620
agccgccccg ggagctggtg cttctgggcc ggcaaagggc tctttattca gcgctggggg   1680
aggggggctcc ctctgccgga acgccggggc gatcaggcca cccaaggaag acgctctctc   1740
cactcatact ttcccatgct cagagaaacc ctaaaggccc agtagttgga gagttcacca   1800
gtcatcggcg ccataaggcc ctggagcctt ggtgaaagtt tgcaggacca accttggcct   1860
tgcccacttc ctcaaacagg agcccatcc agggcccaca ggctcagggt agactaggtt   1920
cccccggtgg ggctgggaaa cctggggctg atggacagg caggctgcac aagtaagcaa   1980
gcgcaagtcc tgaggcctcg acctgtgcaa gatgtgtggg tctgggtagt gcttgcctgg   2040
cagctgagag agtggttctc caggttggag cctgctggag gggccgtaca ggctggggct   2100
ggcccactgt gggacaggga ccaattttttc cccagagccc cgccaggcct tggcactgtt   2160
gaggagacca agctgtggtt ctggcctgga gggcagctcg agatactgag cgcagagcca   2220
gctagtccag tgtgggcact tcttaccacc accacatttg ccctgtatcc ttcgcctact   2280
aaattccctg gctacctct taacaggctg acggccaggc agtcccttcc tcagaagggt   2340
ttgggccctg cctcccacca tggggccccc tcctgagtct cctgcagcag ggctgtggtg   2400
gggtcacccc aggccaaggc caatgccag agagcccaat gcgaggtgtt ggcaggctgg   2460
accagagtgg ggactcccct ttcccaacca ccagacatac ccttcacaaa acgttccagc   2520
```

```
gggtgcacag cccccagagct ggccatgtgg atctttgttg cagggctttc tgagctgctg    2580
ttctcagacc cttgagtggg ccagatggag gagggagttc atgaagccag ggttgggaag    2640
cagctgggtc tccagcgagg ctgtggactg gcagtgctgg gcccaggct gactggtgtc     2700
cgggccccca tgccaccctc cttgcagaga gagcagccat ggaggaggtg gtgatcactg    2760
gcatgtctgg gaagctgcct gagtcggaga acctggagga gttctgggcc aatctcattg   2820
gcggtgtgga catggtgaca gatgatgaca ggcggtggaa ggccggtaag cgagcctggg    2880
gcttccccgc ctacttgaga ggttcttttc tcacccttc tgtggacaca attctcttgg    2940
gttaccaggg agggcctgca ctccggtccc actggcagag ccaacagtca cctaaggtga    3000
ggccgtgtta tagcttcttt ctggagacgg taccagaagg ctctgggcta ggggaacgtg    3060
ggacctctgg ccagtgggct agggactgaa ctccagcctg tgggagtctg gagttctctg    3120
ggcatagcct ttgccccttt cacagaccag ggccattgct tagggtggag ccagggcaag    3180
accaggtggg tgaacacctc cagccagcca ctgcctgccc acgtgctgtc ccaggcggtc    3240
agataagaca tcaggctccc ccgggaagct ggtttgactc cctcacgccc agtagattct    3300
cccgcagagc ggctccacct gatctacagg atatgagtca gtgtggcaga gcctggctgg    3360
ccttacctgc aggccgggat ggggccaggc agaaggtctt agccaggtca ggacagtggc    3420
aggtgggagg aggcagcgct gccgctacaa gtgctctgct ctgttctggg cccatcaccc    3480
atgaggttcc ccctgggcca aagggtcccg ttcaaaagtg ggccacccat cccagggagc    3540
ttgaagctcc gtgttgcaag ccgggactcc ccccagtca atcacttagg gttatgatgt     3600
cctatgactt gatttctcca cctgtgtgtg ttccctagga ctatatggcc tgcctcggcg    3660
gtcaggcaag ctgaaggacc tgtcccggtt tgacgcttcc ttcttcgggg tccaccccaa    3720
gcaggcacac aatatggacc cccagctccg cttgctgctg gaggtcacct acgaggccat    3780
tgtggatgca ggtgggccat ctgggggct gcagagggcc agtccccaag tttcctgctg     3840
cccttcttga aaacctccct ttttgcttct aaaagcatcg tgtgttcata acaaaacatc    3900
cagaacagaa ggtgctgagg agggagcgga gccctgggct ggggccgacg aggtggggag    3960
gtgtgggcct caggcagttc aggtttcaca attgcacacc agaggaatcc cagacatgtc    4020
cgtgtcaccc cagtttcctc actccccatt gcatggctga tcttggaggc gagggcagga    4080
caccaggtgc caggcagagc aggaggcagg atctggcccc aggactttca ccctccactc    4140
ccctctgctg ggttgtgcct agccttgtaa aagtgcttca agggcacaga cttgtcccgg    4200
ggacactggg gaacatggaa attgtgctga gtgggagagg gaaggctgtc catggggtg    4260
aggcccctca gcaggtgggc cacaggggaa cccaggacct gcctactgcc acctgtggtt    4320
tgcagggcg gtaccctggc cttacaggtc tcttgtcttg ccgcagatgc ttagtagccc    4380
ctggggttga cccttgagtg tgccagggtc ctggacaggc cctgcctggg gggaggggcg    4440
gggaggccga ggccttccca ctgcccaggc ccagccgga gacttggat gctgctctcc     4500
aggggcttgc cagtgtccct ccctccttcc caagcctgca cactcggctt ttgtctctct   4560
ctgtcttctt aatcttgggc cggccaaggg caggctgctt tcagggctc atcagaccct    4620
tgccagcagt accagtgccc aggggaggta gcctgggac agtgcttgtc ctctgtcccc    4680
accgtccagc tgtctctggc ctctgcctga cccagagact ggagcccat ctggcacccc    4740
gcctgtcccc cgggcccag ttttcctgtg acctggttat ctgttgtcaa ccctaccgt    4800
gggccagcca ccccactctg gctccactgt ctcttccctg actccccagc cactctagag    4860
tcaggcgagg tggagcctcc tctcccctgc aacgtaggat cgaaccctgg gttcgatccc    4920
```

```
gtggagatgg gaacggcaac ccactccagt attcttgtct ggagaatccc atggacagaa   4980
gagcctggga ggctacagtc catagggttg cagagttgga catgactgaa gcgacttagc   5040
atgcacccag tcaccccagc cagagaggcc aaggggagac gcctcacctc ccagagctca   5100
acagcaggct gggcacagca cagctgcagg tttgacttct gcctcctaca ggcatcaacc   5160
cagcttccat tcggggacg aacaccggtg tctgggtggg tgtgagtggc tctgaggctt   5220
cagaggctct gagccgagac cctgagaccc tcgtgggcta cagcatggtg ggctgccagc   5280
gtgccatgtt ggccaaccgc ctctccttct tctttgactt caaaggtggg tgcccacaca   5340 gccctttttgt ttctgactcg ggcctggggt gggggaggc ggcaggggcc ggatgacagc   5400 tgagacccctt ccagactctg accacacctc ccctaggaag gccagcagga acaaggtcct   5460
ggtggtgtgg gttccacgtg gagagcactc agtagagctg tcagagcccc aaggtatagg   5520
gtggggaggc ggtcccacgg ctgcattgtg tccttgcctg cagggcccag catcaccctg   5580
gacacggcat gctcctccag cctgctggcc ctgcagaggg cctaccaggc catccagaga   5640
ggggagtgcg ccatggccat tgtcggcggc gtgaacatcc ggctgaagcc caacacctcg   5700
gtgcagttca tgaagctggg catgcttagc cccgagggca cctgcaagtt tttcgatgca   5760
tcaggtgaga gcagtgggca tggggccccg ggaagtgcct ccaccctcga ttctatccgg   5820
cacaagcccc tgagcccttc cctgagctca tgagcctgaa gtgccctccg ccccagggga   5880
atggctactg ccgtgcaaag gctgtaatgg ccatccttct gaccaagaag tccctggccc   5940
gacgggtgta cgccaccatc ctcaacgctg gcaccaacac ggatggctgc aaagagaaag   6000
gtggaagctg gcctggggca ggcgagggtg gggctacggg tagtcgggcg gggctggggg   6060
tgctgaggcc tggaccccgcc cccaggcgtc accttcccct ccggagaggc acaggagcag   6120
ctcatcagct ccctgtataa gccggccggg ctggacccgg agaccctgga gtacgttgaa   6180
gcccatggca ccggtaccaa ggtgagaccc ctgcctggcc ctgctcatat cccacgtccc   6240
acgccagaga agcaccaggg cggggtcctg acctccctga gttccccata ggtgggcgac   6300
ccccaggagc taaacggcat cgtgcaagcc ctgtgtggca cccgccagag cccctgcgg   6360 attgggtcca ccagtcgaa catgggacat ccggagcccg cctcagggct cgcggcgctg   6420
gccaaggtag gcaggcgagt ctagggccat cttgtccctg ccccgtcagc gtcttatagc   6480
ctgctggggg aagggtccct tccggctgtt ctgtgggata tgggtcatac tgaggcccgg   6540
agagcaggcc gccagcatgt ggccagcccc tgcctggttt cacagggcca gacatttac   6600 ccaagcactt gttccccaag gggccagcca gaggagcag aagcaacagg gcagcccgtg   6660
tttccaggct cgctctccct gtggcctcct gaccagctgg tagcttggag acccaggtc    6720 actactggtt gagcttctga gtatgatggg agcttcctgg tggtctcagc tccctgggcc   6780
accatagcca cctgtctgca gctcttagct tgggagatgg ggtggggaat ggctgaggag   6840
cctttgtcta gatccacagc caatgaggct gggaggtggc agggcccag gtgaggccta    6900 gggctgagag gagacagagc atgtggcttg gtcaccaaga ccgctgcatt ggggcaggga   6960 cgagcttttgg gggagaatga aattgcttgc agcgggcaag ggcttctggg gtgacacaga   7020
gggtccttag gaggggatgt acctgaagcc catcccgacc agcagggggca gggagcccag  7080 ggccggccgt cttgttgacc gcgaggcacc cacaggtgct gctgtccctg gagcacgggc   7140
tctgggcccc caacctgcac ttccacaacc caaaccccaa gatcccagca ctgcaggatg   7200
ggcggctgca ggtggtggac cggccccctgc ccgtcctcgg gggcaacgtg ggcatcaact   7260
cctttggctt cggtggctcc aacgtgcacg tcatcctcca gcccaactcc cagccactgc   7320
```

```
caccgcctgc cccacatgcc gccctgcccc gtctgctgcg ggccagtggg cgcaccctgg    7380
agggtgtgca gggtctgctg gagctaggcc tccagcacag ccagaacctg gccttcgtga    7440
gcatgctcaa tgacatcgcg acccccctccc cagcagccat gcccttccgt ggctacgccg    7500
tgctgggcag ccaggggggc agccagaagg tgcagcaggt gctggccggc aagcgcccac    7560
tctggttcat ctgctccggt gagccccgac ccacccgccc cacctcaggt catccccgag    7620
gcccgcatgg gctgggactg cacggcgctg ccctgacatc tccctccggg acaggtatgg    7680
gcacacagtg gcgcgggatg gggctgagtc tgatgcgtct gagccgcttc cgcgactcca    7740
tcctgcgctc ggatgaggcc gtgaagcctc tgggactgca ggtgtcacag ctgttgttga    7800
gcacagacga ggccatcttt gatgacatgg tcatctcctt cgtgagcctc actgccatcc    7860
aggtgtgccc ctggggtctg gggtgagccg gctggcaggg tggtgagcct ggggtccccg    7920
agactggcat gacccatcct gttcccaccc caccccagat cgcgctcat agacctgctg    7980 acctccatgg gccttcagcc cgacggcata atcgggcact ccctgggtga ggtggcctgt    8040
ggctatgccg acggctgcat ctctcaggag gaggccatcc tctctgccta ctggagaggc    8100
cagtgcatca aggaggccaa catcccgccc ggggccatgg cggctgtagg taggcactgc    8160
cctctgctcc cctgtcgcgc tccaccctg ggcctgaggg tctccatagg aggtggtcat    8220
ctgtactggc acctttctgt gttggcgctg ggcagaggcc agggcctggg ggcagctcac    8280
cagccactgt cctcaccgca gggtgagaac aaccctgaca gcctgccccg ctatgccccg    8340
gatggccttg gagcccggca tacttgccca tgggtgtcag tagaggccag cgtgattttc    8400
acatgaaccc atggggggga tgctgcagac ggagtggggcc tgctctcact tgggacaggc    8460
atcggaagga cgcaggagac cacaaaaagga cgtgaaaggg gctgttggga gagtgaggcc    8520
aaagccctct ctggtaggcc aggcgtggga cccgaaactg gctccacctg taggacggta    8580
ttaatgacac cttcgtctga gaccagacaa cggcagggat gaaactgcct cgtaaaggtg    8640
ccgctcggca gcttgtcatt agggccaccc gggcagcatt cccccttcctg gggagggctg    8700 tgtggggggtg cctgctcccc atgccaccct ttgaggctct cttctgctcc caggcttgac    8760
ctgggaggag tgtaagcagc gctgcccccc tggcatcgtg cctgcctgcc acaactgcat    8820
cgacaccgtg accatctcgg gacctcaggt gggccctggg aggcaaggcc tcgtccccaa    8880 gtccccttt c accccgcag agcgtgctct gcgcggggag cccggcactg gcccggaccc    8940
ggactgccgt cagcgccccc gtccctcccc gtctgcgctc ccccaggcc tccatgttgg    9000 agttcgtgca gcagctgaag caggaggcg tgttcgccaa ggaggtgcgg acgggcggca    9060
tggcgttcca ctcctacttc atggacgcta tcgcccccat gctgcttcag cagctcaaga    9120
aggtgggtgt ctgtccccgc gctgtgtggc ggggggcctc cctgaggaca ggcggggaag    9180
gcaggcccca gcttcctnag ctgacccgcc ggccttcgct aggtgatccg ggagcccag    9240 ccgcgttccc cacgctggct cagcacttcc atccccgaga cccagtggca ggagagcctg    9300
gcccgcacct tctcggccga gtacaacgtg aacaacctgg tgagcccgt gctgttccag    9360 gaggcgctgt ggcgcgtgcc cgaggacgcc gtggtgctgg agatcgcacc ccatgcactg    9420
ctgcaggtac gcgtagtcct gcagggccgg cgggctggcc gggcgcgggg ggctgagcgg    9480
ggggccagtg ggaactgacc aggggggaggc ccagcccgcc tctgcctctg caggccgtcc    9540
tgaagagagg cctcaagtcc agctgcacca tcatccccct gatgaagaag gaccacaggg    9600
acaacctaga gttcttcctc agcaacgtgg gccagctcta cctgaccggg tgcggccgct    9660
ctccctgctc aaccctggga ggctcctccc cagccaggcc accgggcggc cttgagatgg    9720
```

```
tccccaggaa gcagacctct gggtgctggg ccactttcca caccottggc atgcccccca    9780
ccccaccctg tctcaggcgt ctccaaggtc tttaggggag atgggttgac cgtgggtcaa    9840
gcagtgggtg ttgcagggca ttcacaaagc tcccttttgc accctccagc attgacgtca    9900
accccaacgg gctgttccca cctgtggagt tcccagctcc ccggggcacc ccctcatttt    9960
cccccacat caagtgggac cacagccaga cctgggatgt gcccactgct gaggacttcc    10020
ccagtggctc cagtagctct tctgccacca tctataagat cggtgagtcc ttgcaatgca    10080
ggcgggcagg ggggcggggt ggcttcctcc acagcggtgg cactaaggcc caggccccac    10140
agacatcaac cccgagtccc ctgaccacta tctggtggat cactgcatcg acggtcgcat    10200
catcttcccg ggcactggct acctgtgcct ggtctggaag acactggccc gagccctgga    10260
ccagaacatg gagcacacgc ctgtagtatt cgaggacgtg acgctgcacc aggctgtcat    10320
cctgccgaag acaggtgagg aaggtggctc aagctatggg gtgggagggc cagctgccga    10380
cccctgcagc tgacctctgc ccctgctgcc cacaggatt gtgctcctga aagtgcggct    10440
tctggaagct tcctgtacct ttgaggtgtc tgagaatggc aacctgatcg cgagcggtga    10500
gcaggggccc tggaccgggc tgcagggtcc ctgctggggg tctctgggta gaccttagct    10560
accggcttag ccctgccctc actcaggccc ttctgccatc cctgcccaca gggaaggtat    10620
accagtggga agatcccaac cccagctct ttgacaaccg gtatggcccg gaccctgcga    10680
cccccgtgga ccccacaact gccatccacc tgtcccgtgg tgatgtatac aaggagctgc    10740
agctgcaggg cttcaactac ggcccctact tccaaggtat ccttgaggcc agctccgaag    10800
gtacgtacaa gggaggtccc actttgtgtt ttggggccaa cccctgctgc ctggtgtgag    10860
ggggccacga ggggtccccc caggttgggg cacacagagg agagggccca cggcaggaag    10920
agacctagcc tggccaaaac gacagcccct ttctccccag gcaacacagg ccagctgctc    10980
tggaaggaca actgggtgac cttcatggac accatgctgc agatgtctat cctggccccg    11040
agcaagcgca gcctgcgcct gcccacacgc atcaccgcca tctacatcca cccggctacc    11100
caccagcaga agctgtacac gctgcaggac aagacacaag gtcagccctg ccctggcccc    11160
acacacgtgc ctccccgttc ctaggccctg cccaccctca cccagcgtgt ccccacagtg    11220
gccgacgtgg taataaacag gtgtctggac accacggtgg ctggcggcat ctacatctca    11280
aggatccaca cctcggtggc ccccgggcat cagcaggagc agctggtgcc catcctggag    11340
aagttctgct tcacaccgca cgtggagact gggtgcctgg ctgggaacct ggccctgcag    11400
gaggagctgc aactgtgtgt gggtgagtct tttgcaccca ccaccctcat cccggggccc    11460
agcttccagt tcccgggccc cgttatccca tcatagcctc tcctacgtgt ggggtctacc    11520
tctgccttcc ttgtgagtgc ccctggcttc ccctacctgg agctgatttc ttcagagggg    11580
gcctttggca gaaaaggtga cagattttcg cccttcttgt cttgtaccac cagccagttg    11640
cacaggcatt agaccacctt ttacccaggg ctcatgccca antgaggggt cgggatggtg    11700
ggggagctgg gaaggcagc caggccggca aagcatggaa cccatcctct ggggaaccca    11760
tactctgggc tcacacctg catggggca gggctgccct ttgcccacct agtgtaccaa    11820
tggtcagtgc cagtttccag ccctggagga ctggacagtc cactccatcc ctctatcttc    11880
cgtcagtggg cagaaccagg tagtgggttc tgcttcaagc agtcactagt tcctggtcgg    11940
gggagcttca ggaaccccag cccagctgag gctcttccct gacatgtgac tctcccctcc    12000
ccagggctgg cacaggcact gcagaccagg gtggcccagc aggggataaa gatggtggtt    12060
cctgggctgg atggtgccca ggctccccag gaggccccac agcaaggcct gcctcggctg    12120
```

```
ctggccaccg cctgccagct gcaactcaac gggaacttac agatggagat gggccagatc   12180
ctagcccagg agagagccct gctgtgtgat gaccccttgc tcagtgggct cctcaactcc   12240
ccagcactca aggcgtgcgt gacacttgcc ctggagaaca tgaccagcct caagatgaag   12300
gtggtgaggt gggcgtcccg cgcggccgca ggcccagtgc tcaaggactc agatatcggc   12360
agtcccgaac ctaagggagg gctggggcct ctcagacgtg aggtcgccca actcaagatg   12420
gagctgagac tgcccagaca ccgaagggga aggggcact gaagggactg gttccagggg    12480
tgtggtgggc agggcagcac tggccaatga cctctgcaga atcggtgggt gggcctttct   12540
gggaaacacc cagctgaggt gggggaacgc ctgcccaggg gcagctgatc caagaagcct   12600
attccatccc aggtgctagc tggtgacggc caactgtatt cccgcatccc cacgctgctc   12660
aacacccagc cctgctggag gctggactac acagccactg accgccaccc caggccctg    12720
gaggctgccc aggccaaatt gcagcagctc gatataaccc agggccagtg gaccctcg     12780
gacccggccc ccagcaacct gggtgggggcc aacctcgtgg tgtgcaacta tgccttagcc  12840
agcctcggtg acccggccac ggctgtcggt aatatggtgg ctgccctcaa ggagggaggc   12900
ttcctgttgc tgcacacgct gctcagagga caccccttgg gagagactgt caccttcctc   12960
acttgccctg agccacaaca aggccaacgg cacctcctga gccaggtaca ggcggagccg   13020
ggattgggtg gatggggctg gggggcggg accgggaggc tgcagagccc tgacccctc    13080
aactcacagg atgagtggga gcgcctgttt gctggtgcgt ccctgcacct ggtggccctg   13140
aagaagtcct tctacggctc ggtgctcttc ctgtgccgcc ggctggcccc gcttgacagc   13200
ccaatcttcc tgcctgtgga ggacaccagc ttccagtggg ttgactccct gaaggtcagt   13260
ccttcccagc ccctaccagg ccaaggctga cccggcttcc agtgtcggga cctgggggaa   13320
ttccccccca tcaggcaacc cttcccattg gtcaacccctt ccttacatcc ttctacagaa  13380
catcctggcc gattcctcct cccggggccgt atggctcatg gctgttggct gcaccacctc  13440
aggggtcgtg ggcttggtga actgtctccg gaaagagcct gacgggcacc ggattcggtg   13500
agatgcccac tgcgctacgt gcccttgcc cccgggaccc aaccacagcc tccctcacc    13560
tgtctggctg cccacaggtg cgtcctggtg tctaacctca acagcacgtc ccccatccct   13620
gagacagacc cgaagtcctt ggagctgcag aaggtgctcc agagtgacct ggtgatgaat   13680
gtctaccgtg atggggcctg gggagcgttc cgccacttcc cactgaaaca aggtgagccc   13740
cccgggactg ccctgctcct ccgggttcct cgcctcccag ctgggtggac tgaggagagg   13800
gcaagaggac tctggctgga agccctgctc caggccaggg ccacatgcga tcctaggggc   13860
tccactttct gtcacccct agacaagccc gaggagcaga cagagcatgc cttcataaat    13920
gtcctcaccc gagggacct gtcttccatc cgctgggtct gctcccctct cgcgcacagc   13980
cagcccacgg ccctggcttt ccagctctgc accatctatt atgcctccct caacttcaaa   14040
agaaatcatg ctggccacgg gcaagctgtc ccccgacgcc atcccaggta caggcagccc   14100
acggtagggg gaccagaaca aagaccccccc ccacccgggg gccggggcct gggacgagaa  14160
gggtcctcac ccaacagtgc tcaggaacct gggaggctcc tcccagtgag gtcagggggct  14220
cactcacccg ccatctgccc ccaggaattg ggcctctcgg aactgcctgc taggcatgga   14280
gttctctggc cgagatgcca gcgggaagcg tgtgatgggg ctggtacccg ccgaaggcct   14340
ggccacctcc actctggtgc ctcagagctt cctgtgggac gtgccttcca actggtgagt   14400
caccagggct gggacctggg gcccgacatg gacgtggctg gcatcaggc cagagctgac   14460
ccctgcactg tgcccttagg accctggagg aggccgcctc ggtgcccgtt gtctacagca   14520
```

```
cagcctacta cgcgctgatg gtccgcgggc gcatgcagcc aggcgagacg gtgctcattc   14580
actcgggctc cggcggcgta ggccaggctg ccatcgccat cgccctcagc ctgggctgcc   14640
gtgttttccc acttgtgggt aagcctccaa cccttcccag agcccaggat tgtctgcctg   14700
gcagcactgc taaagcccaa actcaccagg tgtgcctctc tctgccaggg tcagccgaaa   14760
agcgggcata cctccagtcc aggttccccc agctcaacga aaccagcttt gccaactccc   14820
gggacacatc ctttgagcag catgtgctgt ggcacacagc cgggaagggt gagtggtccc   14880
catcactcac cacccaccat ccgcctgtat cctcagcccc ctcctcctcc catccccac   14940 tcaccagcca agctggagga gacgctgccc catgctggga cagggtctag accttcagac   15000
tcatgtcagg ttggccgggc tgtgaccttc actatgggga cccggcttgc ccccatccc    15060 aaggtgctga cctggtcctc aactccctgg cggaagagaa gcttcaggcc agtgtgcggt   15120
gcctggccca gcacggtcga ttcctggaaa ttggcaaatt tgacctttcc aaaaaccacc   15180
ccctgggtga gatggggcgg caggcctggt gggtggctgg gtgggcaggg ggctgttggg   15240
cagagtgggg gtctgcaggg tggtaggctg tgggctatgt ggtgaggggc ccccgcctg    15300 cccacctgtc caggcatggc catcttcctg aagaacgtga cttccacgg gatcctactg    15360 gactctctct ttgaagaaaa caacaccatg tggcaggaag tgtcgacact gctgaaggcg   15420
ggcatccgga agggtgtggt gcagcccctc aagcgaacag tgttccccag gacccaggcg   15480
gaggacgctt tccgttacat ggcccagggc aaacacatcg gcaaagtggt cattcaggtg   15540 agtgggggc cctgggggtc tctgcccca gccctggccc ctgcagcagt gcgtgaacag     15600
gggccctgct tgggctgcag gtacgtgagg aagagcagga ggcggtgctg cacgggacca   15660
aacccaccca gatggtggcc ttgtgcaaga ccttctgccc agcccacaag agctacatca   15720
tcactggggg cctgggtggc tttggcctag agctggccca ctggctcgtg gagcgagggg   15780
cccagaagct ggtgctgacc tcccgctctg ggatccgcac aggtgaattg cccgacggtt   15840
gtgcattggg caagaaccct cttcaaaacc ctttatggtg ctttaagggc accttaggct   15900
tgggaccaga ccttaatttg ccaatcctct ctcactgtct gtcccacagg ctaccaagcc   15960
aggcaggtcc acgagtggag acgccagggt gtgcaggtcc tggtgtccac cagcgacgtc   16020
agcacactgg atggcacccg gagccttatc actgaggccg cccagcttgg gcccgtggga   16080
ggcatcttca acctggccgt ggtgaggacg gctttagagg ggctggagcc agctgcccag   16140
ggaagggccc ctcctaagaa gccctccaaa ggcctggggc cgaggcaggt gctaagatcc   16200
cctcacccca ggtcctgaga gatgccatgc tggataacca gaccctgag ttcttccagg    16260 acgtcaacaa gcccaagtac aatggcaccc tgaacttgga caggtgggct cctcccttct   16320
cctctcccgc cttctccctg cacagccctt gcactggtgt ccagagacct ggccatgggc   16380
ctccgctggg gtctgaccac aggtccaggg aaggggaggc ggtttggcgg gtaagcagga   16440
gtcctgggca tgacagccgg ggggctgggg aatccggctg ggggtgactt aagaacccac   16500
agggtgaccc gggaggcatg cccagagctg gactacttcg aggtcttctc ctccgtgagc   16560
tgcgggcgtg gcaatgccgg ccagaccaac tacgggttcg ccaactccac catggagcgc   16620
atatgtgaga agcgtcggca cgacggcctc ccaggtgggc ccacctgcca ctccccgatt   16680
ggtgcggtcc cacccctcata actacccga ctcaccacag cgccactgcc cacccacagg    16740
cctcgccgtg cagtggggtg cgattgctga cgtgggcctc ctcatggagc tgaagggcac   16800
taaagacaaa gccatcggcg ggacgctgcc ccagcgcatc acctcctgca tggaggttct   16860
agacctcttc ctgaaccagc cccacccccgt cctgagcagc tttgtgttgg cagagaaggc   16920
```

```
tacatcccgt ggccccagcg gcagccacca ggacctcgtg aaggctgtga ctcacatcct   16980
gggtgaggca agcacccttg cccccttgc caccggtaga cactcgtctt ccgagtctgg    17040
tctcccaggc tgcaaagggg ggcgtgctgg gcttgctcat ggagggagag gcataggtgg   17100
tctgtgcaaa tttgggtggg ggctgtgggt cccatggtac catctgttca gttcagtcgc   17160
tcagtcttgt ccgactcttt gcgaccccgt gaatcgcagc atgccaggcc tccctgtccg   17220
tcaccaactc ctggagttta ctcaaactca tgtccagggt acaataccca cccaggaccc   17280
ctcccgcgtt gccaactgag ctgcctgcgc cacccccag gcatccgtga cttggccacc    17340
gtcaacctgg acagctcgct ttcagacctt ggcctcgact cactcatggg cgtggaggtg   17400
cgccagatgc tggagcgtga gcacaacctg ctgctgtcca tgcgggaaat ccggcagctc   17460
acaatccaca agctgcagga gatttccgcg caggctggca cagctgatgg taggtatgga   17520
gggggtgtcc ccaaagcagc actgtcccct cagggctctt ggcctccgaa caggtcaggg   17580
cttgtccatc tggcccсcttc ctgagaggcc tccttgggcg cccagcgccc cccacccatc   17640
tgccctggcc acccgtggcc gacgggtgtg catgtctgtg tgtttgtggc aggggaccct   17700
atggtatcat ccctggtatc tgcccctctt cacagagctg acggactcca cacccaaatt   17760
cggcagccct gcccaatcgc acacccagct gaacctgagc accctgctgg tgaaccccga   17820
gggcccgacc ttgacacggc tcaactcggt gcagagctcc gagcggcccc tgttcctggt   17880
gcaccccatc gagggctcca ccaccgtgtt ccacagcctg gccaccaagc tcagcatccc   17940
cacctatggc ctacagtgta caggaggtat gtcaggggcc tacggggctt gcccccaagg   18000
gagttgggga tggcaaggca cctgcagaca agggctaaac ctcatgctgt gcccgcagcg   18060
gcacccctgg acagcatcca gagcctggcc acctactaca tcgagtgcat caggcaagtg   18120
cagccagagg ggaactaccg catcgctggc tactcctacg gggcctgcgt ggctttcgag   18180
atgtgctcac agctgcaggc ccagcagaac gctggcccca cgaacaacag cctcttcctg   18240
tttgacggct cgcacacctt cgtgatggcc tacactcagg tgagggcggc agcggacggg   18300
agtccgcagg cccagcccct tgtacctgcc actgcaacag ctcttcctcc ctttgcagag   18360
ctaccgggcc aagctgaacc ccggctgcga ggcagaggcc gaggccgagg ccatgtgctt   18420
cttcatgcag cagttcacgg aggcggagca tagtagagtc gacccggcgt ggggcccggc   18480
ctcccgatgc ccccgccccc gccccggcg ctgctcgctc actgtcctgt cctacaggtg     18540
ctggaggccc tcctgcccct cggggatctg gaggcgcgtg tggcagccac cgtcgagctg   18600
atcgtgcaga gccacgcggg cctggaccgg cacgcgctca gctttgctgc gcgttccttc   18660
taccacaagc tgcgcgccgc ggaggagtac acgccgcggg ctacctacca cggcaacgtg   18720
acgctgctgc gcgccaagat gggcagcgcc taccaggagg gcctgggcgc cgactacaat   18780
ctgtcccagg tgtgcgacgg caaggtgtct gtacacatca tcgagggcga ccaccgcacg   18840
ctgctggagg gcagcggcct ggagtccatc cttagtatta ttcacagctc cctggccgag   18900
ccgcgcgtca gcgtgcggga gggctaggcc accggcccgc cccccgcctc ccacctgccg   18960
accctggcac cgcaccccgc gtgcaggcgc ccataggacc agcaccccca cgcacacgca   19020
cacagcccac cccgcggctt ccctgggcgc agggccgaga cccgcgccgc cgactcggag   19080
acctgcctgg tctgtgaaga gtcggctgag ccactagccg ggccgagctt ccagaaccgc   19140
acgggctctg ctgcactggt gtggtgttcg gttttctggt tggattctcc tatttattgc   19200
gtcgccatgg ggggcggagg gtggcgaggg gagacgctgg tcggtccacc tgtgaagctg   19260
gcgcacgcgg gagccgggcc cagggcccca tgatgccgga ggtcgcgcgg agcagccctg   19320
```

-continued

```
ggcgctgggc acccacccta tttgtctgtg ttcgtttttc aagaaataag gttcaaattg    19380
ctgcgtgggt tttgaaattt actgtaattg tctgtgtaaa gaaccgtgtc tgtactctgt    19440 ttcattttc acgaacctgg taaagatgtt gtctcccatg attaaatctc tccttcgctc     19500
tggcgtctgg gcatcctttc atcctgcctg ctgatcagct ctgtgagcct ccactgtcct    19560
ggcgccccag ggagtaccac cctctgcttc ccgcaggagt gtgtgtgtgt ggaggggtga    19620
tacctggctc cagaaaacag gctggacacc tccaggaagg gggccctcga tcaaggaaac    19680
ttgaccagga ggggacaggt aggcagtctg atgatgggct ggcataattg aggacccccc    19740
cacctagggt agccttgcca                                                19760
```

<210> SEQ ID NO 7
<211> LENGTH: 20
<212> TYPE: DNA
<213> ORGANISM: Bos Taurus

<400> SEQUENCE: 7

```
agagctgacg gactccacac                                                   20
```

<210> SEQ ID NO 8
<211> LENGTH: 20
<212> TYPE: DNA
<213> ORGANISM: Bos Taurus

<400> SEQUENCE: 8

```
ctgcatgaag aagcacatgg                                                   20
```

<210> SEQ ID NO 9
<211> LENGTH: 19
<212> TYPE: DNA
<213> ORGANISM: Bos Taurus

<400> SEQUENCE: 9

```
ctcgcacacc ttcgtgatg                                                    19
```

<210> SEQ ID NO 10
<211> LENGTH: 20
<212> TYPE: DNA
<213> ORGANISM: Bos Taurus

<400> SEQUENCE: 10

```
cacgttgccg tggtaggtag                                                   20
```

<210> SEQ ID NO 11
<211> LENGTH: 20
<212> TYPE: DNA
<213> ORGANISM: Bos Taurus

<400> SEQUENCE: 11

```
cgctcactgt cctgtcctac                                                   20
```

<210> SEQ ID NO 12
<211> LENGTH: 24
<212> TYPE: DNA
<213> ORGANISM: Bos Taurus

<400> SEQUENCE: 12

```
gctgtgaata atactaagga tgga                                              24
```

<210> SEQ ID NO 13
<211> LENGTH: 20
<212> TYPE: DNA

```
<213> ORGANISM: Bos Taurus

<400> SEQUENCE: 13
agagctgacg gactccacac                                                20

<210> SEQ ID NO 14
<211> LENGTH: 20
<212> TYPE: DNA
<213> ORGANISM: Bos Taurus

<400> SEQUENCE: 14
gcctgatgca ctcgatgtag                                                20
```

GENETIC MARKERS IN FATTY ACID SYNTHASE FOR IDENTIFICATION OF MEAT PRODUCT FATTY ACID CONTENT IN CATTLE

CROSS-REFERENCE TO RELATED APPLICATIONS

This application claims priority under 35 U.S.C. §119 of a provisional application Ser. No. 60/951,873 filed Jul. 25, 2007, which application is hereby incorporated by reference in its entirety.

GRANT REFERENCE

This invention was made with government support under Grant numbers 2005-34115-15822 and 2005-35205-16235 awarded by USDA/CREES. The government has certain rights in the invention.

FIELD OF THE INVENTION

The present invention relates to molecular markers for identifying the fatty acid content of meat products from cattle as well as tests for assaying for the same. The invention also relates to identifying genetic loci and mutations thereof which contribute to heritable differences in fatty acid content of beef products.

BACKGROUND OF THE INVENTION

Meat fatty acid composition is of great interest because of its implications for human health. High intake of saturated fatty acids (SFA) can result in elevated plasma cholesterol, which contributes to cardiovascular disease (Bronte-Stewart et al., 1956). Of the SFA, C12:0 (lauric), C14:0, (myristic) and C16:0 (palmitic) are considered to have the most harmful cardiovascular effects (Keys et al., 1974), whereas C18:0 (stearic) is believed to be neutral (Bonanome and Grundy, 1988). In contrast, polyunsaturated fatty acids (PUFA) and MUFA increase hepatic LDL receptor activity, thereby decreasing the circulating concentration of LDL-cholesterol (Woollett et al., 1992; Rudel et al., 1995).

The ruminal microorganisms of beef cattle hydrogenate the majority of dietary unsaturated fatty acids, which results in a higher concentration of saturated fatty acids in beef compared with meat from nonruminant animals. The consumption of beef in the U.S. has decreased from a high of 40.4 kg per capita in 1976 to 29.5 kg per capita in 2003. One of the major concerns that affects beef intake is the high concentration of SFA in beef. For many years, dietitians and health professionals have recommended decreasing or excluding the consumption of foods rich in SFA, such as beef.

Unlike that for nonruminants, the fatty acid composition of beef is much less dependent on the diet. The key lipogenic enzymes in fatty acid synthesis pathways, therefore, play an important role in determination of the fatty acid composition of beef. Fatty acid synthase (FAS) is a multifunctional enzyme complex that catalyzes the synthesis of long-chain SFA. It is a homodimer of two identical subunits that contain seven different catalytic sites, which are β-ketoacyl synthase, malonyl/acetyl transferase, dehydrase, enoyl reductase, β-ketoacyl reductase, acyl carrier protein (ACP), and thioesterase (TE) from N to C terminus. Thioesterase domain in FAS complex is responsible for termination of the fatty acid synthesis and release of newly synthesized SFA, mainly C16:0, (palmitic) by hydrolyzing the acyl-5-phosphopantetheine thioester, which is bound to the preceding ACP domain. Studies have shown that TE has maximal activity for C16-acyl ACP, whereas its specific activity decreases dramatically for chain length longer than C18 or shorter than C16 (Lin and Smith, 1978; Pazirandeh et al., 1989). The TE domain of FAS, therefore, plays an essential role in the determination of the product chain length of FAS. Because the predominant elongation system, which is located in the endoplasmic reticulum (ER) membranes, act on C16 and longer fatty acids (Harwood, 1994), only C16:0 produced by FAS, but not C14:0, can be further elongated and desaturated to form one of the major end product of de novo fatty acid synthesis, C18:1. The product chain length of FAS, therefore, plays a role in determining the fatty acid composition. Therefore, we hypothesized that variation in the TE domain of FAS among individuals would be a candidate for heritable differences in fatty acid composition that might be used to improve the healthfulness of the fatty acid composition of beef while maintaining other positive physical and chemical attributes of the product.

It is an object of the present invention to provide a genetic test for determining the likely fatty acid content of meat animals, primarily bovine.

It is yet another object of the present invention to provide the molecular basis for characterizing and further understanding the fatty acid content in cattle.

It is yet another object of the invention to provide further information for understanding and regulating the role of fatty acid synthase in meat product fatty acid content.

It is yet another object of the present invention to use the above information to identify other mutations in linkage disequilibrium with or that are causative of differences in fatty acid content in specific lines, populations, or breeds of cattle.

Other objects will become apparent from the detailed description of the invention which follows.

BRIEF SUMMARY OF THE INVENTION

In its broadest aspect, the present invention provides a method for detecting the presence in a bovine subject of a genetic marker associated with difference in fatty acid composition of meat products derived from those animals. The method comprises the steps of: providing bovine genetic material, and detecting in the genetic material the presence or absence of at least one genetic marker that is in useful linkage disequilibrium with differences in fatty acid content of meat products or a specific nucleotide polymorphism which causes such differences.

According to the invention the inventors have discovered mutations present in the thioesterase region of the fatty acid synthase gene which is very closely linked to or, most likely is the causal mutation of differences in fatty acid content of beef in American Angus cattle. The SNPs are located in the 3' end of the fatty acid synthase gene and encoded with exons 39-42. The effects of the different mutations were shown to be additive. The information was used to create a genetic test for screening for the mutation in cattle or in prospective parental cattle for use in marker-assisted breeding.

According to the invention, several SNPs were identified that were predictive of animals with less atherogenic saturated fatty acid and more monounsaturated fatty acid content in animals. This provides a method of predicting, breeding, and selecting for beef with improved healthfulness. In one aspect of the invention, the number of alleles at positions was positively correlated with phospholipids, triacylglycerols, and total lipids fatty acid composition.

The invention also provides novel fatty acid synthase protein and coding sequence that relate to differences in fatty acid content of beef and, based upon the conserved nature of this protein, particularly the thioesterase domain within which the polymorphisms were located, is likely to be conserved and predictive in other species, breeds or lines of animals used for meat products. The mutant protein is thought to decrease the hydrolysis activity of the protein on substrate C14-Acyl ACP. The mutant protein allows for the development of in vitro and in vivo models and agents to improve the fatty acid content of meat products to increase the number of monounsaturated fatty acids present in relation to the saturated fatty acids.

In another aspect of the invention, one may use the fatty acid synthase gene to screen for other markers in linkage disequilibrium with the SNPs of the invention to create further tests, to identify other potential beneficial fatty acid content associated mutations in other species of meat animals, lines, populations, or breeds of the same.

BRIEF DESCRIPTION OF THE DRAWINGS

FIG. 3. Amino acid sequence alignment of FAS TE domain of several mammalian species (cattle: SEQ ID NO:1; goat: SEQ ID NO:2; human SEQ ID NO:3; and rats SEQ ID NO:4). The alignment was carried out by using BLAST. The amino acid replacement from threonine to alanine in cattle is shown in bold and underlined. The catalytic residues are bold. The fatty acyl substrate binding sites identified in human FAS TE are underlined.

FIG. 4. Nucleotide (FIG. 4B (SEQ ID NO:6)) and amino acid (FIG. 4A (SEQ ID NO:5)) sequences of bovine FAS from Genbank Accession number AF285607.

DETAILED DESCRIPTION OF THE PREFERRED EMBODIMENT

Figure 1:
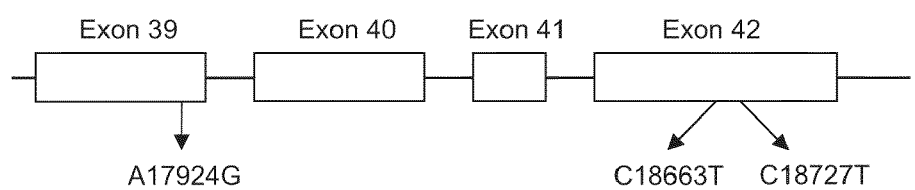
FIG. 1. Schematic illustration of genomic structure of TE domain of FAS gene. The TE domain comprises of 4 exons (exons 39 to 42). The boxes show the exons, and the lines show the introns. The 4 exons contain 231, 222, 99, and 390 nucleotides, respectively. Arrows show the positions of 3 SNPs. The nucleotides substitutions are shown bold. The locations of the SNPs are obtained according to the reference sequence AF285607 from Genbank.

One primary objective of the present invention is to enable the identification of animals with improved fatty acid content of meat for use in breeding and selection. This is achieved by a method that detects the presence of a genetic marker in useful linkage disequilibrium with differences in fatty acid content in a meat animal subject, preferably in a bovine subject. More specifically, the genetic marker may be the bovine fatty acid synthase (FAS) gene.

As used herein, the term a "bovine subject" refers to cattle of any breed. Thus, any of the various cow or ox species, whether male or female, are included in the term, and both adult and new-born animals are intended to be covered. The term does not denote a particular age. One example of a bovine subject is a member of the Holstein-Friesian cattle population.

The term "genetic marker" refers to a variable nucleotide sequence (polymorphic) that is present in bovine genomic DNA on a chromosome and that is identifiable with specific oligonucleotides. Such a variable nucleotide sequence is e.g. distinguishable by nucleic acid amplification and observation of a difference in size or sequence of nucleotides due to the polymorphism. In useful embodiments, such genetic markers may be identified by several techniques known to those skilled in the art, and include typing of microsatellites or short tandem repeats (STR), restriction fragment length polymorphisms (RFLP), detection of deletion or insertion sites, and random amplified polymorphic DNA (RAPD) as well as the typing of single nucleotide polymorphism (SNP) by methods including restriction-fragment-length polymerase chain reaction, allele-specific oligomer hybridization, oligomer-specific ligation assays, mini-sequencing, direct sequencing, fluorescence-detected 5'-exonuclease assays, and hybridization with PNA and LNA probes, single nucleotide primer extension, and others. However, it will be appreciated that other genetic markers and techniques may be applied in accordance with the invention.

The method according to the invention includes the provision of a sample of bovine genetic material. Such bovine genetic (DNA) material may be provided by any conventional method or means. The bovine DNA material may e.g. be extracted, isolated, and purified from blood (e.g., fresh or frozen), tissue samples (e.g., spleen, buccal smears), and hair samples containing follicular cells and semen.

As previously described, the method of the present invention further comprises a step of detecting in the genetic material the presence or absence of a genetic marker that is linked to a bovine meat fatty acid content trait or preferably is the causative mutation.

In order to detect if the genetic marker is present in the genetic material, standard methods well known to persons skilled in the art may be applied, e.g. by the use of nucleic acid amplification. In order to determine if the genetic marker is genetically linked to the fatty acid trait, a lod score can be applied. A lod score, which is also sometimes referred to as $Z_{max}$, indicates the probability (the logarithm of the ratio of the likelihood) that a genetic marker locus and a specific gene locus are linked at a particular distance. Lod scores may e.g. be calculated by applying a computer program such as the MLINK program of the LINKAGE package (Lathrop et al., 1985). A lod score of greater than 3.0 is considered to be significant evidence for linkage between the genetic marker and the fatty acid trait or gene locus.

In one embodiment of the invention, the genetic marker is located in the thioesterase region of the fatty acid synthase gene. This encompasses the 3' region encoded with 4 exons, namely exons 39, 40, 41, and 42. Three SNPs were detected, A17924G, C18663T, and C18727T. The 17924 SNP results in a replacement of threonine (ACC) with a codon for alanine (GCC), which likely results in different activity of the enzyme. The region of the thioesterase region of the FAS gene comprising the genetic markers that are useful in the method of the present invention is indicated in FIG. 1.

Accordingly, genetic markers located on bovine FAS in the thioesterase region, including exons 39, 40, 41, and 42, may be useful according to the present invention. In one specific embodiment, the at least one genetic marker is located in exon 39 and at least two genetic markers are located in exon 42, one of which causes a protein change in the resulting amino acid at a position a few amino acids C-terminal to the substrate binding site.

In a further useful embodiment, three haplotypes have been identified that are associated with improved fatty acid content of beef. Also, the markers identified are additive in effect. For example, the number of G alleles at position 17924 was correlated positively with C18:1 and monounsaturated fatty acid content and negatively with C20:3 content and polyunsaturated fatty acid percentage in phospholipids. The number of C alleles at position 18663 was correlated with greater C18:1 and monounsaturated fatty acid content and lower C20:3 and polyunsaturated fatty acid content in phospholipids. For triacylglycerols, the number of G alleles at position 17924 correlated negatively with C14:0, C15:0, C16:0, and saturated fatty acids and correlated positively with C18:0, monounsaturated fatty acid, and C16:0 to C14:0 ratio.

As described in the examples, at least one genetic marker may be linked to a gene causing the differences in fatty acid content. Thus, in one embodiment, at least one genetic marker is located in the thioesterase region of FAS and genetically linked to the differences in fatty acid content.

It will be appreciated that, in order to detect the specific allele present in a bovine subject of associated with differences in fatty acid content, more than one genetic marker may be applied in accordance with the invention. Thus, at least one marker can be a combination of two or more genetic markers that are shown to be informative whereby the accuracy of the test can be increased.

Genetic markers of the present invention can be made using different methodologies known to those skilled in the art. Thus, it will be understood that, with the knowledge presented herein and the nucleotide sequences of the bovine FAS gene, which are known and publically available, as well as the homology comparisons made in FIG. 3, that additional markers in this gene may be identified and used according to the invention.

Genotyping is based on the analysis of genomic DNA that can be provided by using standard DNA extraction methods as described herein. When the genomic DNA is isolated and purified, nucleic acid amplification (e.g. polymerase chain reaction) can be used to amplify the region of the DNA corresponding to each genetic marker to be used in the analysis for detecting the presence in a bovine subject of a genetic marker associated with muscle fatty acid content.

In another embodiment, the invention comprises a method for identifying genetic markers for fatty acid content in general. Once a major effect gene has been identified, it is expected that other variations present in the same gene, allele or in sequences in useful linkage disequilibrium therewith may be used to identify similar effects on these traits without undue experimentation. The identification of other such genetic variation, once a major effect gene has been discovered, represents no more than routine screening and optimization of parameters well known to those of skill in the art and is intended to be within the scope of this invention. This can include other lines, breeds, or even other meat animals.

The following is a general overview of techniques that can be used to assay for the polymorphisms of the invention.

In the present invention, a sample of genetic material is obtained from an animal. Samples can be obtained from blood, tissue, semen, etc. Generally, peripheral blood cells are used as the source, and the genetic material is DNA. A sufficient amount of cells are obtained to provide a sufficient amount of DNA for analysis. This amount will be known or readily determinable by those skilled in the art. The DNA is isolated from the blood cells by techniques known to those skilled in the art.

Isolation and Amplification of Nucleic Acid

Samples of genomic DNA are isolated from any convenient source including saliva, buccal cells, hair roots, blood, cord blood, amniotic fluid, interstitial fluid, peritoneal fluid, chorionic villus, and any other suitable cell or tissue sample with intact interphase nuclei or metaphase cells. The cells can be obtained from solid tissue as from a fresh or preserved organ or from a tissue sample or biopsy. The sample can contain compounds that are not naturally intermixed with the biological material such as preservatives, anticoagulants, buffers, fixatives, nutrients, antibiotics, or the like.

Methods for isolation of genomic DNA from these various sources are described in, for example, Kirby, *DNA Fingerprinting, An Introduction*, W.H. Freeman & Co. New York (1992). Genomic DNA can also be isolated from cultured primary or secondary cell cultures or from transformed cell lines derived from any of the aforementioned tissue samples.

Samples of animal RNA can also be used. RNA can be isolated from tissues expressing the major effect gene of the invention as described in Sambrook et al., supra. RNA can be total cellular RNA, mRNA, poly A+ RNA, or any combination thereof. For best results, the RNA is purified, but can also be unpurified cytoplasmic RNA. RNA can be reverse transcribed to form DNA, which is then used as the amplification template, so that the PCR indirectly amplifies a specific population of RNA transcripts. See, e.g., Sambrook, supra, Kawasaki et al., Chapter 8 in *PCR Technology*, (1992) supra, and Berg et al., *Hum. Genet.* 85:655-658 (1990).

PCR Amplification

The most common means for amplification is polymerase chain reaction (PCR), as described in U.S. Pat. Nos. 4,683,195, 4,683,202, 4,965,188 each of which is hereby incorporated by reference. If PCR is used to amplify the target regions in blood cells, heparinized whole blood should be drawn in a sealed vacuum tube kept separated from other samples and handled with clean gloves. For best results, blood should be processed immediately after collection; if this is impossible, it should be kept in a sealed container at 4° C. until use. Cells in other physiological fluids may also be assayed. When using any of these fluids, the cells in the fluid should be separated from the fluid component by centrifugation.

Tissues should be roughly minced using a sterile, disposable scalpel and a sterile needle (or two scalpels) in a 5 mm Petri dish. Procedures for removing paraffin from tissue sections are described in a variety of specialized handbooks well known to those skilled in the art.

To amplify a target nucleic acid sequence in a sample by PCR, the sequence must be accessible to the components of the amplification system. One method of isolating target DNA is crude extraction which is useful for relatively large samples. Briefly, mononuclear cells from samples of blood, amniocyte from amniotic fluid, cultured chorionic villus cells, or the like are isolated by layering on sterile Ficoll-Hypaque gradient by standard procedures. Interphase cells are collected and washed three times in sterile phosphate buffered saline before DNA extraction. If testing DNA from peripheral blood lymphocytes, an osmotic shock (treatment of the pellet for 10 sec with distilled water) is suggested, followed by two additional washings if residual red blood cells are visible following the initial washes. This will prevent the inhibitory effect of the heme group carried by hemoglobin on the PCR reaction. If PCR testing is not performed immediately after sample collection, aliquots of $10^6$ cells can be pelleted in sterile Eppendorf tubes and the dry pellet frozen at −20° C. until use.

The cells are resuspended ($10^6$ nucleated cells per 100 μl) in a buffer of 50 mM Tris-HCl (pH 8.3), 50 mM KCl 1.5 mM $MgCl_2$, 0.5% Tween 20, 0.5% NP40 supplemented with 100 μg/ml of proteinase K. After incubating at 56° C. for 2 hr. the cells are heated to 95° C. for 10 min to inactivate the proteinase K and immediately moved to wet ice (snap-cool). If gross aggregates are present, another cycle of digestion in the same buffer should be undertaken. Ten μl of this extract is used for amplification.

When extracting DNA from tissues, e.g., chorionic villus cells or confluent cultured cells, the amount of the above mentioned buffer with proteinase K may vary according to the size of the tissue sample. The extract is incubated for 4-10 hrs at 50°-60° C. and then at 95° C. for 10 minutes to inactivate the proteinase. During longer incubations, fresh proteinase K should be added after about 4 hr at the original concentration.

When the sample contains a small number of cells, extraction may be accomplished by methods as described in Higuchi, "Simple and Rapid Preparation of Samples for PCR", in *PCR Technology*, Ehrlich, H. A. (ed.), Stockton Press, New York, which is incorporated herein by reference. PCR can be employed to amplify target regions in very small numbers of cells (1000-5000) derived from individual colonies from bone marrow and peripheral blood cultures. The cells in the sample are suspended in 20 µl of PCR lysis buffer (10 mM Tris-HCl (pH 8.3), 50 mM KCl, 2.5 mM $MgCl_2$, 0.1 mg/ml gelatin, 0.45% NP40, 0.45% Tween 20) and frozen until use. When PCR is to be performed, 0.6 µl of proteinase K (2 mg/ml) is added to the cells in the PCR lysis buffer. The sample is then heated to about 60° C. and incubated for 1 hr. Digestion is stopped through inactivation of the proteinase K by heating the samples to 95° C. for 10 min and then cooling on ice.

A relatively easy procedure for extracting DNA for PCR is a salting out procedure adapted from the method described by Miller et al., *Nucleic Acids Res.* 16:1215 (1988), which is incorporated herein by reference. Mononuclear cells are separated on a Ficoll-Hypaque gradient. The cells are resuspended in 3 ml of lysis buffer (10 mM Tris-HCl, 400 mM NaCl, 2 mM $Na_2$ EDTA, pH 8.2). Fifty µl of a 20 mg/ml solution of proteinase K and 150 µl of a 20% SDS solution are added to the cells and then incubated at 37° C. overnight. Rocking the tubes during incubation will improve the digestion of the sample. If the proteinase K digestion is incomplete after overnight incubation (fragments are still visible), an additional 50 µl of the 20 mg/ml proteinase K solution is mixed in the solution and incubated for another night at 37° C. on a gently rocking or rotating platform. Following adequate digestion, one ml of a 6 M NaCl solution is added to the sample and vigorously mixed. The resulting solution is centrifuged for 15 minutes at 3000 rpm. The pellet contains the precipitated cellular proteins, while the supernatant contains the DNA. The supernatant is removed to a 15 ml tube that contains 4 ml of isopropanol. The contents of the tube are mixed gently until the water and the alcohol phases have mixed and a white DNA precipitate has formed. The DNA precipitate is removed and dipped in a solution of 70% ethanol and gently mixed. The DNA precipitate is removed from the ethanol and air-dried. The precipitate is placed in distilled water and dissolved.

Kits for the extraction of high-molecular weight DNA for PCR include a Genomic Isolation Kit A.S.A.P. (Boehringer Mannheim, Indianapolis, Ind.), Genomic DNA Isolation System (GIBCO BRL, Gaithersburg, Md.), Elu-Quik DNA Purification Kit (Schleicher & Schuell, Keene, N. H.), DNA Extraction Kit (Stratagene, LaJolla, Calif.), TurboGen Isolation Kit (Invitrogen, San Diego, Calif.), DNeasy Blood & Tissue Kit (Qiagen Inc, Valencia, Calif.), and the like. Use of these kits according to the manufacturer's instructions is generally acceptable for purification of DNA prior to practicing the methods of the present invention.

The concentration and purity of the extracted DNA can be determined by spectrophotometric analysis of the absorbance of a diluted aliquot at 260 nm and 280 nm. After extraction of the DNA, PCR amplification may proceed. The first step of each cycle of the PCR involves the separation of the nucleic acid duplex formed by the primer extension. Once the strands are separated, the next step in PCR involves hybridizing the separated strands with primers that flank the target sequence. The primers are then extended to form complementary copies of the target strands. For successful PCR amplification, the primers are designed so that the position at which each primer hybridizes along a duplex sequence is such that an extension product synthesized from one primer, when separated from the template (complement), serves as a template for the extension of the other primer. The cycle of denaturation, hybridization, and extension is repeated as many times as necessary to obtain the desired amount of amplified nucleic acid.

In a particularly useful embodiment of PCR amplification, strand separation is achieved by heating the reaction to a sufficiently high temperature for a sufficient time to cause the denaturation of the duplex but not to cause an irreversible denaturation of the polymerase (see U.S. Pat. No. 4,965,188, incorporated herein by reference). Typical heat denaturation involves temperatures ranging from about 80° C. to 105° C. for times ranging from seconds to minutes. Strand separation, however, can be accomplished by any suitable denaturing method including physical, chemical, or enzymatic means. Strand separation may be induced by a helicase, for example, or an enzyme capable of exhibiting helicase activity. For example, the enzyme RecA has helicase activity in the presence of ATP. The reaction conditions suitable for strand separation by helicases are known in the art (see Kuhn Hoffman-Berling, 1978, *CSH-Quantitative Biology*, 43:63-67; and Radding, 1982, *Ann. Rev. Genetics* 16:405-436, each of which is incorporated herein by reference).

Template-dependent extension of primers in PCR is catalyzed by a polymerizing agent in the presence of adequate amounts of four deoxyribonucleotide triphosphates (typically dATP, dGTP, dCTP, and dTTP) in a reaction medium comprised of the appropriate salts, metal cations, and pH buffering systems. Suitable polymerizing agents are enzymes known to catalyze template-dependent DNA synthesis. In some cases, the target regions may encode at least a portion of a protein expressed by the cell. In this instance, mRNA may be used for amplification of the target region. Alternatively, PCR can be used to generate a cDNA library from RNA for further amplification, the initial template for primer extension is RNA. Polymerizing agents suitable for synthesizing a complementary, copy-DNA (cDNA) sequence from the RNA template are reverse transcriptase (RT), such as avian myeloblastosis virus RT, Moloney murine leukemia virus RT, or *Thermus thermophilus* (Tth) DNA polymerase, a thermostable DNA polymerase with reverse transcriptase activity marketed by Perkin Elmer Cetus, Inc. Typically, the genomic RNA template is heat degraded during the first denaturation step after the initial reverse transcription step leaving only DNA template. Suitable polymerases for use with a DNA template include, for example, *E. coli* DNA polymerase I or its Klenow fragment, T4 DNA polymerase, Tth polymerase, and Taq polymerase, a heat-stable DNA polymerase isolated from *Thermus aquaticus* and commercially available from Perkin Elmer Cetus, Inc. The latter enzyme is widely used in the amplification and sequencing of nucleic acids. The reaction conditions for using Taq polymerase are known in the art and are described in Gelfand, 1989, *PCR Technology*, supra.

Allele Specific PCR

Allele-specific PCR differentiates between target regions differing in the presence of absence of a variation or polymorphism. PCR amplification primers are chosen that bind only to certain alleles of the target sequence. This method is described by Gibbs, *Nucleic Acid Res.* 17:12427-2448 (1989).

Allele Specific Oligonucleotide Screening Methods

Further diagnostic screening methods employ the allele-specific oligonucleotide (ASO) screening methods, as described by Saiki et al., *Nature* 324:163-166 (1986). Oligonucleotides with one or more base pair mismatches are generated for any particular allele. ASO screening methods detect mismatches between variant target genomic or PCR amplified DNA and non-mutant oligonucleotides, showing decreased binding of the oligonucleotide relative to a mutant oligonucleotide. Oligonucleotide probes can be designed that under low stringency they will bind to both polymorphic forms of the allele, but at high stringency, bind to the allele to which they correspond. Alternatively, stringency conditions can be devised in which an essentially binary response is obtained, i.e., an ASO corresponding to a variant form of the target gene will hybridize to that allele, and not to the wild type allele.

Ligase Mediated Allele Detection Method

Target regions of a test subject's DNA can be compared with target regions in unaffected and affected family members by ligase-mediated allele detection. See Landegren et al., *Science* 241:107-1080 (1988). Ligase may also be used to detect point mutations in the ligation amplification reaction described in Wu et al., *Genomics* 4:560-569 (1989). The ligation amplification reaction (LAR) utilizes amplification of specific DNA sequence using sequential rounds of template dependent ligation as described in Wu, supra, and Barany, *Proc. Nat. Acad. Sci.* 88:189-193 (1990).

Denaturing Gradient Gel Electrophoresis

Amplification products generated using the polymerase chain reaction can be analyzed by the use of denaturing gradient gel electrophoresis. Different alleles can be identified based on the different sequence-dependent melting properties and electrophoretic migration of DNA in solution. DNA molecules melt in segments, termed melting domains, under conditions of increased temperature or denaturation. Each melting domain melts cooperatively at a distinct, base-specific melting temperature (TM). Melting domains are at least 20 base pairs in length, and may be up to several hundred base pairs in length.

Differentiation between alleles based on sequence specific melting domain differences can be assessed using polyacrylamide gel electrophoresis, as described in Chapter 7 of Erlich, ed., *PCR Technology, Principles and Applications for DNA Amplification*, W.H. Freeman and Co., New York (1992), the contents of which are hereby incorporated by reference.

Generally, a target region to be analyzed by denaturing gradient gel electrophoresis is amplified using PCR primers flanking the target region. The amplified PCR product is applied to a polyacrylamide gel with a linear denaturing gradient as described in Myers et al., *Meth. Enzymol.* 155:501-527 (1986), and Myers et al., in *Genomic Analysis, A Practical Approach*, K. Davies Ed. IRL Press Limited, Oxford, pp. 95-139 (1988), the contents of which are hereby incorporated by reference. The electrophoresis system is maintained at a temperature slightly below the Tm of the melting domains of the target sequences.

In an alternative method of denaturing gradient gel electrophoresis, the target sequences may be initially attached to a stretch of GC nucleotides, termed a GC clamp, as described in Chapter 7 of Erlich, supra. Preferably, at least 80% of the nucleotides in the GC clamp are either guanine or cytosine. Preferably, the GC clamp is at least 30 bases long. This method is particularly suited to target sequences with high Tm's.

Generally, the target region is amplified by the polymerase chain reaction as described above. One of the oligonucleotide PCR primers carries at its 5' end, the GC clamp region, at least 30 bases of the GC rich sequence, which is incorporated into the 5' end of the target region during amplification. The resulting amplified target region is run on an electrophoresis gel under denaturing gradient conditions as described above. DNA fragments differing by a single base change will migrate through the gel to different positions, which may be visualized by ethidium bromide staining.

Temperature Gradient Gel Electrophoresis

Temperature gradient gel electrophoresis (TGGE) is based on the same underlying principles as denaturing gradient gel electrophoresis, except the denaturing gradient is produced by differences in temperature instead of differences in the concentration of a chemical denaturant. Standard TGGE utilizes an electrophoresis apparatus with a temperature gradient running along the electrophoresis path. As samples migrate through a gel with a uniform concentration of a chemical denaturant, they encounter increasing temperatures. An alternative method of TGGE, temporal temperature gradient gel electrophoresis (TTGE or tTGGE) uses a steadily increasing temperature of the entire electrophoresis gel to achieve the same result. As the samples migrate through the gel the temperature of the entire gel increases, leading the samples to encounter increasing temperature as they migrate through the gel. Preparation of samples, including PCR amplification with incorporation of a GC clamp, and visualization of products are the same as for denaturing gradient gel electrophoresis.

Single-Strand Conformation Polymorphism Analysis

Target sequences or alleles at an particular locus can be differentiated using single-strand conformation polymorphism analysis, which identifies base differences by alteration in electrophoretic migration of single stranded PCR products, as described in Orita et al., *Proc. Nat. Acad. Sci.* 85:2766-2770 (1989). Amplified PCR products can be generated as described above, and heated or otherwise denatured, to form single stranded amplification products. Single-stranded nucleic acids may refold or form secondary structures which are partially dependent on the base sequence. Thus, electrophoretic mobility of single-stranded amplification products can detect base-sequence difference between alleles or target sequences.

Chemical or Enzymatic Cleavage of Mismatches

Differences between target sequences can also be detected by differential chemical cleavage of mismatched base pairs, as described in Grompe et al., *Am. J. Hum. Genet.* 48:212-222 (1991). In another method, differences between target sequences can be detected by enzymatic cleavage of mismatched base pairs, as described in Nelson et al., *Nature Genetics* 4:11-18 (1993). Briefly, genetic material from an animal and an affected family member may be used to generate mismatch free heterohybrid DNA duplexes. As used herein, "heterohybrid" means a DNA duplex strand comprising one strand of DNA from one animal, and a second DNA strand from another animal, usually an animal differing in the phenotype for the trait of interest. Positive selection for heterohybrids free of mismatches allows determination of small insertions, deletions or other polymorphisms that may be associated with polymorphisms.

Non-Gel Systems

Other possible techniques include non-gel systems such as TaqMan™ (Perkin Elmer). In this system oligonucleotide PCR primers are designed that flank the mutation in question and allow PCR amplification of the region. A third oligonucleotide probe is then designed to hybridize to the region containing the base subject to change between different alleles of the gene. This probe is labeled with fluorescent dyes at both the 5' and 3' ends. These dyes are chosen such that while in this proximity to each other the fluorescence of one of them is quenched by the other and cannot be detected. Extension by Taq DNA polymerase from the PCR primer positioned 5' on the template relative to the probe leads to the cleavage of the dye attached to the 5' end of the annealed probe through the 5' nuclease activity of the Taq DNA polymerase. This removes the quenching effect allowing detection of the fluorescence from the dye at the 3' end of the probe. The discrimination between different DNA sequences arises through the fact that if the hybridization of the probe to the template molecule is not complete, i.e. there is a mismatch of some form; the cleavage of the dye does not take place. Thus only if the nucleotide sequence of the oligonucleotide probe is completely complimentary to the template molecule to which it is bound will quenching be removed. A reaction mix can contain two different probe sequences each designed against different alleles that might be present thus allowing the detection of both alleles in one reaction.

Yet another technique includes an Invader Assay which includes isothermic amplification that relies on a catalytic release of fluorescence. See Invader technology available from Third Wave Technology.

Non-PCR Based DNA Diagnostics

The identification of a DNA sequence linked to an allele sequence can be made without an amplification step, based on polymorphisms including restriction fragment length polymorphisms in an animal and a family member. Hybridization probes are generally oligonucleotides which bind through complementary base pairing to all or part of a target nucleic acid. Probes typically bind target sequences lacking complete complementarity with the probe sequence depending on the stringency of the hybridization conditions. The probes are preferably labeled directly or indirectly, such that by assaying for the presence or absence of the probe, one can detect the presence or absence of the target sequence. Direct labeling methods include radioisotope labeling, such as with 32P or 35S. Indirect labeling methods include fluorescent tags, biotin complexes which may be bound to avidin or streptavidin, or peptide or protein tags. Visual detection methods include photoluminescents, Texas red, rhodamine and its derivatives, red leuco dye and 3,3',5,5'-tetramethylbenzidine (TMB), fluorescein, and its derivatives, dansyl, umbelliferone and the like or with horse radish peroxidase, alkaline phosphatase and the like.

Hybridization probes include any nucleotide sequence capable of hybridizing to a bovine chromosome where one of the major effect genes resides, and thus defining a genetic marker linked to one of the major effect genes, including a restriction fragment length polymorphism, a hypervariable region, repetitive element, or a variable number tandem repeat. Hybridization probes can be any gene or a suitable analog. Further suitable hybridization probes include exon fragments or portions of cDNAs or genes known to map to the relevant region of the chromosome.

Preferred tandem repeat hybridization probes for use according to the present invention are those that recognize a small number of fragments at a specific locus at high stringency hybridization conditions, or that recognize a larger number of fragments at that locus when the stringency conditions are lowered.

One or more additional restriction enzymes and/or probes and/or primers can be used. Additional enzymes, constructed probes, and primers can be determined by routine experimentation by those of ordinary skill in the art and are intended to be within the scope of the invention.

Although the methods described herein may be in terms of the use of a single restriction enzyme and a single set of primers, the methods are not so limited. One or more additional restriction enzymes and/or probes and/or primers can be used, if desired. Indeed in some situations it may be preferable to use combinations of markers giving specific haplotypes. Additional enzymes, constructed probes and primers can be determined through routine experimentation, combined with the teachings provided and incorporated herein.

According to one embodiment of the invention, polymorphisms in a major effect gene has been identified which have an association with fatty acid content. The presence or absence of the markers, in one embodiment may be assayed by PCR RFLP analysis using if needed, restriction endonucleases, and amplification primers which may be designed using analogous human, pig or other of the sequences due to the high homology in the region surrounding the polymorphisms, or may be designed using known sequences (for example, human) as exemplified in GenBank or even designed from sequences obtained from linkage data from closely surrounding genes based upon the teachings and references herein. The sequences surrounding the polymorphism will facilitate the development of alternate PCR tests in which a primer of about 4-30 contiguous bases taken from the sequence immediately adjacent to the polymorphism is used in connection with a polymerase chain reaction to greatly amplify the region before treatment with the desired restriction enzyme. The primers need not be the exact complement; substantially equivalent sequences are acceptable. The design of primers for amplification by PCR is known to those of skill in the art and is discussed in detail in Ausubel (ed.), *Short Protocols in Molecular Biology*, Fourth Edition, John Wiley and Sons 1999. The following is a brief description of primer design.

Primer Design Strategy

Increased use of polymerase chain reaction (PCR) methods has stimulated the development of many programs to aid in the design or selection of oligonucleotides used as primers for PCR. Four examples of such programs that are freely available via the Internet are: PRIMER by Mark Daly and Steve Lincoln of the Whitehead Institute (UNIX, VMS, DOS, and Macintosh), Oligonucleotide Selection Program (OSP) by Phil Green and LaDeana Hiller of Washington University in St. Louis (UNIX, VMS, DOS, and Macintosh), PGEN by Yoshi (DOS only), and Amplify by Bill Engels of the University of Wisconsin (Macintosh only). Generally these programs help in the design of PCR primers by searching for bits of known repeated-sequence elements and then optimizing the $T_m$ by analyzing the length and GC content of a putative primer. Commercial software is also available and primer selection procedures are rapidly being included in most general sequence analysis packages.

Sequencing and PCR Primers

Designing oligonucleotides for use as either sequencing or PCR primers requires selection of an appropriate sequence that specifically recognizes the target, and then testing the sequence to eliminate the possibility that the oligonucleotide will have a stable secondary structure. Inverted repeats in the sequence can be identified using a repeat-identification or RNA-folding program such as those described above (see prediction of Nucleic Acid Structure). If a possible stem structure is observed, the sequence of the primer can be shifted a few nucleotides in either direction to minimize the predicted secondary structure. The sequence of the oligonucleotide should also be compared with the sequences of both strands of the appropriate vector and insert DNA. Obviously, a sequencing primer should only have a single match to the target DNA. It is also advisable to exclude primers that have only a single mismatch with an undesired target DNA sequence. For PCR primers used to amplify genomic DNA, the primer sequence should be compared to the sequences in the GenBank database to determine if any significant matches occur. If the oligonucleotide sequence is present in any known DNA sequence or, more importantly, in any known repetitive elements, the primer sequence should be changed.

The methods and materials of the invention may also be used more generally to evaluate animal DNA, genetically type individual animals, and detect genetic differences in animals. In particular, a sample of animal genomic DNA may be evaluated by reference to one or more controls to determine if a polymorphism in one of the sequences is present. Preferably, RFLP analysis is performed with respect to the animal's sequences, and the results are compared with a control. The control is the result of a RFLP analysis of one or both of the sequences of a different animal where the polymorphism of the animal gene is known. Similarly, the genotype of an animal may be determined by obtaining a sample of its genomic DNA, conducting RFLP analysis of the gene in the DNA, and comparing the results with a control. Again, the control is the result of RFLP analysis of one of the sequences of a different animal. The results genetically type the animal by specifying the polymorphism(s) in its gene. Finally, genetic differences among animals can be detected by obtaining samples of the genomic DNA from at least two animals, identifying the presence or absence of a polymorphism in one of the nucleotide sequences, and comparing the results.

These assays are useful for identifying the genetic markers relating to growth and meat quality, as discussed above, for identifying other polymorphisms in the same genes or alleles that may be correlated with other characteristics, and for the general scientific analysis of animal genotypes and phenotypes.

One of skill in the art, once a polymorphism has been identified and a correlation to a particular trait established will understand that there are many ways to genotype animals for this polymorphism. The design of such alternative tests merely represents optimization of parameters known to those of skill in the art and is intended to be within the scope of this invention as fully described herein.

In accordance with the present invention there may be employed conventional molecular biology, microbiology, and recombinant DNA techniques within the skill of the art. Such techniques are explained fully in the literature. See, e.g., Maniatis, Fritsch & Sambrook, *Molecular Cloning: A Laboratory Manual* (1982); DNA Cloning: A Practical Approach, Volumes I and II (D. N. Glover ed. 1985); Oligonucleotide Synthesis (M. J. Gait ed. 1984); *Nucleic Acid Hybridization* (B. D. Hames & S. J. Higgins eds. (1985)); *Transcription and Translation* (B. D. Hames & S. J. Higgins eds. (1984)); *Animal Cell Culture* (R. I. Freshney, ed. (1986)); *Immobilized Cells And Enzymes* (IRL Press, (1986)); B. Perbal, *A Practical Guide To Molecular Cloning*, (1984).

The invention also includes novel nucleotide and protein sequences which are associated with fatty acid content. This molecular information can be used in a variety of methods for studying the effects of, the causes of, and possibly the reversal or treatment of this condition in vitro and in vivo.

In another embodiment, the invention comprises a method for identifying a genetic marker for meat fatty acid content in a particular line, strain, breed, population or animal. Based upon the highly conserved nature of this gene among different animals and the location of the polymorphisms within these highly conserved regions, is it expected that with no more than routine testing as described herein this marker can be applied to different animal species to select for fatty acid content based on the teachings herein. For other animals in which sequences are available a BLAST comparison of sequences may be used to ascertain whether the particular allele is analogous to the one disclosed herein. The analogous polymorphism will be present in other animals and in other closely related genes. The term "analogous polymorphism" shall be a polymorphism which is the same as any of those disclosed herein as determined by BLAST comparisons using the default parameters.

Methods of alignment of sequences for comparison are well-known in the art. Optimal alignment of sequences for comparison may be conducted by the local homology algorithm of Smith and Waterman, *Adv. Appl. Math.* 2:482 (1981); by the homology alignment algorithm of Needleman and Wunsch, *J. Mol. Biol.* 48:443 (1970); by the search for similarity method of Pearson and Lipman, *Proc. Natl. Acad. Sci.* 85:2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73:237-244 (1988); Higgins and Sharp, CABIOS 5:151-153 (1989); Corpet, et al., *Nucleic Acids Research* 16:10881-90 (1988); Huang, et al., *Computer Applications in the Biosciences* 8:155-65 (1992), and Pearson, et al., *Methods in Molecular Biology* 24:307-331 (1994). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York (1995).

Unless otherwise stated, sequence identity/similarity values provided herein refer to the value obtained using the BLAST 2.0 suite of programs using default parameters. Altschul et al., *Nucleic Acids Res.* 25:3389-3402 (1997). Software for performing BLAST analyses is publicly available, e.g., through the National Center for Biotechnology-Information.

It is also possible to establish linkage between specific alleles of alternative DNA markers and alleles of DNA markers known to be associated with a particular gene (e.g. the FAS gene discussed herein), which have previously been shown to be associated with a particular trait. Thus, in the present situation, taking the FAS gene, it would be possible, at least in the short term, to select for animals likely to not exhibit improved fatty acid content, indirectly, by selecting for certain alleles of a FAS associated marker through the selection of specific alleles of alternative chromosome markers. As used herein the term "genetic marker" shall include not only the polymorphism disclosed by any means of assaying for the protein changes associated with the polymorphism, be also linked markers, use of microsatellites, or even other means of assaying for the causative protein changes indicated by the marker and the use of the same to influence the meat fatty acid content tendencies of an animal.

Example 1

Abstract

The objective of this study was to identify single nucleotide polymorphisms (SNPs) that were associated with beef fatty acid composition in the thioesterase (TE) domain of bovine fatty acid synthase (FAS) gene. The four exons that encode for TE were sequenced, and three SNPs, A17924G, T18663C, and C18727T, were detected. Purebred Angus cattle (n=331) were classified into three genotype groups, AA (n=121), AG (n=168), and GG (n=42), based on SNP A17924G. The A17924G genotype was significantly associated with fatty acid composition of *longissimus dorsi* (LD) muscle of purebred Angus bulls. Cattle with the GG genotype had lower myristic acid (C14:0; $P<0.0001$) and total saturated fatty acids contents (SFA; $P<0.01$), and greater health index (HI; $P<0.001$), oleic acid content (C18:1; $P<0.0001$), and total monounsaturated fatty acids concentrations concentration (MUFA; $P<0.001$) in the triacylglycerols (TAG) fraction than did those with the AA genotype. The differences of individual fatty acid percentage in total lipid of LD muscle were similar to those in the TAG. The cattle were also classified into three genotypes, TT (n=130), TC (n=162), and CC (n=39), according to the SNP T18663C. Because of the linkage disequilibrium between SNPs A17924G and T18663C, similar significant associations of fatty acid contents with the T18663C genotypes were observed.

Materials and Methods

Animals and samples collection. Purebred American Angus bulls (n=331) from Iowa State University beef breeding and tenderness projects were used in this study. Rib steaks were collected approximately 24 h post-harvest and returned to Iowa State University for processing. Bone, external adipose tissue, and connective tissue were removed from the LD muscle, and the sample was ground to homogeneity in a food processor and stored at −20° C. until analysis.

Fatty acid analysis. Total lipid was extracted with a chloroform and methanol (2:1, vol:vol) mixture and quantified (Folch et al., 1957). Phospholipids (PL) content was determined by measuring the total phosphorus amount according to Chen et al. (1956). Triacylglycerols (TAG) were separated from PL by thin-layer chromatography run in hexane and ethyl acetate (4:1; v:v). The individual lipid spots were derivatized to methyl esters with acetyl chloride in methanol prior to gas chromatography for determination of fatty acid composition. Fatty acid methyl esters (FAME) were analyzed by a gas chromatography (model 3400, Varian, Palo Alto, Calif.) equipped with a Supelco SP-2380 column (30 m×0.25 mm i.d.×0.20 µm film thickness) and a flame ionization detector. The column started at a temperature of 100° C. and was ramped up to 170° C. at a rate of 2° C. per minute, followed by an increase to 180° C. at 0.5° C. per minute and to 250° C. at 10° C. per minute. The total running time was 62 min. The temperature of the injector was programmed to increase from 68° C. to 250° C. at a rate of 250° C. per minute. The detector was maintained at 220° C. The fatty acids in the entire sample (PL plus TAG) were estimated on the basis of a weighted average of PL and TAG fatty acid composition. In addition to fatty acid composition data, health index was calculated as the inverse of atherogenic index (AI) proposed by Ulbright and Southgate (1991) as shown below:

$$HI = \frac{\sum MUFA + \sum PUFA}{4 \cdot C14:0 + C16:0}$$

DNA polymorphisms identification. Genomic DNA samples were isolated by proteinase K digestion followed by phenol extraction. Primers were designed to amplify the four exons of TE domain of FAS gene (Table 1). The The PCR reaction mixture contained 50 ng of genomic DNA, 1.5 mM $MgCl_2$, 400 nM of each primer, 0.2 mM of dNTP mixture, 2 µl DMSO, and 1 U of DNA polymerase at a final volume of 25 µl. The PCR reactions were performed in a DNA engine thermal cycler (Bio-Rad) with the following protocol: 94° C. for 2 min, followed by 35 cycles of 94° C. for 12 s, 56° C. for 30 s, and 72° C. for 30 s, with a final extension step at 72° C. for 10 min. The DNA sequence of PCR amplicons were determined with ABI 3730 DNA Analyzer (Applied Biosystems Inc.).

Genotyping. The genotypes of polymorphism A17924G in FAS gene were detected by PCR-RFLP. One set of primers named MSC (Table 1) were designed to amplify a 382 bp DNA fragment that contained the mutation site. Genotypes were determined by digestion with MSC I. Amplified DNA with the GG genotype was digested into two fragments of 355 bp and 27 bp. In contrast, PCR product with the AA genotype was digested into three fragments of 188 bp, 167 bp, and 27 bp. The fragments were separated using 2% PCR grade agarose gel. The genotypes of polymorphisms T18663C and C18727T were determined by sequencing by using primer TE-c.

Statistical analysis. Least squares means (±SE) were determined by using a mixed linear model (PROC MIXED; SAS Inst., Inc., Cary, N.C.) that included the fixed effects of TE genotypes, age, and marbling score as a covariate and random effects of contemporary groups and sire. The cattle that were fed different diets but were reared and harvested in the same time were classified into different contemporary groups. The effects of different diets, therefore, were corrected by contemporary groups. Means were compared by using pairwise t-tests and determined to be different at $P<0.05$. Tukey-Kramer adjustment was carried out to adjust for multiple testing. Regression and correlation analyses of phenotypical traits on the number of alleles were carried out. Correlation coefficients and coefficients of determination were determined to be significant at $P<0.05$.

Results

Figure 2:
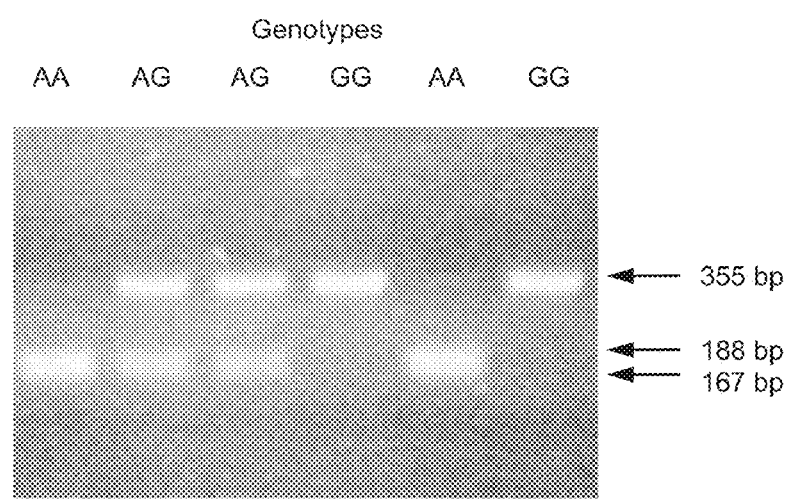
FIG. 2. Genotyping polymorphism A17924G. Digestion of restriction enzyme MSC I revealed the genotypes AA, AG, and GG. The arrows show the size of DNA fragments.

DNA polymorphism identification and genotyping. The TE domain is located at the 3'-end of FAS and is encoded within 4 exons (exons 39 to 42). We compared the TE exonic sequences of 46 purebred Angus bulls. Three nucleotide substitutions were identified at positions 17924 (A to G), 18663 (C to T), and 18727 (C to T), respectively, on bovine FAS gene (AF285607; FIG. 1, FIG. 4). Polymorphism A17924G was predicted to result in an amino acid replacement from threonine (ACC) to alanine (GCC) in FAS protein. The other two SNPs, T18663C and C18727T, are silent mutations. Genotypes of 345 Angus bulls at position 17924 were determined by PCR-RFLP (FIG. 2). The SNPs, T18663C and C18727T, were genotyped by sequence analysis. Approximately half of the bulls were heterozygous for SNPs A17924G and T18663C, respectively (Table 2a). In contrast, genotype frequency of heterozygous CT was only 3.0% for polymorphism C18727T (Table 2a). The A and T allele frequencies for A17924G and T18663C were 61.9% and 63.7%, respectively. In contrast, the C allele frequency for C18727T was predominant, namely 98.5% (Table 2b). The genotypes of the three SNPs were classified into 6 groups as illustrated in Table 2c. The genomic DNA samples with genotype AA for polymorphism A17924G had genotypes TT and CC for SNPs T18663C and C18727T, respectively. Approximately 92.8% of the cattle with genotypes GG for A17924G had genotypes CC and CC for T18663C and C18727T, respectively. Furthermore, animals that were heterozygous at position 17924 were heterozygous for either T18663C or C18727T, but not both. The genotype classes observed could be accounted for with a minimum of three 3-locus haplotypes, including ATC GCC, and GTT. Combination of these three haplotypes were sufficient to explain all observed genotypes.

Thioesterase amino acid alignment. The TE domain is located near the C terminus of the FAS multienzyme complex with molecular weight of approximately 32 kDa (Joshi and Smith, 1993; Smith et al., 1976). The amino acid sequence alignment of bovine FAS TE with some mammalian species is shown in FIG. 3. The bovine sequence displayed 94.1%, 83.0%, and 79.0% identities to that of goat (ABB36643), human (NP_004095), and rat (P12785) sequences, respectively. The catalytic residues (Pazirandeh et al., 1991) were conserved across species. Similarly, the amino acids identified as fatty acyl substrate binding site in human FAS (Chakravarty et al., 2004) are invariant among species. In contrast, the residue site, in which polymorphism A17924G was predicted to cause amino acid from threonine to alanine, was not conserved (FIG. 3). Goat and rat, however, have the same residue, namely alanine, as cattle with the GG genotype.

Association of SNP genotype with fatty acid composition of LD muscle. Among the 3 SNPs identified, the SNPs A17924G and T18663C were significantly associated with the concentrations of several individual fatty acids in PL, TAG, and total lipids (Table 3). There was no association detected between the fatty acid composition and C18727T genotype (data not shown). However, the T allele frequency of C18727T was only 1.6% (Table 2b), which precludes obtaining large number of TT homozygote animals.

The SNP A17924G was significantly associated with the concentrations of several fatty acids in the PL fraction (Table 3). The percentages of oleic acid (C18:1), docosapentaenoic acid (C20:5), and total MUFA were greater ($P<0.05$) in Angus cattle with the GG genotype than those with the AA genotype. In contrast, the eicosatrienoate (C20:3) content was greater ($P<0.05$) in the cattle with AA genotype than in those with GG genotype. In addition, the content of total PUFA tended to be greater ($P=0.09$) in the AA genotype cattle than in the cattle with GG genotype. Similar association of genotypes with contents of fatty acids was observed for polymorphism T18663C (Table 3). The cattle with genotype TT had greater C18:1 and MUFA concentrations and lower 20:3 and PUFA contents than did the cattle with genotype CC ($P<0.05$).

Significant association of the A17924G genotype with fatty acid composition of TAG was observed (Table 3). The concentration of myristic acid (C14:0) was 15.6% ($P<0.0001$) and 10.4% ($P<0.001$) less in the cattle with genotype GG than in those with AA and AG, respectively. In addition, the cattle with genotype AG had a lower percentage of C14:0 than did cattle with the genotype AA ($P<0.01$). The percentages of pentadecanoic acid (C15:0), palmitic acid (C16:0), and total SFA were greater, whereas the content of total MUFA was lower, in the cattle with genotype AA than in those with genotype GG ($P<0.05$). The ratio of C16:0 to C14:0, however, was greater in the cattle with genotype GG than those of the other two genotypes ($P<0.0001$). The C18:1 content in the cattle with GG genotype was greater than those of the AA genotype ($P<0.0001$) and AG genotype cattle ($P<0.05$). Moreover, the AG genotype cattle had greater C18:1 content than did the cattle with AA genotype ($P<0.01$). Consequently, cattle with genotype GG had the greatest HI, whereas cattle with genotype AA had the lowest HI ($P<0.05$). Similarly, the SNP T18663C contributed to the variation of the contents of several fatty acids in TAG (Table 3). The cattle with genotype CC had greater HI, C18:1, MUFA, and C16:0 to C14:0 ratio and lower contents of C14:0 and SFA than did the cattle with genotype TT ($P<0.05$).

The effects of A17924G genotype on fatty acid composition of total lipids were similar as the effects observed in the TAG fraction (Table 3). The C14:0, C16:0, and total SFA contents were lower, whereas the C16:0 to C14:0 ratio and C18:1 and total MUFA concentrations were greater in the genotype GG cattle than in the cattle with genotype AA ($P<0.05$). Consequently, the cattle with genotype GG had greater HI than did the cattle with genotype AA ($P<0.001$). Similarly, the T18663C genotype was significant associated with the contents of several fatty acids in total lipids ($P<0.05$). The cattle with CC genotype had greater C18:1 and total MUFA contents, larger HI, greater C16:0 to C14:0 ratio, and lower C14:0 concentration than did cattle with TT genotype. In addition, the heterozygous, but not cattle with CC genotype, had lower C16:0 and total SFA than did the cattle with TT genotype, which may be attributed to the difference in sample size.

The total lipids content and marbling score, however, were not significantly affected by the SNPs A17924G and T18663C ($P>0.05$). The muscular lipids content was $3.85\pm0.20$, $3.64\pm0.19$, and $4.03\pm0.28$ (g/100 g of meat) and the marbling score was $4.74\pm0.14$, $4.78\pm0.14$, and $4.89\pm0.16$ for the cattle with genotype AA, AG, and GG, respectively, as based on the SNP A17924G. Similarly, the lipids content was $3.86\pm0.20$, $3.67\pm0.19$, and $3.94\pm0.27$ (g/100 g of meat) and the marbling score was $4.75\pm0.14$, $4.77\pm0.14$, and $4.93\pm0.17$ for the cattle with genotype TT, TC, and CC, respectively, when classified according to the SNP T18663C.

Contribution of TE genotype to fatty acid composition of LD muscle. Correlation and regression analyses of fatty acid contents on the number of G alleles for the SNP A17924G and on the number of C alleles for the SNP T18663 were carried out to further assess the association of genotype to fatty acid composition. Table 4 shows the correlation coefficients (R) and coefficients of determination ($R^2$) that were significant. The number of G alleles at position 17924 was correlated positively to C18:1 ($R=0.16$; $P<0.01$) and MUFA ($R=0.16$, $P<0.01$) contents, and negatively to C20:3 ($R=0.14$, $P<0.05$) and PUFA ($R=0.12$, $P<0.05$) percentages in the PL. The variations of C18:1 and C20:3 explained by the allele, however, were small ($R^2=0.03$ and $0.01$, respectively). Similarly, the C allele at position 18663 was associated with greater C18:1 ($R=0.17$; $P<0.01$) and MUFA ($R=0.17$, $P<0.01$) concentrations and lower C20:3 ($R=0.11$, $P<0.05$) and PUFA ($R=0.16$, $P<0.01$) contents in PL.

Greater correlation coefficients between alleles and individual fatty acid were observed in TAG (Table 4). The number of G alleles was correlated negatively to C14:0 ($R=-0.28$, $P<0.0001$), C15:0 ($R=-0.17$, $P<0.01$), C16:0 ($R=-0.19$, $P<0.001$), and SFA ($R=-0.19$, $P<0.001$) and positively to C18:1 ($R=0.29$, $P<0.0001$), MUFA ($R=0.23$, $P<0.0001$), C16:0 to C14:0 ratio ($R=0.13$, $P<0.05$), and HI ($R=0.27$, $P<0.0001$). In addition, genotypes explained approximately 7.8%, 8.3%, 5.3%, and 7.2% of the total variations of C14:0, C18:1, MUFA, and HI, respectively (Table 4). The correlations of these traits with the number of C alleles at position 18663 were smaller than those with the number of G allele at position 17924. In addition, the number of C alleles was correlated negatively with content of PUFA in TAG (R=–0.13, P<0.05).

The correlations between the number of alleles and the percentages of individual fatty acid in total lipid were similar to those observed in TAG (Table 4). Negative correlations were observed between the number of G alleles of SNP A17924G and several individual SFA, C14:0 (R=–0.25, P<0.0001), C15:0 (R=–0.15, P<0.01), and C16:0 (R=–0.17, P<0.01). Consequently, the total SFA was correlated negatively with the G allele number (R=–0.16, P<0.01). In contrast, positive correlations were obtained between the number of G alleles and C18:1 (R=0.20, P<0.001), total MUFA (R=0.14, P<0.01), C16:0 to C14:0 ratio (R=0.19, P<0.001), and HI (R=0.24, P<0.0001), respectively. Approximately 6.3%, 3.8%, and 5.6% of the total variances of C14:0, C18:1, and HI were explained by the number of G alleles. Similarly, the number of C alleles of SNP T18663C was correlated negatively with C14:0, C16:0, and total SFA, and positively correlated with C18:1 and total MUFA (P<0.05). The correlations of these traits with the number of C alleles at position 18663 were smaller than those with the number of G alleles at position 17924.

Discussion

In the current study, three novel SNPs were discovered in the TE domain of FAS gene. We have shown that the G allele at position 17924 and the C allele at position 18663 contributed to lower contents of C14:0 and C16:0 in TAG and to greater percentage of C18:1 in both PL and TAG in the LD muscle of purebred Angus bulls (Table 3). The effects of these alleles seemed to be additive. For each individual fatty acid or index that was significantly associated with the 2 SNPs, respectively, the numerical value of the heterozygotes always lay between the two homozygotes (Table 3). The correlation analysis revealed significant association of the number of G alleles with the C14:0, C18:1, and HI in both the TAG and total lipids (Table 4). Regression analysis indicated that approximately 7.8% and 6.3% of the phenotypic variations of C14:0 contents in TAG and total lipids, respectively, could be explained by the A17924G genotype (Table 4). Kovacs et al (2004) reported a SNP in human FAS that is associated with percentage of body fat and substrate oxidation rates in non-diabetic Pima Indians. A recent study on bovine FAS gene (Roy et al., 2006) identified polymorphisms that could contribute to variation in milk fat content. In the current study, however, the SNPs in FAS TE were not significantly associated with the total lipids contents and marbling scores in the LD muscle. Mammalian FAS complex is an essential enzyme in fatty acid synthesis, which catalyzes the formation of long-chain SFA from acetyl-coenzyme A (acetyl-CoA) and malonyl-CoA in the presence of NADPH as the source of reduction. The last step of chain-termination is catalyzed by the TE domain of FAS. Both C14 acyl-ACP and C16 acyl-ACP are substrates for TE. The hydrolysis rate of C14 acyl-ACP by FAS TE, however, is much slower than that of C16 acyl-ACP (Lin and Smith, 1978; Pazirandeh et al., 1989). The product of FAS, therefore, is mainly C16:0, with minor amounts of C14:0. Consequently, the TE domain plays a major role in determination of the product chain length of FAS. Structure of human FAS TE revealed the presence of a hydrophobic groove, which constitutes the fatty acyl substrate binding site (Chakravarty et al., 2004). Therefore, the highly specific activity of TE toward C16-acyl ACP and C18-acyl ACP, but not C14-acyl ACP, is attributed to the geometry and nature of substrate binding site.

The amino acid sequence alignment of cattle and human showed that the amino acid replacement found in the current study occurred at a position, which is located a few amino acids c-terminal to a candidate substrate binding site (FIG. 3). It is possible that the amino acid substitution in TE domain predicted by the SNP A17924G may influence the structure of substrate binding site and consequently affect the specific activities of TE toward C14-acyl ACP. This hypothesized decrease of hydrolysis activity of TE on C14-acyl ACP, which was caused by the replacement of threonine to alanine, might further result in less C14:0 content and greater C16:0 to C14:0 ratio in GG (alanine) than AA (threonine) genotype bulls. The SNP T18663C is a silent mutation. The significant association of T18663C with several fatty acid contents could be attributed to the strong linkage disequilibrium between T18663C and A17924G.

The elongation of fatty acids occurs in both the mitochondrial and microsomal membranes, but the predominant site of elongation is the membrane of the ER. Generally, the mitochondrial elongation system targets fatty acyl-CoA substrates in the range of C10-C14, whereas microsomal elongases act on C16 and longer chain fatty acid (Hardwood, 1994). The observed lower C16:0 content in TAG and total lipid of genotype GG cattle compared with genotype AA cattle classified according to the SNP A17924G could be attributed to the fact that C16:0 is the substrate for both elongase and stearoyl-CoA desaturase (SCD). Greater 18:1 content in genotype GG cattle than AA cattle was observed in PL, TAG, and total lipids. This observation could be explained if more C16:0 and less C14:0 were produced by FAS of GG genotype cattle as compared with AA cattle, and consequently, more C16:0 was elongated to C18:0, which was further converted to C18:1 (n9), a major end product of de novo fatty acid synthesis. It is also possible that more C16:0 was converted to C16:1 by SCD, which consequently resulted in more C18:1 (n7) by elongation. Because the GC column we used could not separate the isomers of C18:1, the percentage of C18:1 obtained in the current study should be the sum of several C18:1 isomers. Consequently, greater C18:1 was observed when the percentage of 18:1 (n7) increased. Interestingly, greater content of C20:3 was found in PL of genotype AA cattle compared with GG bulls and the PUFA content tended to be greater (P=0.09) in the cattle with genotype AA than in the cattle with genotype GG. Furthermore, the cattle with TT genotype classified according to the SNP T18663C had greater content of PUFA than did the cattle with CC genotype (P<0.05). Phospholipids (PL) are the major component of plasma membrane. The degree of unsaturation of fatty acyl chain of PL plays an important role in determining physical properties of cell membrane (Hise et al., 1986). The association of increased MUFA content with decreased PUFA concentration observed in the current study was expected so that the similar degree of unsaturation of PL could be kept.

Stearyol-CoA desaturase catalyzes the conversion of SFA to MUFA. Studies have shown that the differences in MUFA percentage were correlated with SCD activity in cattle (Sturdivant et al., 1992; Yang et al, 1999; Laborde et al., 2001). Taniguchi et al. (2004) identified a coding SNP in SCD gene and classified 1003 Japanese Black cattle to three genotypes, VV, VA, and AA. The analysis showed that the AA genotype cattle had 1.7% greater MUFA content in adipose tissue than did the VV genotype cattle. Keating et al. (2005) isolated and characterized the SCD promoter of dairy cows but did not find any SNPs among cows producing high and low content of conjugated linoleic acid (CLA) in milk. In the current study, we observed significant association of SNPs in TE domain of FAS with fatty acid composition of LD muscle of Angus bulls (Tables 3). Moreover, the MUFA contents of PL, TAG, and total lipids in cattle with genotype GG classified according to SNP A17924G was 7.2%, 3.0%, and 3.4%, respectively, greater than those of the genotype AA cattle (P<0.05). These differences could be attributed to the differences in C18:1 percentage, which is the major component of MUFA. Our results indicate that not only SCD, but also FAS TE genotypes contribute to the variation of MUFA content.

In summary, results of the current study indicated that genotyping of FAS TE gene is a useful tool to select Angus cattle with less atherogenic SFA and more MUFA and therefore to improve healthfulness of fatty acids in beef.

REFERENCES

1. Bonanome A, Grundy S (1988) Effect of dietary stearic acid on plasma cholesterol and lipoprotein concentrations. New Eng J Med 318, 1244-1248
2. Bronte-Stewart B, Antonis A, Eales L, Brock J F (1956) Effects of feeding different fats on serum-cholesterol level. Lancet 270, 521-526
3. Chakravarty B, Gu Z, Chirala S S, Wakil S J, Quiocho F A (2004) Human fatty acid synthase: Structure and substrate selectivity of the thioesterase domain. Proc Natl Acad Sci 101, 15567-15572
4. Chen P S, Toribara T Y, Warner H (1956) Microdetermination of phosphorus. Analyt Chem 28, 1756-1758
5. Folch J M, Lees M, Sloane Stanley G H (1957) A simple method for the isolation and purification of total lipids from animal tissue. J Biol Chem 226, 497-509
6. Harwood J K (1994) Lipid Metabolism. In the Lipid Handbook, second ed. (Chapman & Hall, London, UK), pp 605-664
7. Hise M K, Mantulin W W, Weinman E J (1986) Fatty acyl chain composition in the determination of renal membrane order. J Clin Invest 77, 768-773
8. Keating A F, Stanton C, Murphy J J, Smith T J, Ross R P, Cairns M T (2005) Isolation and characterization of the bovine stearoyl-CoA desaturase promoter and analysis of polymorphisms in the promoter region in dairy cows. Mamm Genome 16,184-193
9. Keys A, Grande F, Anderson J T (1974) Bias and misrepresentation revisited-"perspective" in saturated fat. Am J Clin Nutr 27, 188-212
10. Kovacs P, Harper I, Hanson R L, Infante A M, Bogardus C, Tataranni P A, Baier L J (2004) A novel missense substitution (Val1483Ile) in the fatty acid synthase gene (FAS) is associated with percentage of body fat and substrate oxidation rates in nondiabetic pima indians. Diabetes 53, 1915-1919
11. Joshi A K, Smith S (1993) Construction, expression, and characterization of a mutated animal fatty acid synthase deficient in the dehydrase function. *J Biol Chem* 268, 22508-22513
12. Laborde F L, Mandell I B, Tosh J J, Wilton J W, Buchanan-Smith J G (2001) Breed effects on growth performance, carcass characteristics, fatty acid composition, and palatability attributes in finishing steers. J Anim Sci 79, 355-365
13. Lin C Y, Smith S (1978) Properties of the thioesterase component obtained by limited trypsinization of the fatty acid synthetase multienzyme complex. J Biol Chem 253, 1954-1962
14. Morris C A, Cullen N G, Glass B C, Hyndman D L, Manley T R, Hickey S M, McEwan JC, Pitchford W S, Bottema C D, Lee M A (2007) Fatty acid synthase effects on bovine adipose fat and milk fat. Mamm Genome 18, 64-74
15. Pazirandeh M, Chirala S S, Huang W Y, Wakil S J (1989) Characterization of recombinant thioesterase and acyl carrier protein domains of chicken fatty acid synthase expressed in *Escherichia coli*. J Biol Chem, 264, 18195-18201
16. Pazirandeh M, Chirala S S, Wakil S J (1991) Site-directed mutagenesis studies on the recombinant thioesterase domain of chicken fatty acid synthase expressed in *Escherichia coli*. J Biol Chem, 266, 20946-20952
17. Roy R, Ordovas L, Zaragoza P, Romero A, Moreno C, Altarriba J, Rodellar C (2006) Association of polymorphisms in the bovine FASN gene with milk-fat content. Anim Genetics 37, 215-218
18. Rudel L L, Park J S, Sawyer J K (1995) Compared with dietary monounsaturated and saturated fat, polyunsaturated fat protects African green monkeys from coronary artery atherosclerosis. Arterioscler Thromb Vasc Biol 15, 2101-2110
19. Smith S, Agradi E, Libertini L, Dileepan K N (1976) Specific release of the thioesterase component of the fatty acid synthetase multienzyme complex by limited trypsinization. Proc Natl Acad Sci 73, 1184-1188
20. Sturdivant C A, Lunt D K, Smith G C, Smith S B (1992) Fatty acid composition of subcutaneous and intramuscular adipose tissues and *M. longissimus dorsi* of Wagyu cattle. Meat Sci. 32, 449-458
21. Taniguchi M, Utsugi T, Oyama K, Mannen H, Kobayashi M, Tanabe Y, Ogino A, Tsuji S (2004) Genotype of stearoyl-CoA desaturase is associated with fatty acid composition in Japanese Black cattle. Mamm Genome 15, 142-148.
22. Ulbricht TLV, Southgate DAT (1991) Coronary heart disease: seven dietary factors. The Lancet 338, 985-992
23. Woollett L A, Spady D K, Dietschy J M (1992) Saturated and unsaturated fatty acid independently regulate low density lipoprotein receptor activity and production rate. J Lipid Res 33, 77-88
24. Xue B, Zemel M B (2000) Relationship between human adipose tissue agouti and fatty acid synthase (FAS). J Nutr 130, 2478-2481
25. Yang A, Larsen T W, Smith S B, Tume R K (1999) $\Delta^9$-desaturase activity in bovine subcutaneous adipose tissue of different fatty acid composition. Lipids 34, 971-978.

TABLE 1

Primer sequences.

| Primer Name | Sequence Forward | Reverse |
|---|---|---|
| TE-a | agagctgacggactcca cac (SEQ ID NO: 7) | ctgcatgaagaagcacatgg (SEQ ID NO: 8) |
| TE-b | ctcgcacaccttcgtg atg (SEQ ID NO: 9) | cacgttgccgtggtaggtag (SEQ ID NO: 10) |
| TE-c | cgctcactgtcctgtcc tac (SEQ ID NO: 11) | gctgtgaataatactaagga tgga (SEQ ID NO: 12) |
| MSC | agagctgacggactcca cac (SEQ ID NO: 13) | gcctgatgcactcgatgtag (SEQ ID NO: 14) |

TABLE 2a

Polymorphisms in TE domain of FAS and gene frequency.

|  | A17924G[1] | | | T18663C | | | C18727T | | |
|---|---|---|---|---|---|---|---|---|---|
| Variable | AA | AG | GG | TT | CT | CC | CC | CT | TT |
| Number of animals | 121 | 168 | 42 | 130 | 162 | 39 | 320 | 10 | 1 |
| Genotype frequency | 0.36 | 0.51 | 0.13 | 0.39 | 0.49 | 0.12 | 0.97 | 0.03 | 0.003 |

TABLE 2b

Allele distribution of polymorphisms in TE domain of FAS.

|  | A17924G[1] | | T18663C | | C18727T | |
|---|---|---|---|---|---|---|
| Variable | A | G | T | C | C | T |
| Allele frequency | 0.62 | 0.38 | 0.64 | 0.36 | 0.98 | 0.02 |

TABLE 2c

Compiled genotype distribution of polymorphisms in TE domain of FAS.

| Group | SNPs | | | Number of animals | Genotype frequency |
|---|---|---|---|---|---|
|  | A17924G[1] | T18663C | C18727T | | |
| 1 | AA | TT | CC | 121 | 0.37 |
| 2 | AG | TC | CC | 160 | 0.48 |
| 3 | AG | TT | CT | 8 | 0.02 |
| 4 | GG | CC | CC | 39 | 0.12 |
| 5 | GG | TC | CT | 2 | 0.01 |
| 6 | GG | TT | TT | 1 | 0.003 |

[1]SNP that results in an amino acid substitution.

TABLE 3

Effects of thioesterase genotypes on phospholipids (PL), triacylglycerols (TAG), and total lipids fatty acid composition[1].

|  | A17924G | | | T18663C | | |
|---|---|---|---|---|---|---|
| Traits | AA (n = 121) | AG (n = 168) | GG (n = 42) | TT (n = 130) | TC (n = 162) | CC (n = 39) |
| PL |  |  |  |  |  |  |
| 18:1 | $23.40 \pm 0.90^b$ | $24.01 \pm 0.89^{a,b}$ | $25.07 \pm 1.00^a$ | $23.46 \pm 0.90^B$ | $24.00 \pm 0.88^{A,B}$ | $25.16 \pm 1.01^A$ |
| 20:3 (n-6) | $1.94 \pm 0.06^a$ | $1.89 \pm 0.06^{a,b}$ | $1.75 \pm 0.08^b$ | $1.93 \pm 0.06^A$ | $1.90 \pm 0.06^A$ | $1.74 \pm 0.08^B$ |
| 22:5 (n-3) | $2.44 \pm 0.10^b$ | $2.49 \pm 0.10^{a,b}$ | $2.61 \pm 0.11^a$ | $2.44 \pm 0.10$ | $2.50 \pm 0.10$ | $2.59 \pm 0.11$ |
| MUFA[2] | $25.16 \pm 0.95^b$ | $25.83 \pm 0.93^{a,b}$ | $26.98 \pm 1.05^a$ | $25.23 \pm 0.94^B$ | $25.82 \pm 0.93^{A,B}$ | $27.09 \pm 1.06^A$ |
| PUFA[3] | $45.22 \pm 0.86$ | $44.89 \pm 0.83$ | $43.51 \pm 1.02$ | $45.23 \pm 0.85^A$ | $44.91 \pm 0.82^{A,B}$ | $43.26 \pm 1.02^B$ |
| TAG |  |  |  |  |  |  |
| 14:0 | $3.46 \pm 0.09^a$ | $3.26 \pm 0.09^b$ | $2.92 \pm 0.11^c$ | $3.41 \pm 0.09^A$ | $3.27 \pm 0.09^A$ | $2.93 \pm 0.12^B$ |
| 15:0 | $0.41 \pm 0.03^a$ | $0.38 \pm 0.03^{a,b}$ | $0.32 \pm 0.04^b$ | $0.40 \pm 0.03$ | $0.39 \pm 0.03$ | $0.34 \pm 0.04$ |
| 16:0 | $28.54 \pm 0.22^a$ | $28.09 \pm 0.20^{a,b}$ | $27.65 \pm 0.30^b$ | $28.41 \pm 0.22$ | $28.13 \pm 0.21$ | $27.72 \pm 0.32$ |
| 18:1 | $44.76 \pm 0.29^c$ | $45.63 \pm 0.27^b$ | $46.59 \pm 0.40^a$ | $44.94 \pm 0.29^C$ | $45.58 \pm 0.28^B$ | $46.53 \pm 0.42^A$ |
| SFA[4] | $46.36 \pm 0.40^a$ | $45.75 \pm 0.38^b$ | $45.11 \pm 0.49^b$ | $46.19 \pm 0.40^A$ | $45.81 \pm 0.39^{A,B}$ | $45.21 \pm 0.50^B$ |
| MUFA | $49.99 \pm 0.31^b$ | $50.70 \pm 0.29^a$ | $51.50 \pm 0.41^a$ | $50.15 \pm 0.31^B$ | $50.65 \pm 0.29^{A,B}$ | $51.42 \pm 0.41^A$ |
| 16:0/14:0[5] | $8.45 \pm 1.02^b$ | $8.76 \pm 0.85^b$ | $14.35 \pm 1.73^a$ | $8.55 \pm 1.02^B$ | $8.71 \pm 0.85^B$ | $14.74 \pm 1.73^A$ |
| HI[6] | $1.25 \pm 0.02^c$ | $1.30 \pm 0.02^b$ | $1.38 \pm 0.03^a$ | $1.26 \pm 0.02^B$ | $1.30 \pm 0.02^B$ | $1.37 \pm 0.03^A$ |
| Total lipids |  |  |  |  |  |  |
| 14:0 | $2.85 \pm 0.06^a$ | $2.68 \pm 0.05^b$ | $2.45 \pm 0.08^c$ | $2.81 \pm 0.06^A$ | $2.69 \pm 0.05^A$ | $2.48 \pm 0.08^B$ |
| 16:0 | $26.48 \pm 0.24^a$ | $25.91 \pm 0.23^b$ | $25.67 \pm 0.31^b$ | $26.35 \pm 0.24^A$ | $25.93 \pm 0.23^B$ | $25.80 \pm 0.32^{A,B}$ |
| 18:1 | $40.38 \pm 0.36^b$ | $40.98 \pm 0.33^b$ | $42.17 \pm 0.48^a$ | $40.54 \pm 0.36^B$ | $40.90 \pm 0.33^B$ | $42.23 \pm 0.48^A$ |
| SFA | $43.82 \pm 0.21^a$ | $43.04 \pm 0.18^b$ | $42.82 \pm 0.34^b$ | $43.68 \pm 0.21^A$ | $43.05 \pm 0.18^B$ | $42.99 \pm 0.34^{A,B}$ |
| MUFA | $44.96 \pm 0.49^b$ | $45.39 \pm 0.47^{a,b}$ | $46.49 \pm 0.60^a$ | $45.10 \pm 0.49^B$ | $45.32 \pm 0.47^B$ | $46.53 \pm 0.60^A$ |

TABLE 3-continued

Effects of thioesterase genotypes on phospholipids (PL), triacylglycerols (TAG), and total lipids fatty acid composition[1].

| | A17924G | | | T18663C | | |
|---|---|---|---|---|---|---|
| Traits | AA (n = 121) | AG (n = 168) | GG (n = 42) | TT (n = 130) | TC (n = 162) | CC (n = 39) |
| 16:0/14:0 | $9.52 \pm 0.26^b$ | $9.87 \pm 0.22^b$ | $11.38 \pm 0.41^a$ | $9.62 \pm 0.25^B$ | $9.84 \pm 0.23^B$ | $11.38 \pm 0.43^A$ |
| HI | $1.50 \pm 0.02^b$ | $1.57 \pm 0.02^a$ | $1.63 \pm 0.03^a$ | $1.51 \pm 0.02^B$ | $1.57 \pm 0.02^A$ | $1.61 \pm 0.03^A$ |

[1]Values are expressed as LSM ± SE. Fatty acid contents are expressed as g/100 g of total fatty acids.
[2]Total monounsaturated fatty acids (MUFA).
[3]Total polyunsaturated fatty acids (PUFA).
[4]Total saturated fatty acids (SFA).
[5]Calculated as the ratio of 16:0 to 14:0.
[6]Health index, calculated as $(\Sigma MUFA + \Sigma PUFA)/(4 \times 14:0 + 16:0)$.
[a,b,c]Values in the same row for SNP A17924G with different subscripts differ at $P < 0.05$.
[A,B,C]Values in the same row for SNP T18663C with different subscripts differ at $P < 0.05$.

TABLE 4

Coefficients of determination ($R^2$) and correlation coefficients (R) from regression and correlation analyses of traits on the number of G alleles for SNP A17924G and on the number of C alleles for SNP T18663C[1].

| | A17924G | | | T18663C | | |
|---|---|---|---|---|---|---|
| Trait | $R^2$ | R | P-Value | $R^2$ | R | P-Value |
| PL[2] | | | | | | |
| 18:1 | 0.03 | 0.16 | ** | 0.03 | 0.17 | ** |
| 20:3 n-6 | 0.01 | −0.12 | * | 0.01 | −0.11 | * |
| MUFA[3] | 0.03 | 0.16 | ** | 0.03 | 0.17 | ** |
| PUFA[4] | 0.02 | −0.14 | * | 0.03 | −0.16 | ** |
| TAG[5] | | | | | | |
| 14:0 | 0.08 | 0.28 | **** | 0.05 | −0.22 | **** |
| 15:0 | 0.03 | −0.17 | ** | 0.01 | −0.11 | * |
| 16:0 | 0.04 | −0.19 | *** | 0.02 | −0.13 | * |
| 18:1 | 0.08 | 0.29 | **** | 0.06 | 0.24 | **** |
| SFA[6] | 0.03 | −0.19 | *** | 0.02 | −0.14 | * |
| MUFA | 0.05 | 0.23 | **** | 0.04 | 0.19 | *** |
| PUFA | — | — | NS | 0.02 | 0.13 | * |
| 16:0/14:0[7] | 0.02 | 0.13 | * | 0.02 | 0.12 | * |
| HI[8] | 0.07 | 0.27 | **** | 0.04 | 0.20 | *** |
| Total Lipid | | | | | | |
| 14:0 | 0.06 | −0.25 | **** | 0.04 | −0.19 | *** |
| 15:0 | 0.02 | −0.15 | ** | — | — | NS |
| 16:0 | 0.03 | −0.17 | ** | 0.01 | −0.12 | * |
| 18:1 | 0.04 | 0.20 | *** | 0.03 | 0.17 | ** |
| SFA | 0.04 | −0.19 | *** | 0.02 | −0.14 | * |
| MUFA | 0.02 | 0.14 | ** | 0.02 | 0.13 | * |
| 16:0/14:0 | 0.04 | 0.19 | *** | 0.03 | 0.16 | ** |
| HI | 0.06 | 0.24 | **** | 0.03 | 0.18 | ** |

[1]Data significantly different from 0 for either of the polymorphisms are shown here ($P < 0.05$). The correlation and regression analyses yielded the same p-values for each trait.
[2]Phospholipids (PL).
[3]Total monounsaturated fatty acids (MUFA).
[4]Total polyunsaturated fatty acids (PUFA).
[5]Triacylglycerols (TAG).
[6]Total saturated fatty acids (SFA).
[7]7Calculated as the ratio of 16:0 to 14:0.
[8]Health index, calculated as $(\Sigma MUFA + \Sigma PUFA)/(4 \times 14:0 + 16:0)$.
*$P < 0.05$;
**$P < 0.01$;
***$P < 0.001$;
****$P < 0.0001$;
NS: not significant.

What is claimed is:

1. A method for detecting fatty acid content in a bovine subject's muscle tissue, comprising: lower C14:0 content and lower C16:0 content in triacylglycerols (TAG) and a greater percentage of C18:1 content in phospholipids (PL) and TAG, wherein the presence of at least one genetic marker located in the thioesterase region of the fatty acid synthase gene is identified, said method comprising:
   a) providing a bovine genetic sample, said sample comprising nucleic acids from said bovine including the bovine fatty acid synthase gene; and
   b) detecting, in said genetic sample, the presence of at least one genetic marker that is linked to a fatty acid content trait, said genetic marker comprising a G nucleotide at the position corresponding to position 17924 of SEQ ID NO:6, wherein said G nucleotide is indicative of lower C14:0 content and lower C16:0 content in triacylglycerols (TAG) and a greater percentage of C18:1 content in phospholipids (PL) and TAG.

2. The method of claim 1 wherein said genetic marker is located within exon of the fatty acid synthase gene.

3. The method of claim 1 wherein said bovine subject is of the Angus breed.

4. The method of claim 2 wherein said marker results in an amino acid change in the fatty acid synthase protein.

5. The method of claim 1 wherein said marker is a SNP located at position 17924 of SEQ ID NO:6 encoding bovine fatty acid synthase.

6. The method of claim 5 wherein said SNP results in a change from threonine to alanine in the fatty acid synthase protein.

7. The method of claim 4 wherein said G at the position corresponding to position 17924 of SEQ ID NO:6 is correlated with lower C14:0 content, lower C16:0 content in TAG and/or to greater percentage of C18:1 content in both PL and TAG in the LD muscle than in bovines with an A at position 17924 of SEQ ID NO:6.

8. A method for identifying a bovine as having a fatty acid content, in said bovine's muscle tissue, comprising: lower C14:0 content and lower C16:0 content in triacylglycerols (TAG) and a greater percentage of C18:1 content in phospholipids (PL) and TAG, said method comprising:
   a) obtaining a biological sample from a bovine, said sample comprising nucleic acids from said bovine including the bovine fatty acid synthase gene;
   b) detecting, in said nucleic acids the presence of at least one allele of the bovine fatty acid synthase gene comprising a G nucleotide at the position corresponding to position 17924 of SEQ ID NO:6; and
   c) correlating the presence of at least one allele of the bovine fatty acid synthase gene comprising a G nucleotide at the position corresponding to position 17924 of SEQ ID NO:6 with a fatty acid content, in said bovine's muscle tissue, comprising: lower C14:0 content and lower C16:0 content in TAG and a greater percentage of C18:1 content in PL and TAG.

* * * * *